United States Patent
Shelton, IV et al.

(10) Patent No.: US 10,568,619 B2
(45) Date of Patent: Feb. 25, 2020

(54) SURGICAL PORT WITH WOUND CLOSURE CHANNELS

(71) Applicant: ETHICON LLC, Guaynabo, PR (US)

(72) Inventors: Frederick E. Shelton, IV, Hillsboro, OH (US); Jason L. Harris, Lebanon, OH (US); James G. Lee, Cincinnati, OH (US); Layne D. Christopher, Cincinnati, OH (US); Nichole Y. Kwee, Cincinnati, OH (US); Sol Posada, Cincinnati, OH (US); Patrick M. Schleitweiler, West Chester, OH (US); Anil R. Jadhav, Pune (IN); Tamara S. Vetro Widenhouse, Clarksville, OH (US)

(73) Assignee: Ethicon LLC, Guaynabo, PR (US)

( * ) Notice: Subject to any disclaimer, the term of this patent is extended or adjusted under 35 U.S.C. 154(b) by 192 days.

(21) Appl. No.: 15/637,707

(22) Filed: Jun. 29, 2017

(65) Prior Publication Data

US 2019/0000441 A1    Jan. 3, 2019

(51) Int. Cl.
  *A61B 17/04*     (2006.01)
  *A61B 17/34*     (2006.01)
  *A61B 17/00*     (2006.01)
(52) U.S. Cl.
  CPC ...... *A61B 17/0469* (2013.01); *A61B 17/0482* (2013.01); *A61B 17/3417* (2013.01); *A61B 17/0057* (2013.01); *A61B 2017/00637* (2013.01)
(58) Field of Classification Search
  CPC ............ A61B 17/0057; A61B 17/0293; A61B 17/0469; A61B 17/0482; A61B 17/0483;

(Continued)

(56) References Cited

U.S. PATENT DOCUMENTS

| | | | | |
|---|---|---|---|---|
| 5,180,365 A | * | 1/1993 | Ensminger | ........ A61M 39/0208 604/175 |
| 5,507,758 A | * | 4/1996 | Thomason | ......... A61B 17/0469 606/139 |

(Continued)

FOREIGN PATENT DOCUMENTS

WO    WO 2010/141418 A1    12/2010

OTHER PUBLICATIONS

U.S. Appl. No. 15/637,683, filed Jun. 29, 2017.

(Continued)

*Primary Examiner* — Ryan J. Severson
*Assistant Examiner* — Mohamed G Gabr
(74) *Attorney, Agent, or Firm* — Frost Brown Todd LLC

(57) ABSTRACT

A surgical access device includes a tissue retractor including a flexible body configured to engage tissue surrounding a tissue opening. A plurality of surgical instrument channels is arranged in a central portion of the tissue retractor. Each surgical instrument channel is configured to guide a surgical instrument distally through the surgical access device. At least one needle entrance port is arranged on a proximal portion of the surgical access device. At least one needle exit port is arranged distally of the needle entrance port. The at least one needle entrance port and the at least one needle exit port are configured to cooperate to define a needle channel extending distally through the surgical access device and obliquely relative to a central axis thereof. The needle channel is configured to guide a suture passer needle through the surgical access device and adjacent tissue to facilitate closure of the tissue opening.

20 Claims, 31 Drawing Sheets

(58) Field of Classification Search
CPC ............ A61B 17/3417; A61B 17/3423; A61B 17/3462; A61B 17/0218; A61B 17/3421; A61B 17/3474; A61B 2017/00637; A61B 2017/00663; A61B 2017/06042; A61B 2017/3466; A61B 2017/3445; A61B 2017/3447; A61B 2017/3449; A61B 2017/3419; A61M 39/0208

See application file for complete search history.

(56) References Cited

U.S. PATENT DOCUMENTS

| | | |
|---|---|---|
| 5,792,135 A | 8/1998 | Madhani et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 7,524,320 B2 | 4/2009 | Tierney |
| 7,691,098 B2 | 4/2010 | Wallace et al. |
| 7,806,891 B2 | 10/2010 | Nowlin et al. |
| 7,981,092 B2 | 7/2011 | Duke |
| 8,068,649 B2 | 11/2011 | Green |
| 8,226,553 B2 | 7/2012 | Shelton, IV et al. |
| 8,251,900 B2 | 8/2012 | Ortiz et al. |
| 8,353,824 B2 | 1/2013 | Shelton, IV et al. |
| 8,479,969 B2 | 7/2013 | Shelton, IV |
| 8,517,933 B2 | 8/2013 | Mohr |
| 8,545,515 B2 | 10/2013 | Prisco et al. |
| 8,551,115 B2 | 10/2013 | Steger et al. |
| 8,568,362 B2 | 10/2013 | Moreno et al. |
| 8,573,461 B2 | 11/2013 | Shelton, IV et al. |
| 8,573,465 B2 | 11/2013 | Shelton, IV |
| 8,579,807 B2 | 11/2013 | Moreno et al. |
| 8,602,288 B2 | 12/2013 | Shelton, IV et al. |
| 8,616,431 B2 | 12/2013 | Timm et al. |
| 8,623,028 B2 | 1/2014 | Rogers et al. |
| 8,636,686 B2 | 1/2014 | Minnelli et al. |
| 8,690,831 B2 | 4/2014 | Duke |
| 8,771,180 B2 | 7/2014 | Mohr |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,888,789 B2 | 11/2014 | Prisco et al. |
| 9,254,178 B2 | 2/2016 | Prisco et al. |
| 9,283,050 B2 | 3/2016 | Prisco et al. |
| 9,301,759 B2 | 4/2016 | Spivey et al. |
| 9,320,416 B2 | 4/2016 | Cooper et al. |
| 9,339,341 B2 | 5/2016 | Cooper |
| 9,358,074 B2 | 6/2016 | Schena et al. |
| 9,572,481 B2 | 2/2017 | Duindam et al. |
| 9,636,186 B2 | 5/2017 | Kumar et al. |
| 9,687,226 B2 | 6/2017 | Hodgkinson et al. |
| 9,700,303 B2 | 7/2017 | Prior et al. |
| 2008/0200950 A1 | 8/2008 | Wohlert |
| 2010/0261975 A1* | 10/2010 | Huey et al. ........ A61B 17/3423 600/208 |
| 2011/0066001 A1* | 3/2011 | Shelton, IV ....... A61B 17/3423 600/208 |
| 2011/0071542 A1* | 3/2011 | Prisco ............... A61M 25/0105 606/130 |
| 2014/0066717 A1 | 3/2014 | Rogers et al. |
| 2015/0038793 A1 | 2/2015 | Prior et al. |
| 2017/0079639 A1 | 3/2017 | Mohajer-Shojaee |
| 2017/0128041 A1 | 5/2017 | Hasser et al. |
| 2017/0128144 A1 | 5/2017 | Hasser et al. |
| 2017/0128145 A1 | 5/2017 | Hasser et al. |
| 2017/0281154 A1 | 10/2017 | Hess et al. |

OTHER PUBLICATIONS

U.S. Appl. No. 15/637,688, filed Jun. 29, 2017.
U.S. Appl. No. 15/637,690, filed Jun. 29, 2017.
U.S. Appl. No. 15/637,696, filed Jun. 29, 2017.
U.S. Appl. No. 15/637,702, filed Jun. 29, 2017.
U.S. Appl. No. 15/637,712, filed Jun. 29, 2017.
U.S. Appl. No. 15/637,735, filed Jun. 29, 2017.
U.S. Appl. No. 15/637,778, filed Jun. 29, 2017.
European Search Report and Written Opinion dated Sep. 18, 2018 for Application No. EP 18180499.8, 9 pgs.
International Search Report and Written Opinion dated Sep. 18, 2018 for Application No. PCT/IB2018/054436, 12 pgs.

* cited by examiner

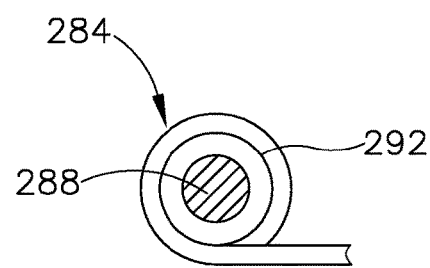
Fig.19
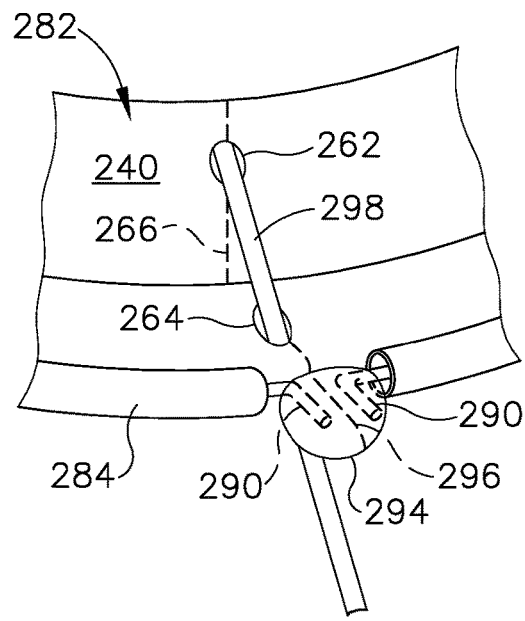 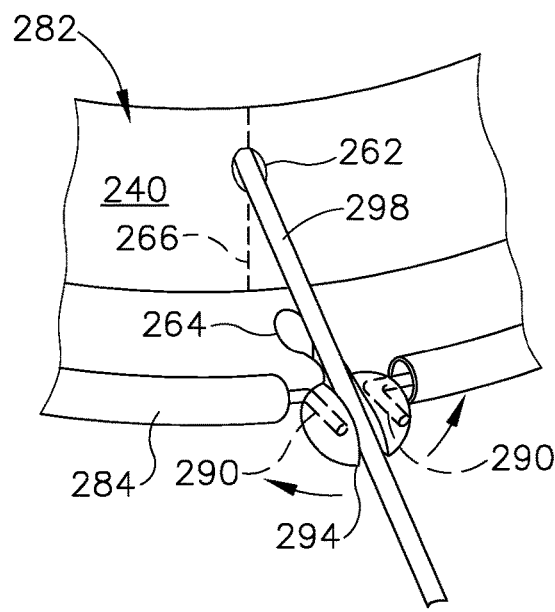
Fig.20A  Fig.20B

SURGICAL PORT WITH WOUND CLOSURE CHANNELS

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Traditional trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Examples of trocar assemblies, components thereof, and other varieties of surgical access devices and wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008, now abandoned; U.S. Pat. Pub. No. 2015/0038793, entitled "Devices, Systems, and Methods for Providing Surgical Access and Facilitating Closure of Surgical Access Openings," published on Feb. 5, 2015, issued as U.S. Pat. No. 10,258,324 on Apr. 16, 2019; U.S. Pat Pub. No. 2015/0038994, entitled "Devices, Systems, and Methods for Providing Surgical Access and Facilitating Closure of Surgical Access Openings," published on Feb. 5, 2015, issued as U.S. Pat. No. 9,700,303 on Jul. 11, 2017; and U.S. Pat. Pub. No. 2015/0094741, entitled "Wound Closure Device including Mesh Barrier." Published on Apr. 2, 2015, issued as U.S. Pat. No. 9,687,226 on Jun. 27, 2017. The disclosure of each of the above-cited U.S. patents and Publications is incorporated by reference herein.

Surgical instruments for use with such surgical access devices may have a distal end effector for engaging tissue through the access device in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 19 depicts a side sectional view of the distal flange of the surgical access device of FIG. 18;

FIG. 20A depicts an enlarged perspective view of the distal flange and a medial body portion of the tissue retractor of FIG. 18, showing a suture thread exiting the medial body portion and extending through the distal flange at a location aligned with adjacent ends of ring segments of a resilient ring housed within the distal flange;

FIG. 20B depicts an enlarged perspective view of the distal flange and medial body portion of FIG. 20A, showing decoupling of the adjacent ends of the ring segments and separation of adjacent portions of the distal flange to thereby enable the suture thread to be freed from the distal flange;

Figure 1:
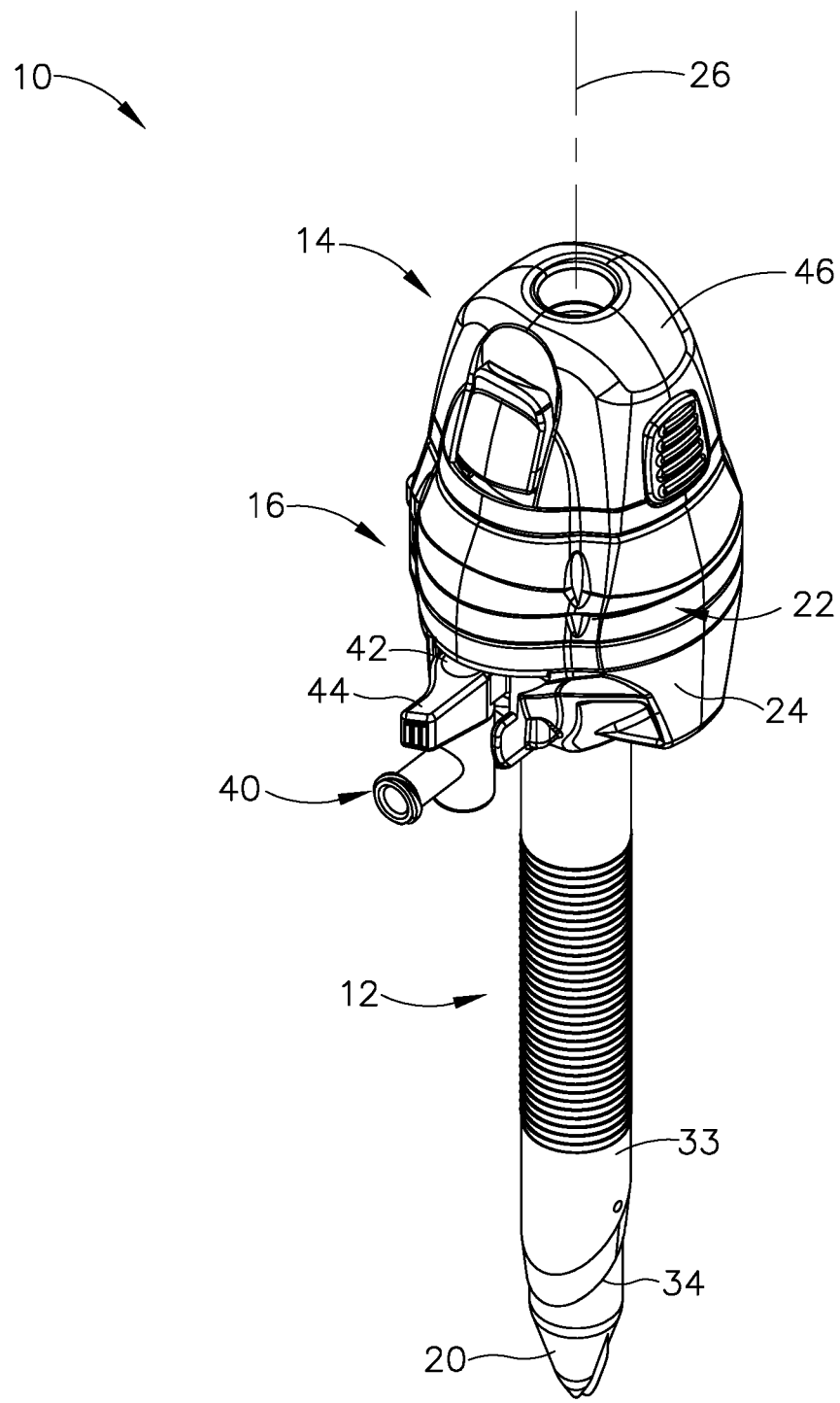
FIG. 1 depicts a perspective view of an exemplary trocar assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL ACCESS DEVICE

Figure 2:
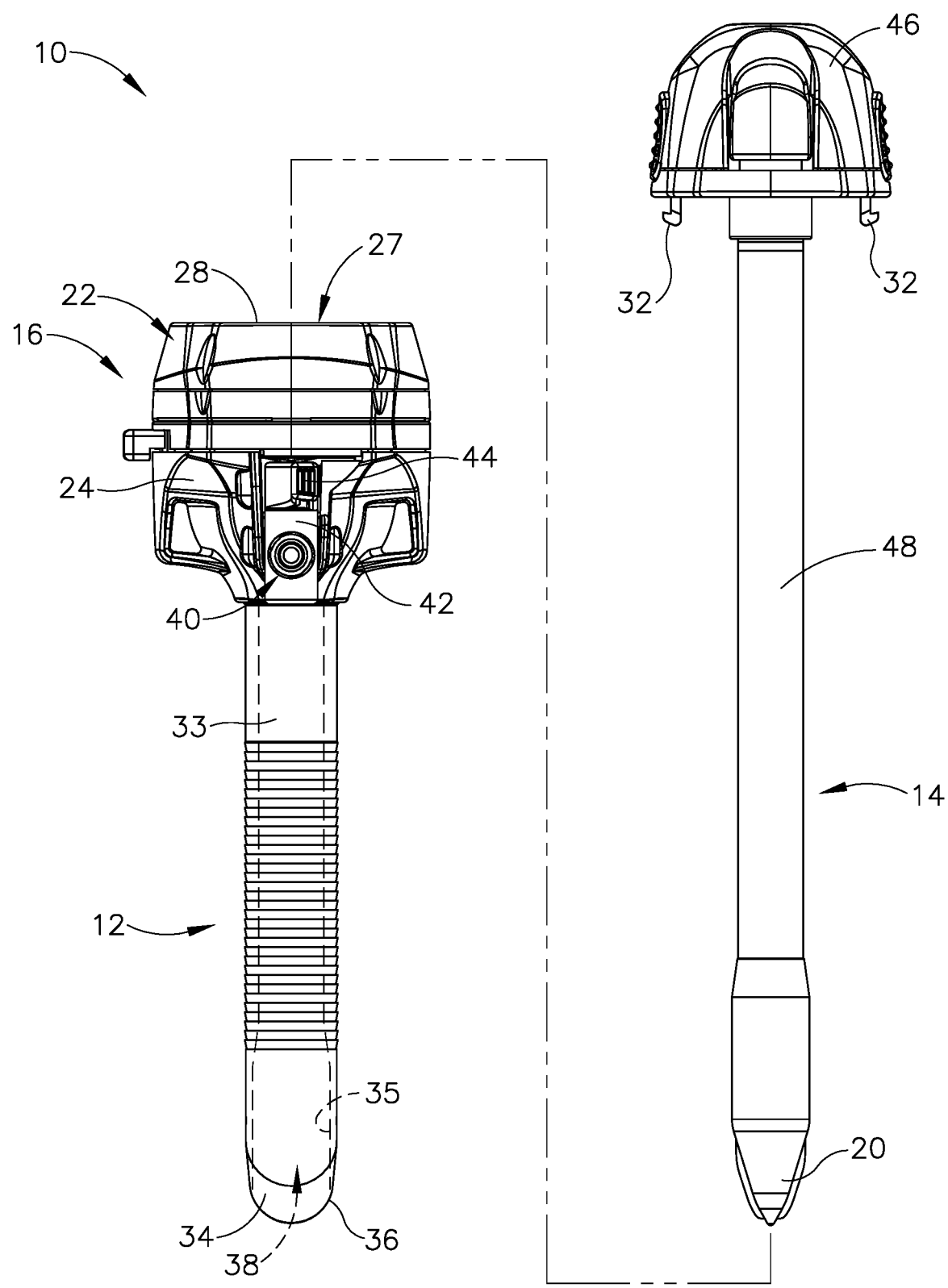
FIG. 2 depicts a partially exploded side elevational view of the trocar assembly of FIG. 1 having a trocar housing, a trocar cannula, and an obturator.

FIGS. 1-2 depict an exemplary surgical access device in the form of an exemplary trocar assembly (10) that includes a trocar cannula (12) and a trocar obturator (14). Trocar obturator (14) is removably received within trocar cannula (12) through a trocar housing (16) of trocar cannula (12). As shown in FIG. 1 with trocar obturator (14) positioned within trocar cannula (12), a clinician inserts trocar assembly (12) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator (14) projects distally from trocar cannula (12) to puncture tissue (17) (see FIG. 3A) for introducing a distal end portion of trocar cannula (12) into cavity (18) (see FIG. 3B). The clinician proximally withdraws trocar obturator (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14).

However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained within cap (22) and is configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

Duckbill seal is further configured to be manipulated to provide an opening to working channel (38) that is larger than a corresponding opening provided by instrument seal. This larger opening provided by duckbill seal may facilitate extraction of bodily tissue through trocar housing (16) during a surgical procedure. In particular, cap (22) may be removed, and proximal instrument seal along with it, to expose the duckbill seal and thereby enable a surgeon to extract bodily tissue proximally through the duckbill seal opening that would otherwise be too large to extract proximally through the instrument seal opening.

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to puncture tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
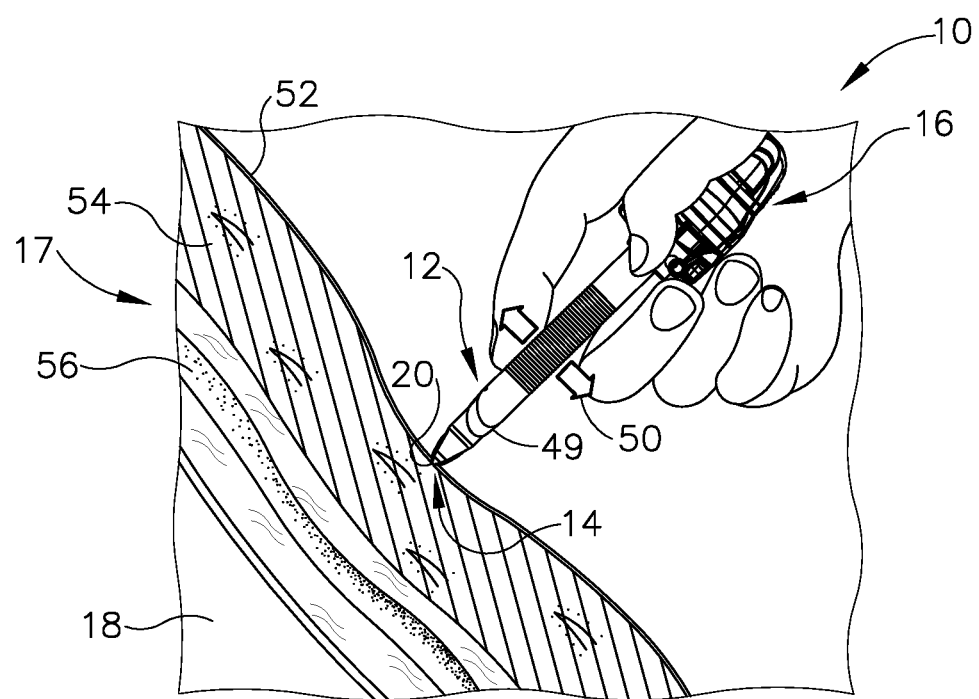
FIG. 3A depicts a side sectional view of tissue of a patient with the trocar assembly of FIG. 1 being manipulated by a clinician through the tissue.
Figure 3B:
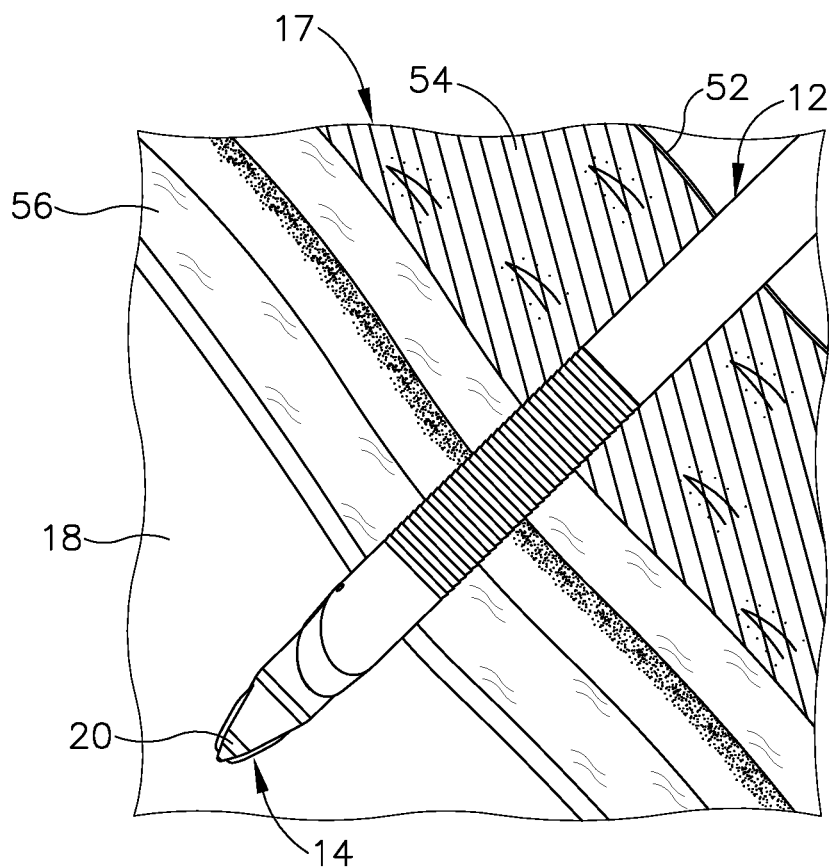
FIG. 3B depicts a side sectional view of the tissue and trocar assembly of FIG. 3A, with the trocar assembly of FIG. 1 inserted through the tissue and received within a cavity of the patient.
Figure 3C:
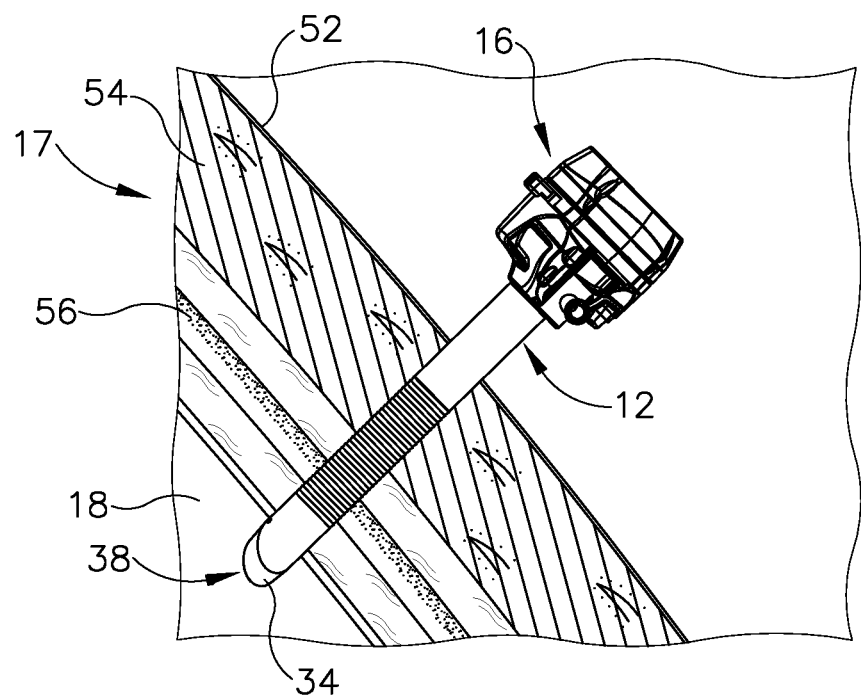
FIG. 3C depicts a side sectional view of the tissue and trocar assembly of FIG. 3A, with the obturator withdrawn from the trocar cannula for accessing the cavity via a working channel through the trocar cannula and the trocar housing.
Figure 3D:
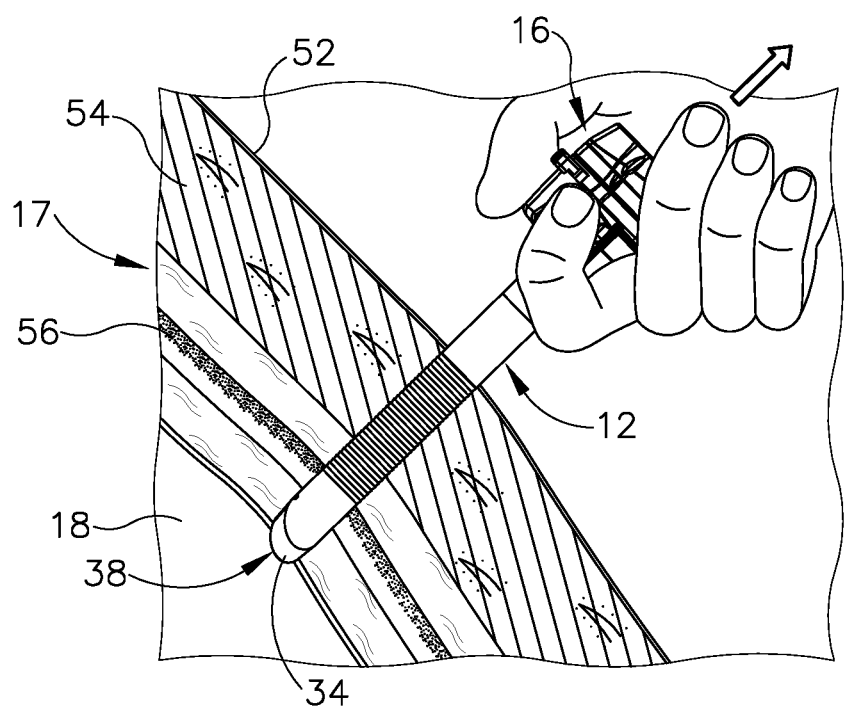
FIG. 3D depicts a side sectional view of the tissue and trocar assembly of FIG. 3C, with the trocar housing and the trocar cannula being removed from the cavity and the tissue of the patient.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

Figure 4A:
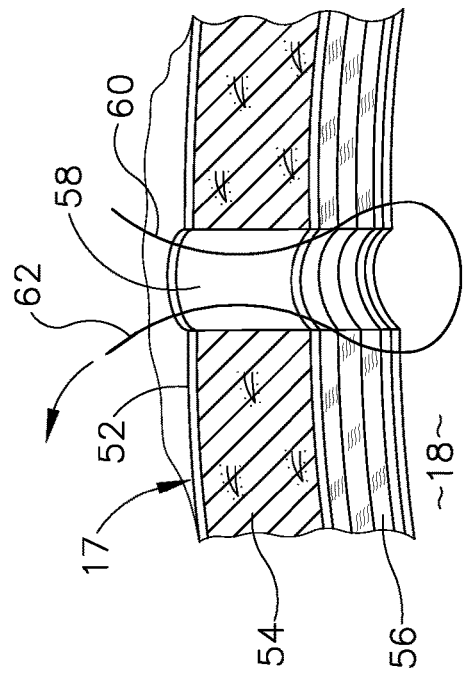
FIG. 4A depicts another side sectional view of the tissue shown in FIGS. 3A-3D following removal of the trocar assembly of FIG. 1, with an opening through the tissue and a suture thread being introduced into a portion of the tissue for suturing the opening closed.
Figure 4B:
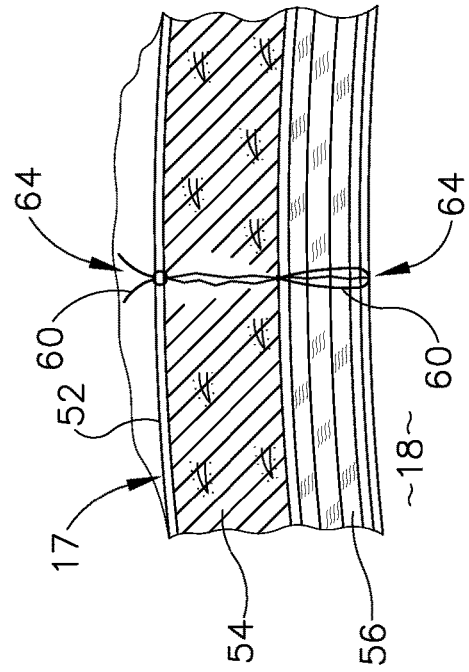
FIG. 4B depicts a side sectional view of the tissue of FIG. 4A, with the suture thread being introduced though another portion of the tissue and pulled through the tissue.
Figure 4C:
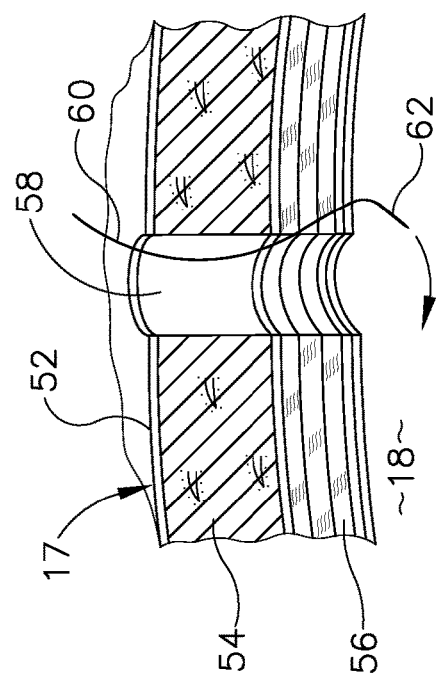
FIG. 4C depicts a side sectional view of the tissue of FIG. 4A, with the suture thread tightened and knotted for at least partially closing the opening.
Figure 4D:
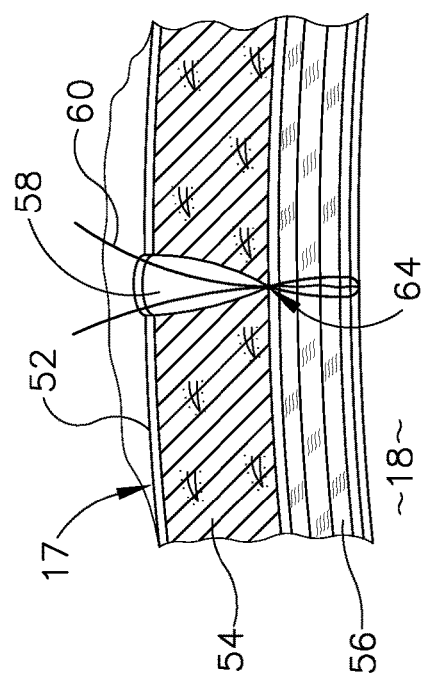
FIG. 4D depicts a side sectional view of the tissue of FIG. 4A, with additional suturing for further closing the opening.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance distally from tissue opening (58) in order to provide a relatively close proximity to tissue opening (58); but also at a sufficient distance to provide ample fascia (56) for anchoring suture thread (60) therein. Additionally, the clinician angles a tip of needle (62) obliquely away from a central axis of opening (58) at a suitable angle in order to achieve sufficient "bite" when anchoring suture thread (60) within fascia (56). As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed Apr. 1, 2016, issued as U.S. Pat. No. 10,299,785 on May 28, 2019, which is incorporated by reference herein in its entirety, describes an alternative trocar assembly and suturing technique. To this end, alternative trocar assemblies and suturing techniques may be used in any combination as desired by the clinician.

II. EXEMPLARY SINGLE-INCISION SURGICAL ACCESS DEVICES HAVING INTEGRATED SUTURE GUIDE FEATURES

In various laparoscopic surgical procedures, and particularly those conducted in the abdominal cavity, a surgeon may need to direct two or more surgical instruments into the cavity simultaneously in order to access and provide effective treatment to tissue. It is generally desirable, however, to minimize the quantity of surgical openings formed in the abdominal wall to thereby mitigate tissue trauma, cosmetic damage, and post-operation recovery time for the patient. Accordingly, in some procedures a single surgical access device having multiple instrument channels may be utilized, and inserted through a single opening (e.g., formed by incision) in the abdominal wall tissue. Such devices are commonly referred to as "single-incision" or "single-site" surgical access devices (or "ports"). In some examples, one or more of the instrument channels and the corresponding surgical instruments inserted therethrough may be of a generally smaller diameter, such as approximately 5 millimeters or less, for example. Laparoscopic procedures employing such devices may be referred to as "mini-laparoscopy."

The single tissue opening formed for a single-incision surgical access device is often arranged in the patient umbilicus (or navel). Advantageously, the umbilicus is generally well-hidden, of lesser thickness, and less vascularized than surrounding regions of the abdominal wall. Accordingly, an umbilical incision can be easily enlarged without significantly compromising cosmesis, and without increasing the risk of wound complications. Nevertheless, the incision created for a single-incision surgical access device remains substantially larger in diameter than an incision created for any one of the surgical instruments directed through the surgical access device. For example, in some cases the single incision may be up to 20-25 millimeters in diameter.

Each of the exemplary single-incision surgical access devices described below includes integrated suture guide features that enable the surgical access device to be implemented as a wound closure device configured to effectively close the tissue opening in which the device is inserted. In particular, the exemplary suture guide features described below are configured to guide the application of multiple sutures along respective suture paths extending distally through the access device and adjacent tissue, obliquely relative to a central axis of the access device. As used herein, the term "oblique" and variations thereof means neither parallel nor perpendicular to the referenced axis, such as the central axis of a surgical access device. The resulting effective closure of the tissue opening promotes swift healing and minimizes tissue scarring. Advantageously, the exemplary single-incision surgical access devices described below are further configured to release suture threads directed therethrough and thereby promote easy removal of the surgical access devices from tissue openings following application of suture threads.

Figure 5:
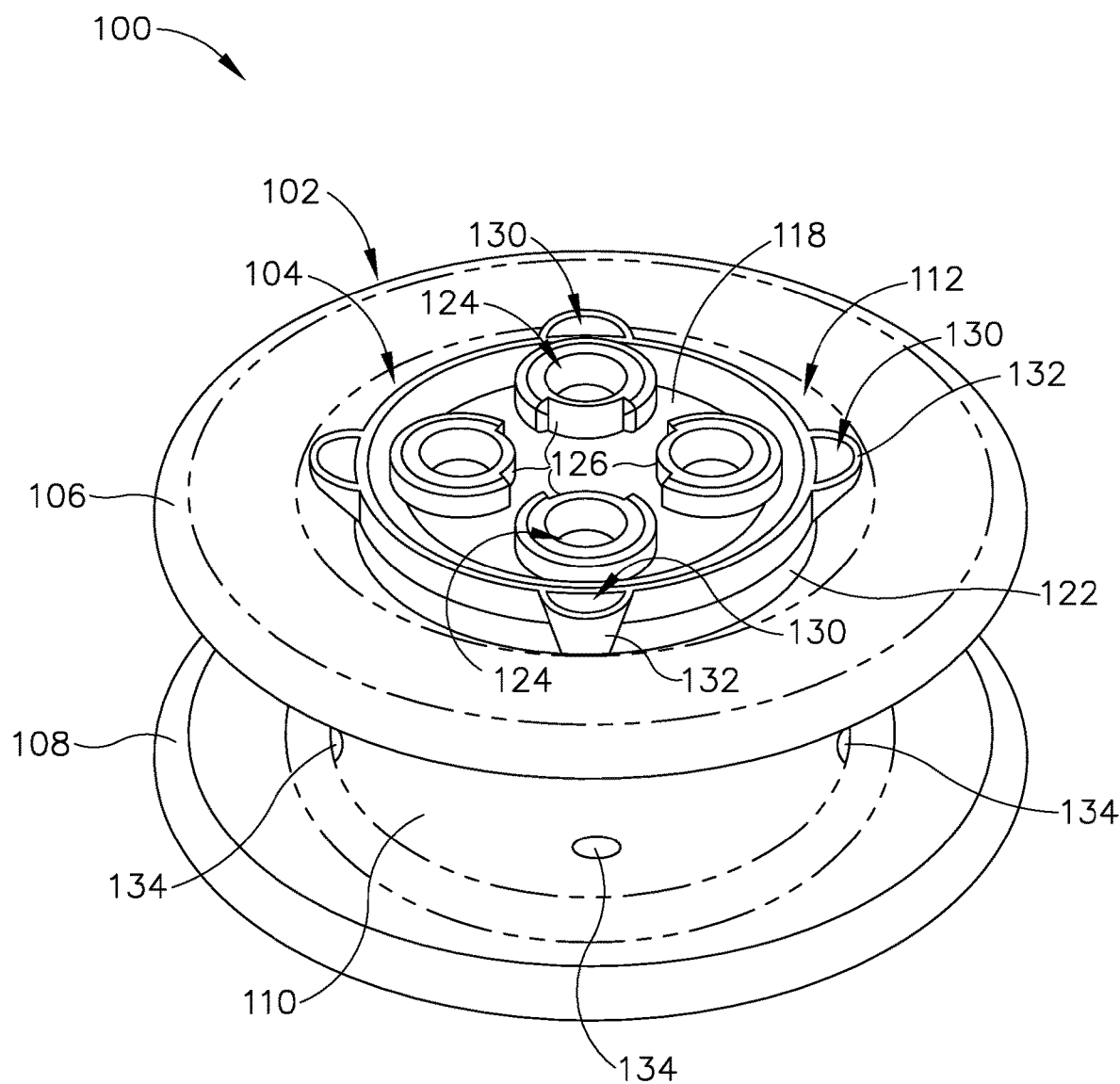
FIG. 5 depicts a perspective view of an exemplary single-incision surgical access device.
Figure 6:
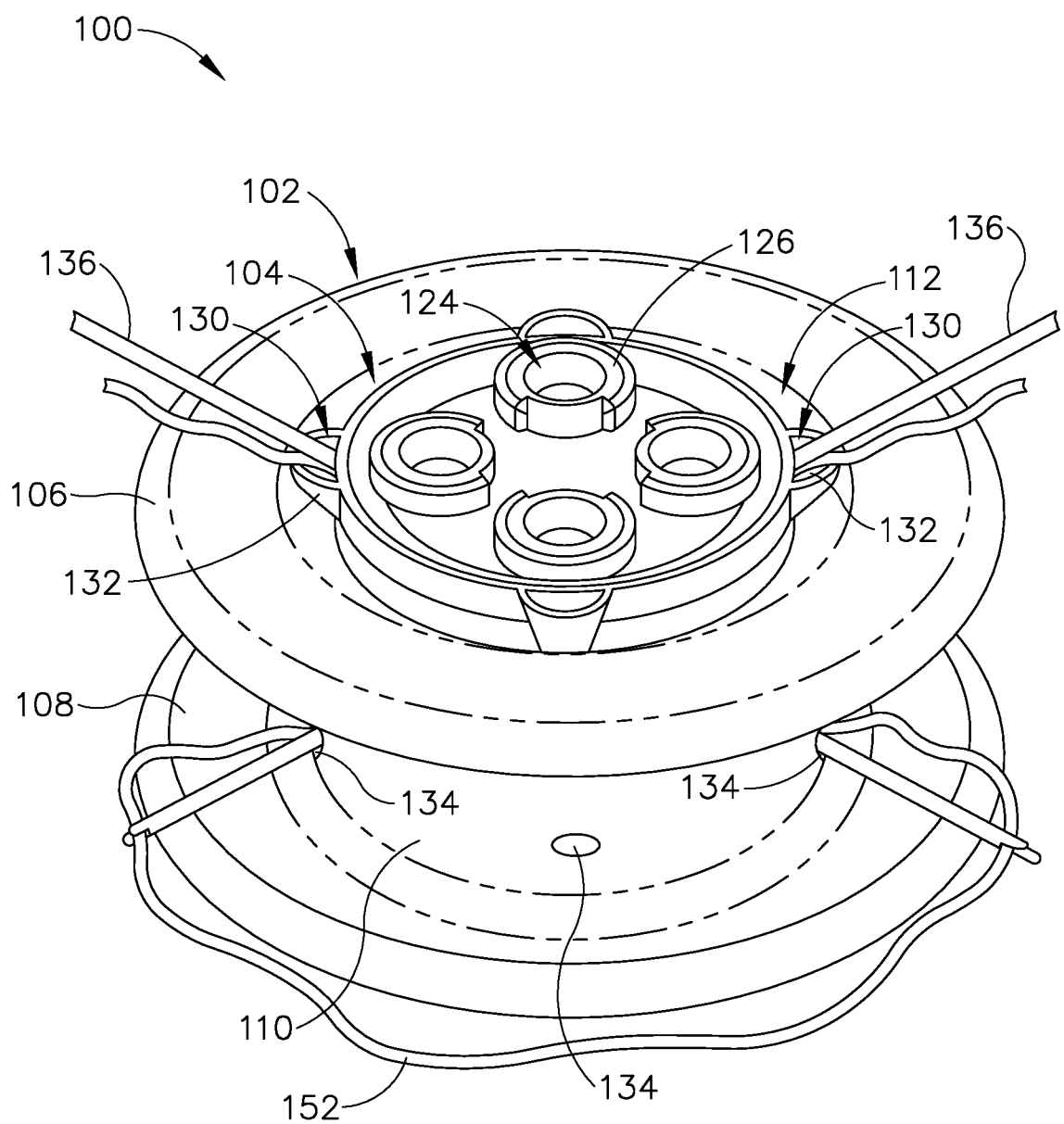
FIG. 6 depicts a perspective view of the surgical access device of FIG. 5, showing a suture passer needle and a suture thread directed through first and second needle channels of the device.
Figure 7:
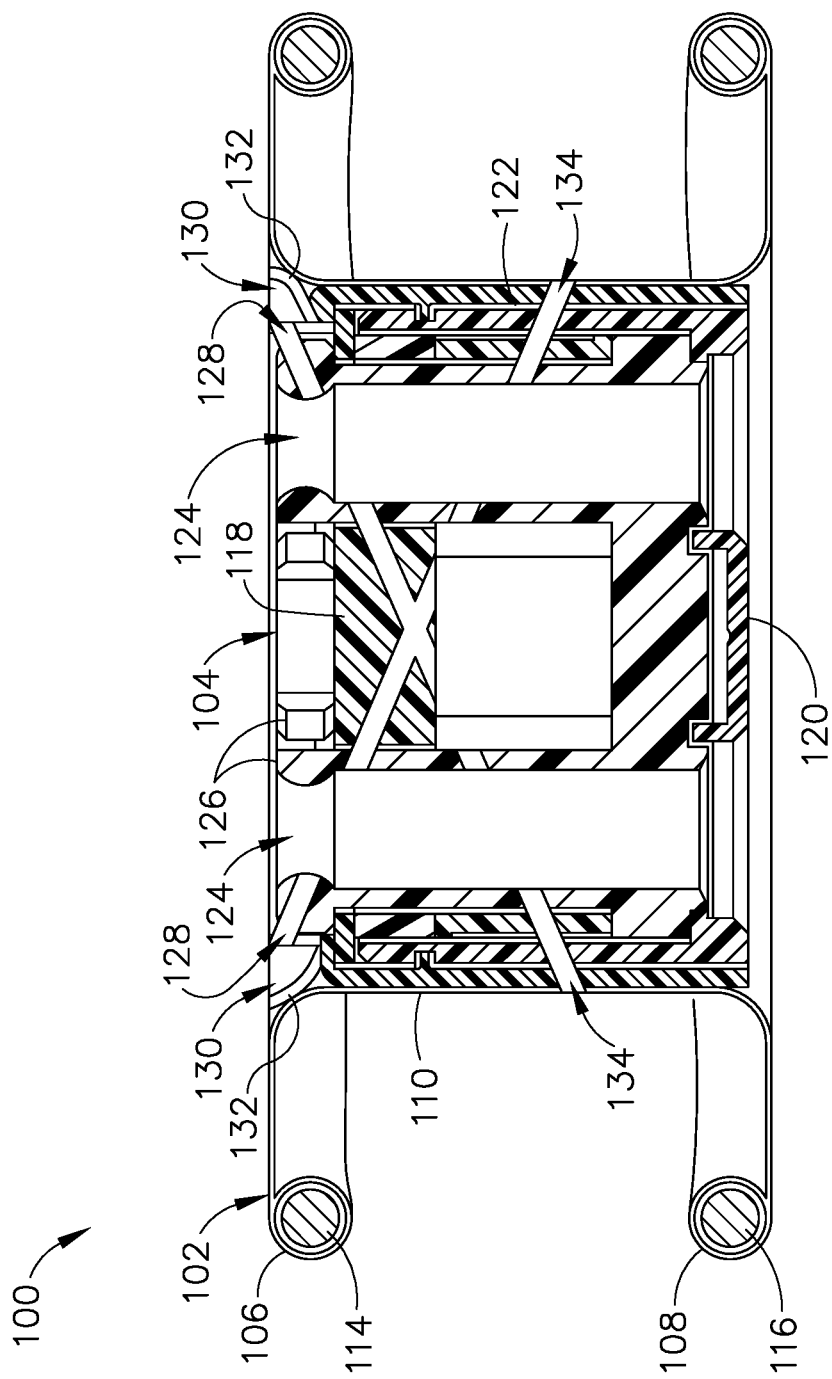
FIG. 7 depicts a side sectional view of the surgical access device of FIG. 5, showing first and second needle channels of the device.

A. Exemplary Single-Incision Surgical Access Device Having Insert with Needle Entry Guide Members FIGS. 5-7 show an exemplary single-incision surgical access device (100) having integrated suture guide features configured to facilitate closure of a tissue opening (or wound) in which access device (100) is positioned for a surgical procedure. Surgical access device (100) generally includes a tissue retractor (102) and an insert (104) arranged within a central region of tissue retractor (102). Tissue retractor (102) includes a flexible annular body having a proximal flange (106), a distal flange (108), a medial body portion (110) extending axially between proximal and distal flanges (106, 108), and a central passage (112) (also referred to as a "working channel") extending axially through the annular body.

Figure 8A:
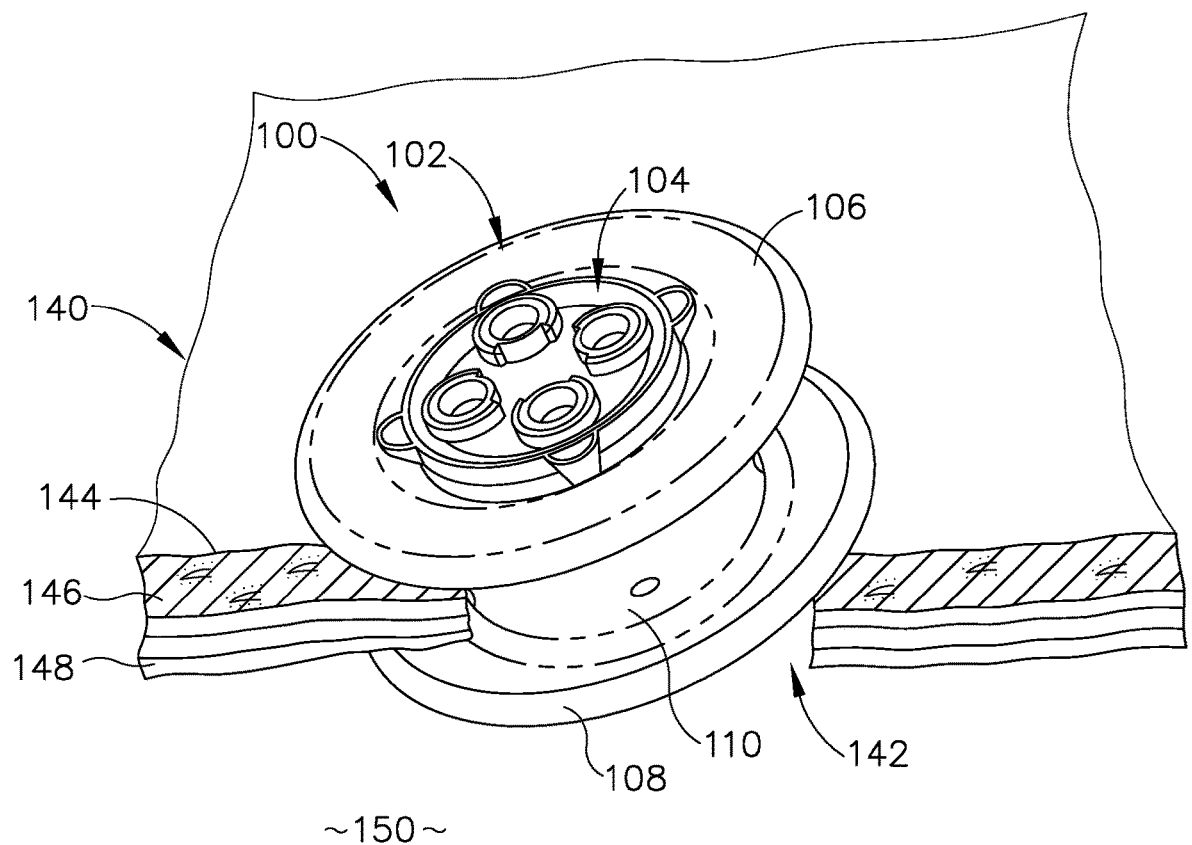
FIG. 8A depicts a perspective, partial side sectional view of the surgical access device of FIG. 5, showing the device being positioned within a tissue opening.
Figure 8B:
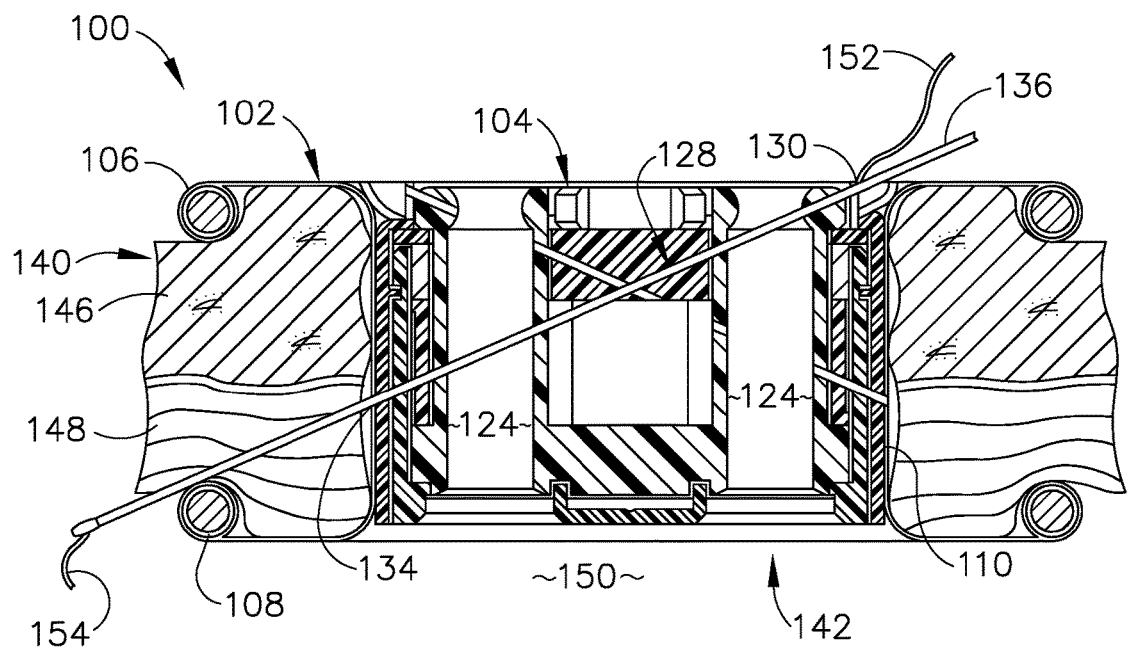
FIG. 8B depicts a schematic side sectional view of the surgical access device and tissue of FIG. 8A, showing a suture passer needle and a suture thread being directed along a first suture path extending through a first needle channel of the device and adjacent tissue.
Figure 8C:
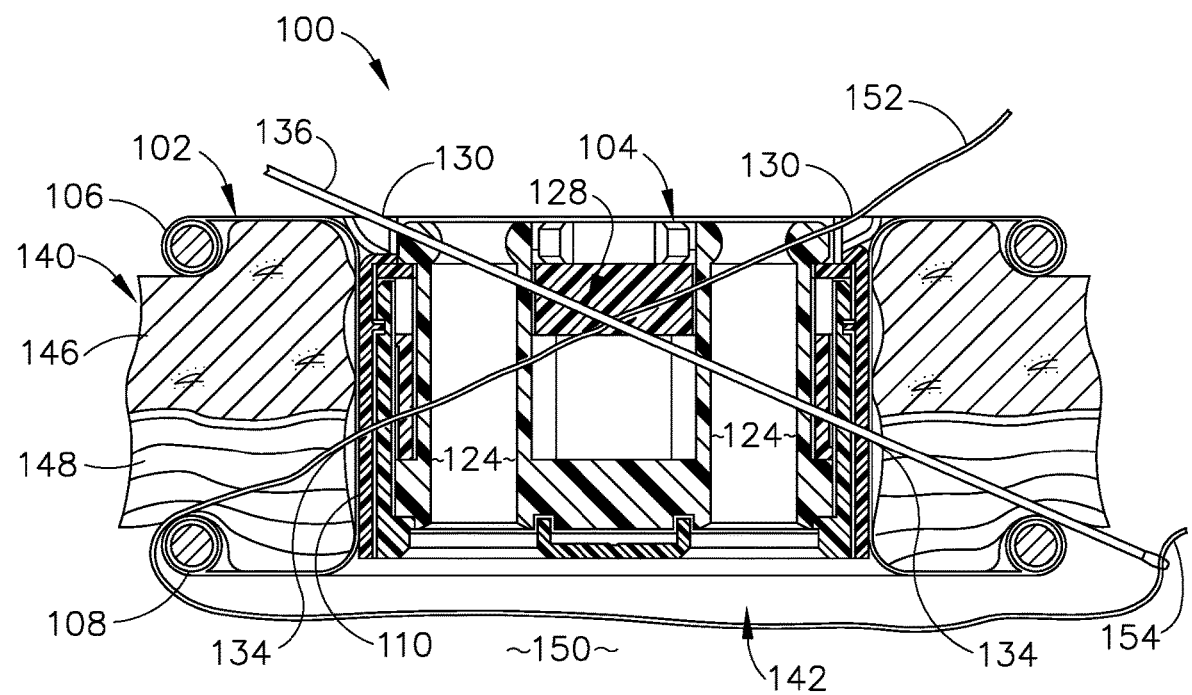
FIG. 8C depicts a schematic side sectional view of the surgical access device and tissue of FIG. 8B, showing the suture passer needle being directed along a second suture path extending through a second needle channel of the device and adjacent tissue to recapture a deposited end of the suture thread.
Figure 8D:
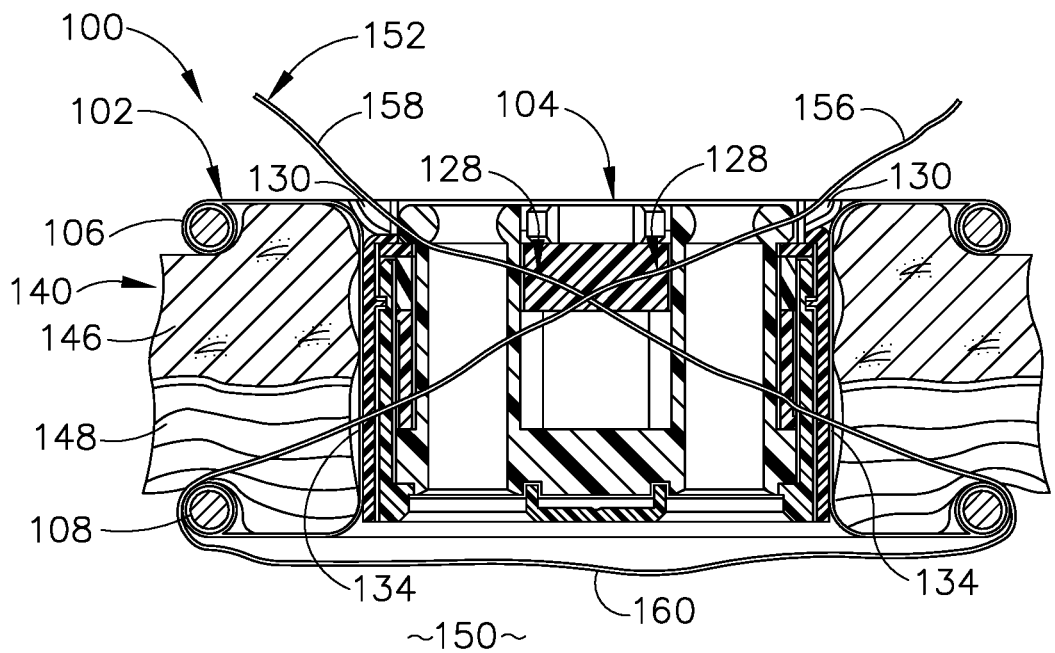
FIG. 8D depicts a schematic side sectional view of the surgical access device and tissue of FIG. 8C, showing the suture thread extending through the device and tissue along the first and second suture paths.

One or more portions of tissue retractor (102), including distal flange (108), are formed of a suitably resilient material, such as silicone for example. Accordingly, tissue retractor (102) is configured to elastically deform while being inserted into a tissue opening, as shown in FIG. 8A, and then resiliently return to or toward its original shape once fully positioned within the opening. In particular, as shown in FIGS. 8B-8D, proximal and distal flanges (106, 108) are configured to exert inwardly directed axial bias forces on proximal and distal tissue surfaces, respectively, and medial body portion (110) is configured to simultaneously exert an outwardly directed radial bias force on an inner tissue wall. Consequently, tissue retractor (102) is configured to resiliently clamp tissue arranged between proximal and distal flanges (106, 108) when access device (100) is positioned within a tissue opening, thereby releasably securing access device (100) positionally relative to tissue. As shown best in FIG. 7, an outer lip of proximal flange (106) houses a proximal resilient ring (114), and an outer lip of distal flange (108) houses a distal resilient ring (116). Resilient rings (114, 116) may be formed of any suitably resilient material, such as nitinol, and are configured to aid tissue retractor (102) in resiliently maintaining its annular shape when positioned within a tissue opening.

Insert (104) is supported concentrically within central passage (112) of tissue retractor (102) and may be configured as a rigid assembly defining a generally cylindrical body having a proximal face (118), a distal face (120), a sidewall (122), and a plurality of surgical instrument channels (124) extending axially through the cylindrical body and opening to proximal and distal faces (118, 120). As shown in FIG. 7, proximal face (118) of insert (104) is oriented toward proximal flange (106) of tissue retractor (102), and distal face (120) is oriented toward distal flange (108). Each surgical instrument channel (124) has an entrance end at proximal face (118) and an exit end at distal face (120), and is configured to guide a surgical instrument (not shown) distally through access device (100) and into a body cavity. Such surgical instruments may include various endoscopic instruments such as endoscopes, grasping instruments, and cutting instruments, for example. Proximal face (118) of insert (104) includes a plurality of instrument entry guide members (126), shown in the form of ring structures, configured to guide insertion of surgical instruments into the entrance ends of instrument channels (124). In the present example, four instrument channels (124) of equal diameter are provided and are arranged with uniform circumferential spacing about the central axis of insert (104). In other examples, various other quantities, sizes, and arrangements of surgical instrument channels (124) may be provided.

In some versions of surgical access device (100), insert (104) is releasably coupled to tissue retractor (102) and may be selectively decoupled from retractor (102), for example by pushing insert (104) proximally or distally relative to tissue retractor (102). In other versions, insert (104) may be permanently coupled to tissue retractor (102). Insert (104) and/or tissue retractor (102) may be further configured in accordance with one or more teachings of U.S. Pat. No. 8,226,553, entitled "Access Device with Insert," issued Jul. 24, 2012, the disclosure of which is incorporated by reference herein.

Single-incision surgical access device (100) further includes a plurality of suture guide features that enable access device (100) to facilitate closure of the tissue opening in which access device (100) is positioned for one or more surgical procedures. Specifically, as shown best in FIG. 7, access device (100) includes a plurality of circumferentially arranged needle channels (128) extending distally through access device (100) and obliquely relative to the central axis of access device (100). As shown best in FIGS. 5 and 6, each needle channel (128) is defined by a needle entrance port (130) arranged on a proximal portion of access device (100), and a corresponding needle exit port (134) that communicates with and is arranged distally of its respective needle entrance port (130). As shown in FIGS. 6 and 8B-8D, described below, each needle channel (128) is configured to guide a suture passer needle (136) and a suture thread carried by suture passer needle (136) through surgical access device (100) and adjacent tissue along a respective suture path. Each needle channel (128) and its respective suture path extends at an oblique angle relative to the central axis of access device (100) (referred to herein as a "suture path angle").

In the present example, each needle entrance port (130) is defined by a corresponding needle entry guide member (132) that protrudes radially outwardly from an outer perimeter of proximal face (118) of insert (104) and joins with sidewall (122). Additionally, each needle exit port (134) is arranged on a distal portion of medial body portion (110) of tissue retractor (102). Further, surgical access device (100) includes four needle entrance ports (130) and four needle exit ports (134), collectively defining four needle channels (128). As described below, each needle channel (128) is configured to cooperate with one of the other needle channels (128) to guide application of a corresponding suture thread to tissue along a respective pair of suture paths. Accordingly, the access device (100) of the present example is configured to guide application of two suture threads to tissue. However, persons skilled in the art will recognize that access device (100) may be provided with suture guide features of various other quantities to guide application of three or more suture threads.

As shown best in FIGS. 5 and 6, a first pair of needle entrance ports (130) and corresponding needle exit ports (134) are arranged in a first axial plane extending through the central axis of access device (100). A second pair of needle entrance ports (130) and corresponding needle exit ports (134) are arranged in a second axial plane extending through the central axis, perpendicularly to the first axial plane. Accordingly, needle ports (130, 134) are arranged with uniform circumferential spacing about the central axis, and each needle entrance port (130) is diametrically opposed from its respective needle exit port (134) as well as from another needle entrance port (130). Additionally, in the present example needle entrance ports (130) and needle exit ports (134) are aligned circumferentially with surgical instrument channels (124), such that each needle channel (128) extends obliquely through a pair of instrument channels (124), as shown in FIG. 7. In other versions of surgical access device (100), needle ports (130, 134) may be circumferentially offset from instrument channels (124) such that each needle channel (128) extends between instrument channels (124) without passing through instrument channels (124).

As used herein, the term "diametrically opposed" and variations thereof is intended to encompass configurations in which the referenced structures are arranged at different longitudinal locations along a referenced axis, such as central axis of surgical access device (100). For instance, in the present example each needle entrance port (130) is spaced proximally from its respective needle exit port (134), though needle ports (130, 134) are still understood to be diametrically opposed from one another along the same axially extending plane, as described above. Of course, in alternative versions of access device (100), one or more needle entrance ports (130) and their respective needle exit ports (134) may be arranged in different axial planes such that the needle ports (130, 134) are not diametrically opposed to one another. It will be further understood that needle entrance and exit ports (130, 32) may be circumferentially arranged about the central axis of access device (100) in various other suitable configurations.

In the present example, needle exit ports (134) are all arranged in a first plane extending transversely to the central axis of surgical access device (100), and needle exit ports (134) are all arranged in a second plane spaced distally from and extending parallel to the first transverse plane. Accordingly, needle exit ports (134) are arranged with uniform (or equal) axial spacing relative to needle entrance ports (130), such that needle channels (128) and their corresponding suture paths define uniform suture path angles relative to the central axis of surgical access device (100). In other versions of access device (100), the axial spacing between needle entrance ports (130) and needle exit ports (134) may be nonuniform such that needle channels (128) and their suture paths define nonuniform suture path angles relative to the central axis. In configurations in which each needle channel (128) and its suture path defines the same suture path angle relative to the central axis, such as in the present example, needle channels (128) and their suture paths may intersect one another at the central axis of access device (100).

Surgical access device (100) may further include an insufflation port (not shown) configured to direct insufflation fluid, such as carbon dioxide, from a fluid source into the body cavity to which surgical access device (100) provides access. Access device (100) may further include a plurality of sealing elements (not shown) arranged in one or more instrument channels (124) and/or needle channels (128) for maintaining insufflation. For example, one or more instrument channels (124) may include a sealing element configured to sealingly engage the outer surface of a surgical instrument inserted therethrough, or a sealing element configured to maintain a generally air-tight seal when no instrument is arranged within instrument channel (124), such as a duckbill seal. Additionally, one or more needle channels (128) may include a sealing element, such as a pierceable sealing element, configured to sealingly engage the outer surface of a suture passer needle (136) directed through needle channel (128) and/or maintain a generally air-tight seal when no suture passer needle (136) is arranged within needle channel (128).

B. Exemplary Wound Closure Procedure Using Single-Incision Surgical Access Device Having Insert with Needle Entry Guide Members FIGS. 8A-8H show steps of an exemplary procedure for suturing closed a tissue opening (142) (or wound) formed in tissue (140) for placement of single-incision surgical access device (100), using access device (100) as a wound closure device. Like tissue (17) described above, tissue (140) includes outward superficial layers and inward deeper layers. Superficial layers generally include an outer layer of skin (144) and an inner layer of fat (146). The deeper layers include layers of fascia (148), which are fibrous and flexible with relatively higher tensile strength than the superficial layers. Tissue opening opens distally to a body cavity (150). In exemplary procedures, tissue opening (142) may be located in the patient umbilicus such that tissue opening (142) opens distally to the abdominal cavity.

FIG. 8A shows surgical access device (100) being positioned within tissue opening (142). As described above, tissue retractor (102) of access device (100) is configured to elastically deform to facilitate insertion of access device (100) into tissue opening (142). Upon being fully positioned, tissue retractor (102) resiliently returns to or toward its original shape, thereby securing tissue (140) between proximal and distal flanges (106, 108) of tissue retractor (102), as shown in FIG. 8B. Following placement of access device (100) within tissue opening (142), a surgical procedure may be conducted by inserting one or more surgical instruments (not shown) distally through respective surgical instrument channels (124) to access tissue within body cavity (150).

Following completion of the surgical procedure, the integrated suture guide features of surgical access device (100) are utilized to guide application of multiple suture threads to tissue (140) to thereby facilitate effective closure of tissue opening (142). In particular, as shown in FIG. 8B, a suture passer needle (136) carrying a thread end (154) of a first suture thread (152) is directed distally through surgical access device (100) and adjacent tissue fascia (148) along a first suture path. In particular, suture passer needle (136) and thread end (154) are directed through a first needle entrance port (130) arranged on a first side portion of access device (100), and along a respective first needle channel (128) extending through insert (104) and exiting through a corresponding first needle exit port (134) arranged on a second side portion of access device (100). Suture passer needle (136) and thread end (154) continue to be guided by needle channel (128) to pass proximally over distal flange (108) of tissue retractor (102) and through a first portion of tissue fascia (148), into body cavity (150). Suture passer needle (136) is manipulated to deposit thread end (154) within body cavity (150), and is then withdrawn proximally from surgical access device (100) along the first suture path. In some examples, suture passer needle (136) may include one or more steerable sections, such as a steerable tip (not shown), configured to direct thread end (154) in a selected direction within body cavity (150) to facilitate subsequent steps of the wound closure procedure, described below. It will be appreciated that any of the exemplary suture passer needles described below may include one or more steerable sections configured to facilitate application of a suture thread to tissue (140) through a single-incision surgical access device disclosed herein.

As shown in FIG. 8C, suture passer needle (136) is then directed distally through surgical access device (100) and an adjacent second portion of tissue fascia (148) along a second suture path. In particular, suture passer needle (136) is directed through a second needle entrance port (130) arranged on the second side portion of access device (100), and along a respective second needle channel (128) extending through insert (104) and exiting through a corresponding second needle exit port (134) arranged on the first side portion of access device (100). Suture passer needle (136) is further guided by second needle channel (128) to pass proximally over distal flange (108) of tissue retractor (102) and through a second portion of tissue fascia (148), into body cavity (150). Suture passer needle (136) is then manipulated, for example with the assistance of a steerable section thereof (not shown), to recapture thread end (154) of first suture thread (152) within body cavity (150). Though not shown, one or more surgical instruments may be directed distally through instrument channels (124) to engage thread end (154) and assist in directing it from the first side of access device (100) toward the second side so thread end (154) may be effectively reached and recaptured by suture passer needle (136) directed along the second suture path.

Suture passer needle (136) and thread end (154) are then withdrawn proximally from surgical access device (100) along the second suture path, yielding the suture thread configuration shown in FIG. 8D. In particular, a first thread leg (156) of first suture thread (152) extends through access device (100) and tissue (140) along the first suture path to capture a first portion of fascia (148); a second thread leg (158) extends through access device (100) and tissue (140) along the second suture path to capture an opposed second portion of fascia (148); and an anchoring loop (160) extends between first and second thread legs (156, 158) within body cavity (150).

Figure 8E:
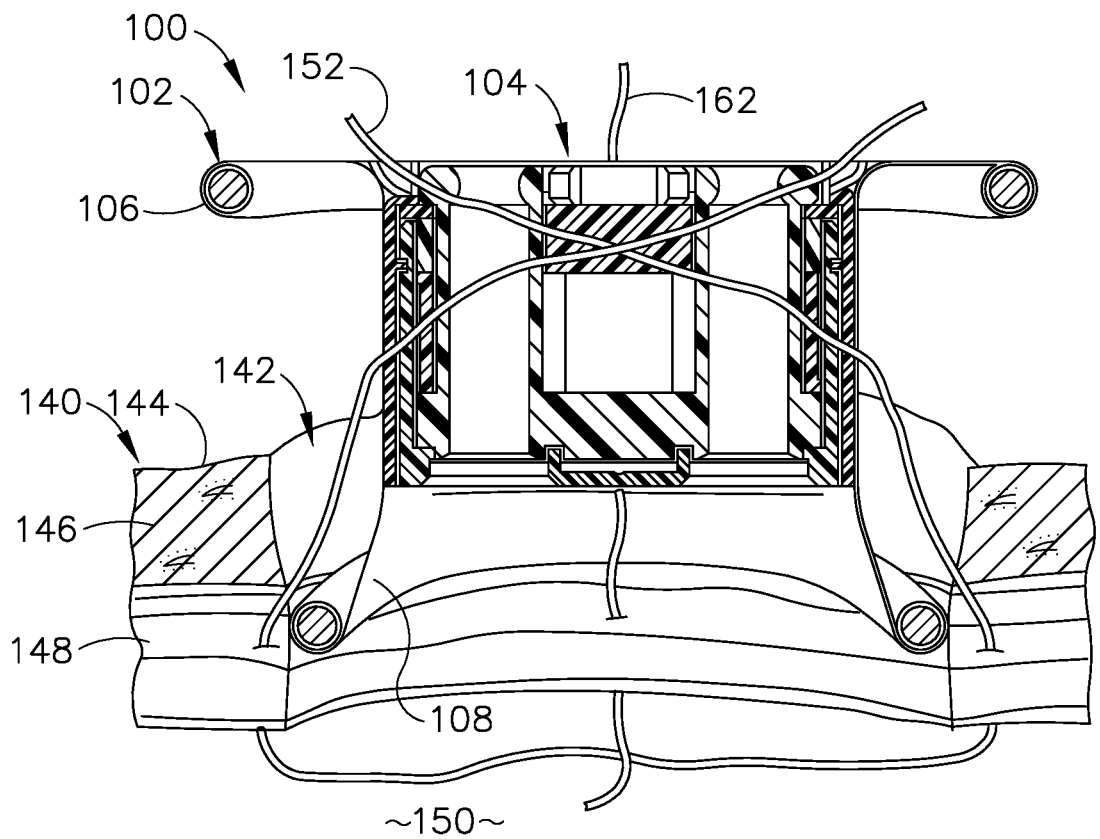
FIG. 8E depicts a schematic side sectional view of the surgical access device and tissue of FIG. 8D, showing proximal removal of the device from the tissue opening following application of a second suture thread along third and fourth suture paths extending through third and fourth needle channels of the device.

Following application of first suture thread (152) to tissue (140), a second suture thread (162) (see FIG. 8E) is applied to tissue in a similar manner. In particular, second suture thread (162) is directed through surgical access device (100) and adjacent fascia (148) along third and fourth suture paths defined by third and fourth needle channels (128), in a manner similar to that described above for first suture thread (152). The resulting configuration of first and second suture threads (152, 162) is generally seen in FIG. 8E. As shown in FIG. 8E, following application of first and second suture threads (152, 162) to tissue (140) using the integrated suture guide features of surgical access device (100), access device (100) is withdrawn proximally from tissue opening (142). Proximal withdrawal of access device (100) allows the proximally extending legs of suture threads (152, 162) to slide distally through needle channels (128), thereby freeing suture threads (152, 162) from access device (100) and yielding the suture thread configuration shown in FIG. 8F. As shown in FIG. 8E, distal flange (108) of tissue retractor (102) may elastically deform to facilitate proximal removal of access device (100) from tissue opening (142).

Figure 8F:
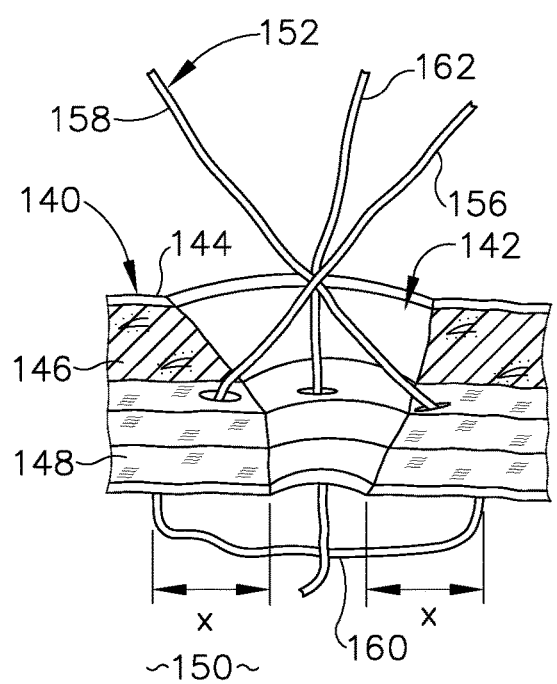
FIG. 8F depicts a schematic side sectional view of the first and second suture threads and tissue of FIG. 8E, showing the tissue opening prior to closure.

As described above, needle channels (128) are arranged uniformly within surgical access device (100), and each needle channel (128) and its corresponding suture path defines the same oblique suture path angle relative the central axis of access device (100). Accordingly, each needle channel (128) is configured to direct a respective thread leg of a suture thread (152, 162) to capture the same amount of tissue fascia (148) (referred to as "tissue bite") on its respective side of access device (100). As shown in FIG. 8F, "tissue bite" in the present context is defined by a distance (X) measured perpendicularly from the inner wall of tissue opening (142), which may coincide with the outer surface of medial body portion (110) of tissue retractor (102), to the point at which suture passer needle (136) and thus suture thread (152, 162) exits distally from tissue fascia (148) into body cavity (150). As described above, surgical access device (100) may be configured in alternative examples such that needle channels (128) are arranged non-uniformly in access device (100). For instance, needle exit ports (134) may be arranged with nonuniform axial spacing from needle entrance ports (130), and/or one or more needle channels (128) may define different suture path angles relative to the central axis of surgical access device (100). In such alternative examples, resulting tissue bite distances (X) defined by the suture paths may be nonuniform.

Figure 8G:
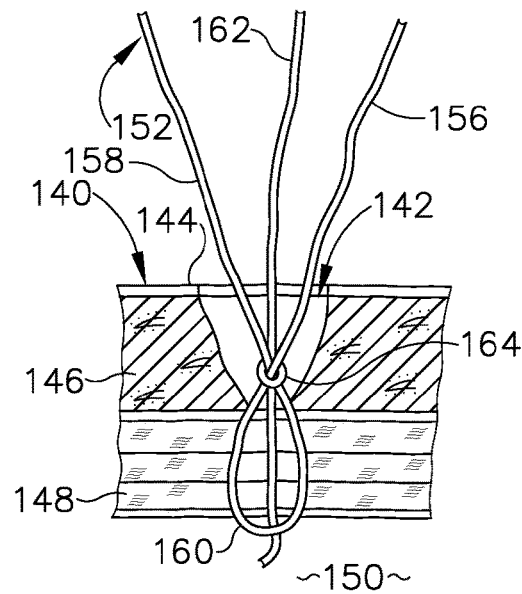
FIG. 8G depicts a schematic side sectional view of the first and second suture threads and tissue of FIG. 8F, showing closure of the tissue opening via formation of an exemplary suture knot.

As shown in FIG. 8G, the free legs of first and second suture threads (152, 162) are pulled proximally to draw together the captured portions of tissue fascia (148). The suture thread legs are then tied together to form a suture knot (164) at a location just proximally of fascia (148). Optionally, the remaining free portions of suture threads (152, 162) may be directed through fat (146) and skin (144) using suture needles, for example as shown in FIG. 4D, to create an additional "superficial" suture knot to fully close tissue opening (142) and promote optimal healing.

Figure 8H:
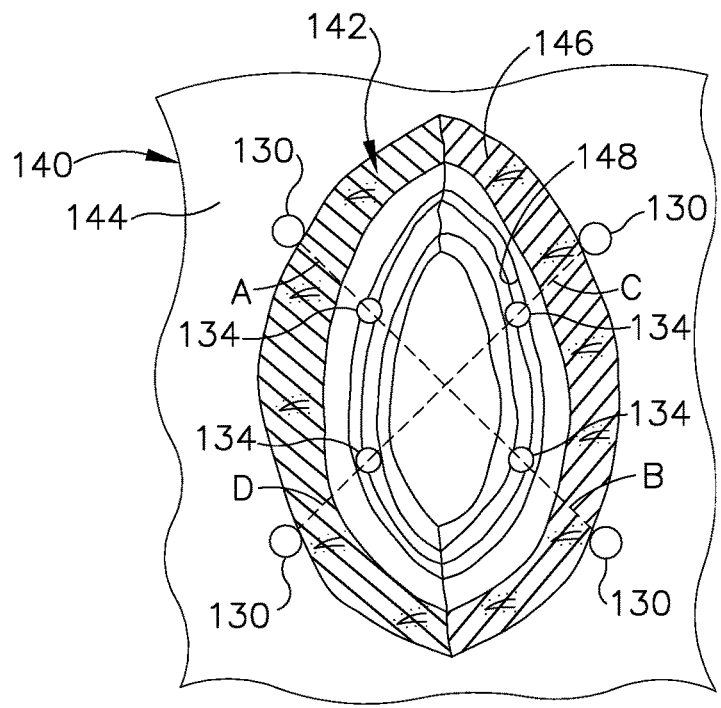
FIG. 8H depicts a schematic top elevational view of the tissue of FIG. 8F, showing an exemplary suture path pattern along which the first and second sutures are directed by the needle channels of the surgical access device of FIG. 6.

FIG. 8H schematically shows the exemplary arrangement of the first suture path (A), second suture path (B), third suture path (C), and fourth suture path (D) along which first and second suture threads (152, 162) are directed in the steps shown in FIGS. 8A-8E, described above. As shown in the present example, suitable needle channels (128) of surgical access device (100), defined by respective needle ports (130, 134), are selected such that first and second suture paths (A, B) extend in a first axial plane, and third and fourth suture paths (C, D) extend in a second axial plane that is generally perpendicular to the first axial plane. Consequently, each paring of suture paths (A, B and C, D) extends generally diagonally across tissue opening (142). In other examples, suitable needle channels (128) of surgical access device (100) may be selected to yield various other arrangements of the suture paths along which first and second suture threads (152, 162) are directed. For instance, needle channels (128) may be selected such that the first and second suture paths (A, B) for first suture thread (152) are arranged in different axial planes, and third and fourth suture paths (C, D) for second suture thread (162) are arranged in different axial planes.

C. Exemplary Suture Path Patterns

FIGS. 9A-9F show various exemplary suture path patterns along which first and second suture threads (152, 162) may be directed through surgical access device (100). In that regard, it will be understood that the suture guide features of surgical access device (100) described above may be suitably arranged as required to enable the exemplary suture path patterns of FIGS. 9A-9F.

Figure 9A:
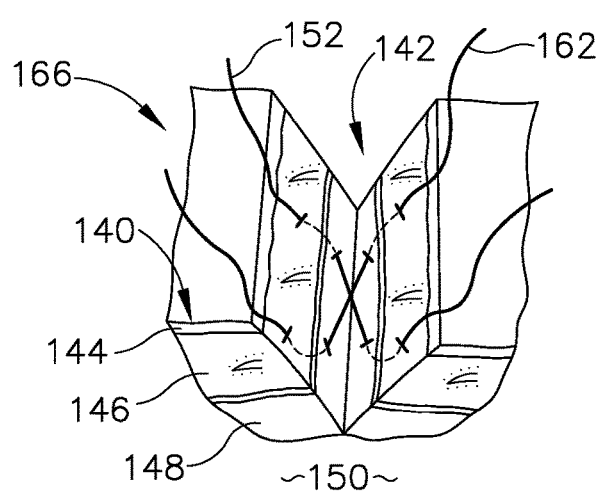
FIG. 9A depicts a schematic top perspective view showing first and second suture threads directed through tissue according to another exemplary suture path pattern for closing a tissue opening.
Figure 9B:
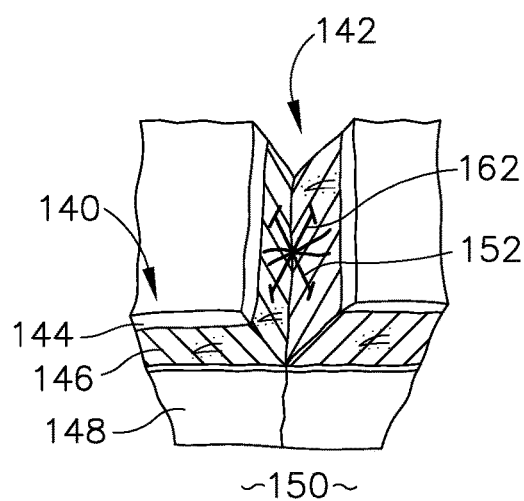
FIG. 9B depicts a schematic top perspective view showing the suture threads and tissue of FIG. 9A, showing closure of the tissue opening.

FIG. 9A shows a first exemplary suture path pattern (166) that is similar to the suture path pattern of FIG. 8H. In particular, first and second suture threads (152, 162) are applied to tissue (140) such that each suture thread (152, 162) passes through first and second portions of fascia (148) arranged on opposing sides of tissue opening (142), and such that suture threads (152, 162) intersect each other diagonally when extending across tissue opening (142) and through fascia (148). FIG. 9B shows partial closure of tissue opening (142) achieved by pulling proximally on free ends of suture threads (152, 162) applied according to suture pattern (166) of FIG. 9A.

Figure 9C:
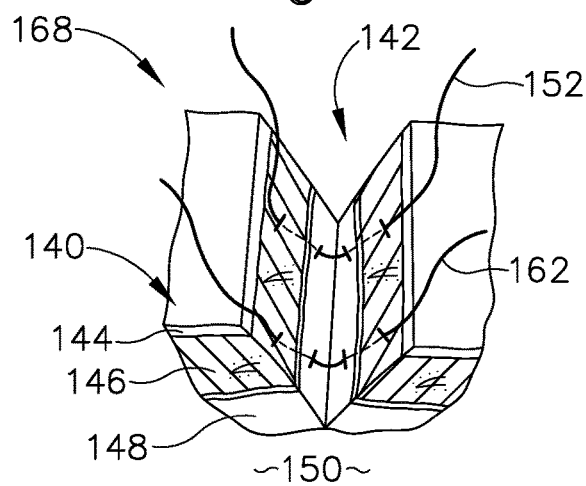
FIG. 9C depicts a schematic top perspective view showing first and second suture threads directed through tissue according to another exemplary suture path pattern for closing a tissue opening.
Figure 9D:
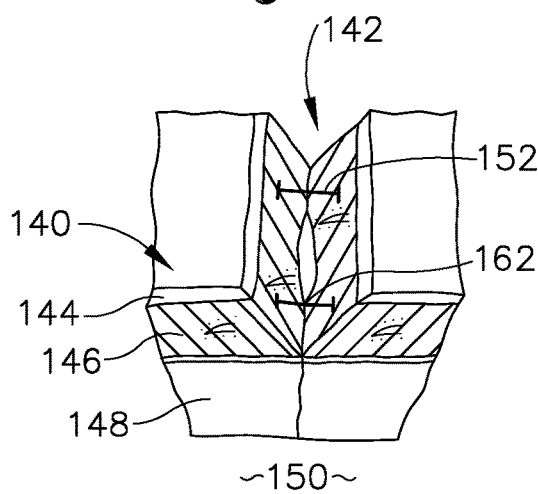
FIG. 9D depicts a schematic top perspective view showing the suture threads and tissue of FIG. 9C, showing closure of the tissue opening.

FIG. 9C shows a second exemplary suture path pattern (168) in which first and second suture threads (152, 162) are applied to tissue (140) such that each suture thread (152, 162) passes through first and second portions of fascia (148) arranged on opposing sides of tissue opening (142), and such that suture threads (152, 162) extend generally parallel to each other when extending across tissue opening (142) and through fascia (148). FIG. 9D shows partial closure of tissue opening (142) achieved by pulling proximally on free ends of suture threads (152, 162) applied accord to suture pattern (168) of FIG. 9C.

Figure 9E:
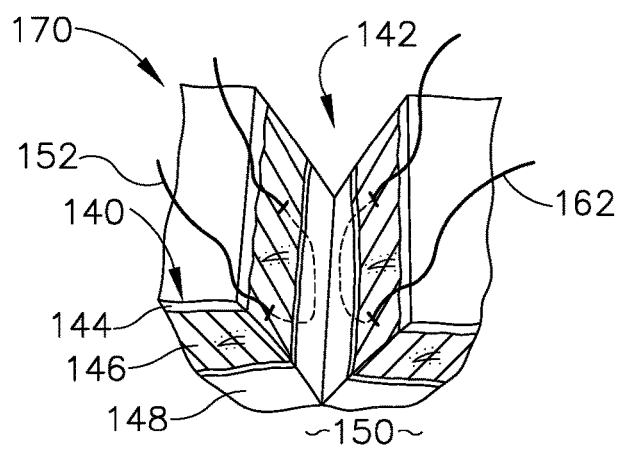
FIG. 9E depicts a schematic top perspective view showing first and second suture threads directed through tissue according to another exemplary suture path pattern for closing a tissue opening.
Figure 9F:
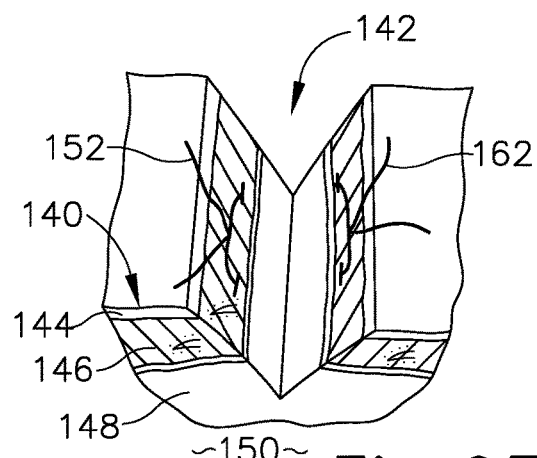
FIG. 9F depicts a schematic top perspective view showing the suture threads and tissue of FIG. 9E, showing partial closure of the tissue opening.

FIG. 9E shows a third exemplary suture path pattern (170) in which first and second suture threads (152, 162) are applied to tissue (140) such that first suture thread (152) passes twice through a first portion of fascia (148) arranged on a first side of tissue opening (142), and second suture thread passes twice through a second portion of fascia (148) arranged on a second side of an opposed second side of tissue opening (142). FIG. 9F shows partial closure of tissue opening (142) achieved by securing together first and second thread legs of first suture thread (152) extending from the first portion of fascia (148), and securing together first and second thread legs of second suture thread (162) extending from the second portion of fascia (148). Though not shown, threads legs of first suture thread (152) may then be tied together with thread legs of second suture thread (162) to thereby further close tissue opening (142).

III. EXEMPLARY SINGLE-INCISION SURGICAL ACCESS DEVICE HAVING INSERT WITH CENTRAL CHANNEL

A. Exemplary Single-Incision Surgical Access Device

Figure 10:
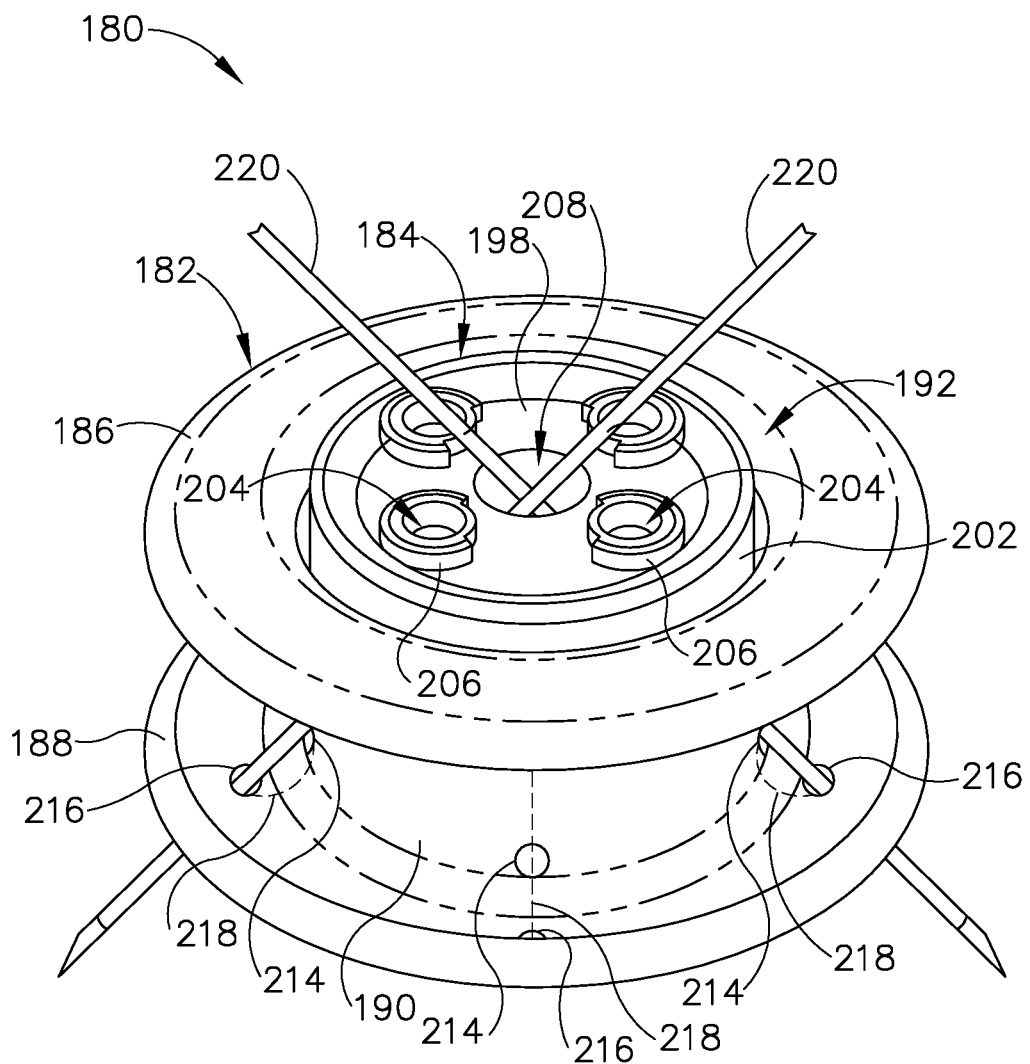
FIG. 10 depicts a perspective view of another exemplary single-incision surgical access device, showing a suture passer needle directed through first and second needle channels of the device.
Figure 11:
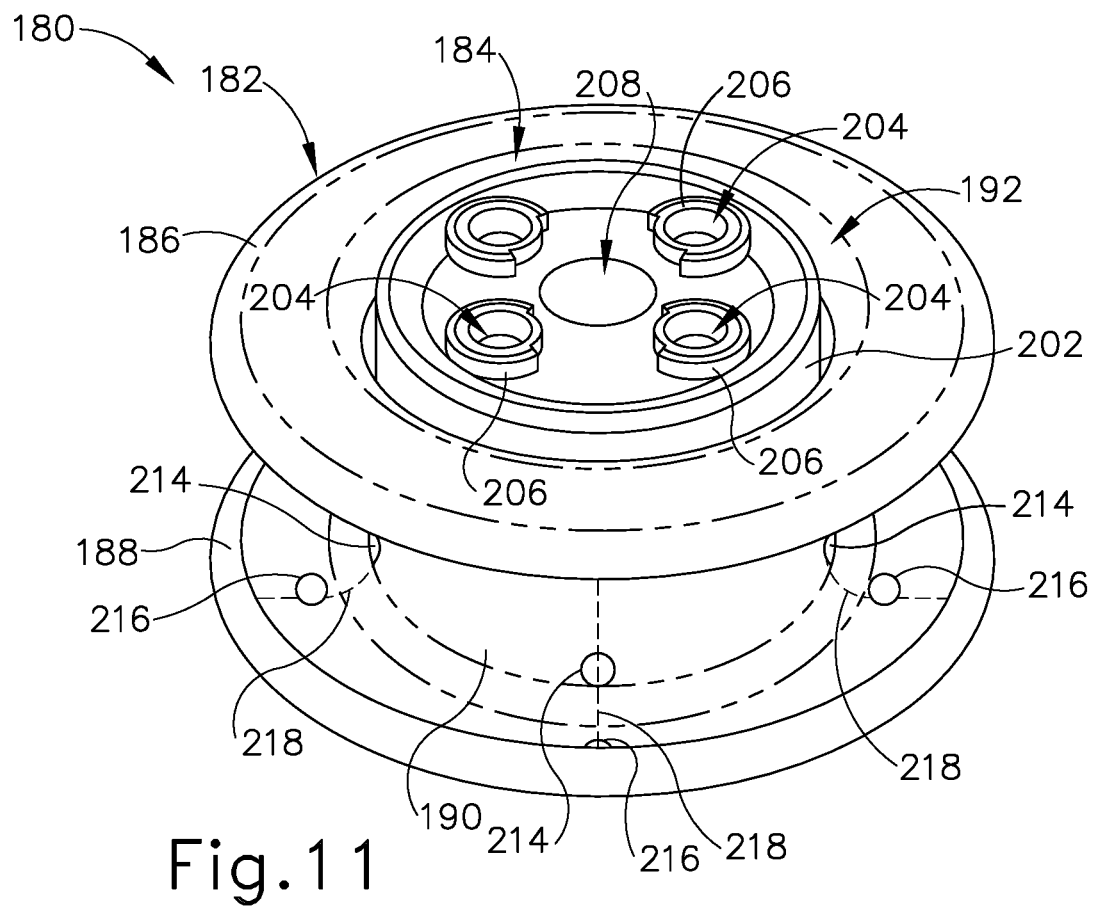
FIG. 11 depicts another perspective view of the surgical access device of FIG. 10.
Figure 12:
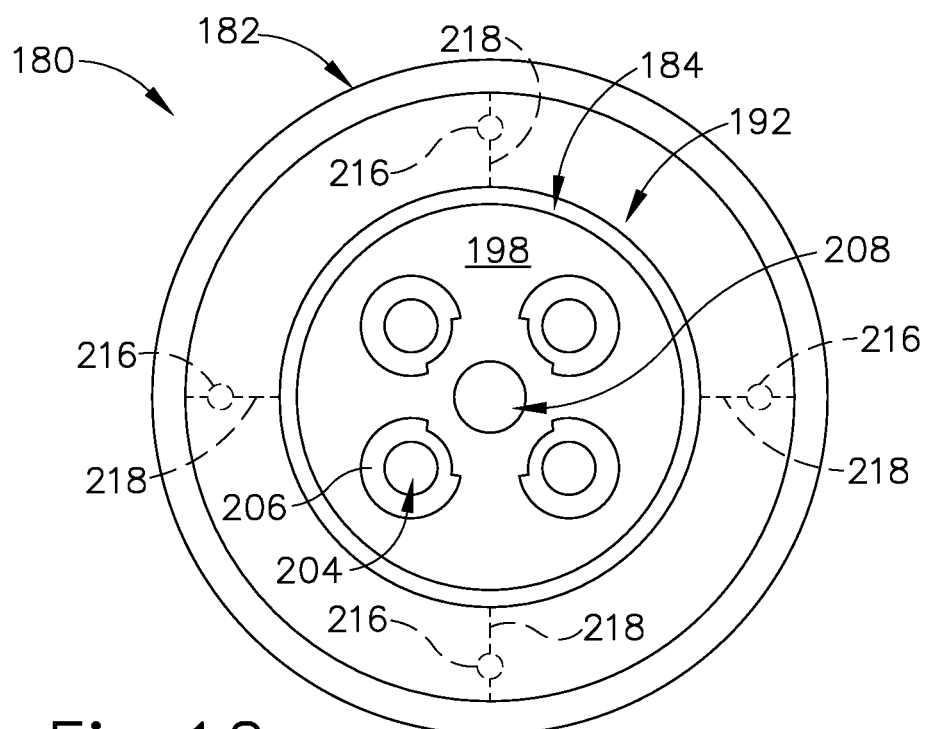
FIG. 12 depicts a top elevational view of the surgical access device of FIG. 10.

FIGS. 10-12 show another exemplary single-incision surgical access device (180) having integrated suture guide features configured to facilitate closure of a tissue opening in which access device (180) is positioned for a surgical procedure. Surgical access device (180) is similar to surgical access device (100) described above except as otherwise described in detail below.

Figure 13A:
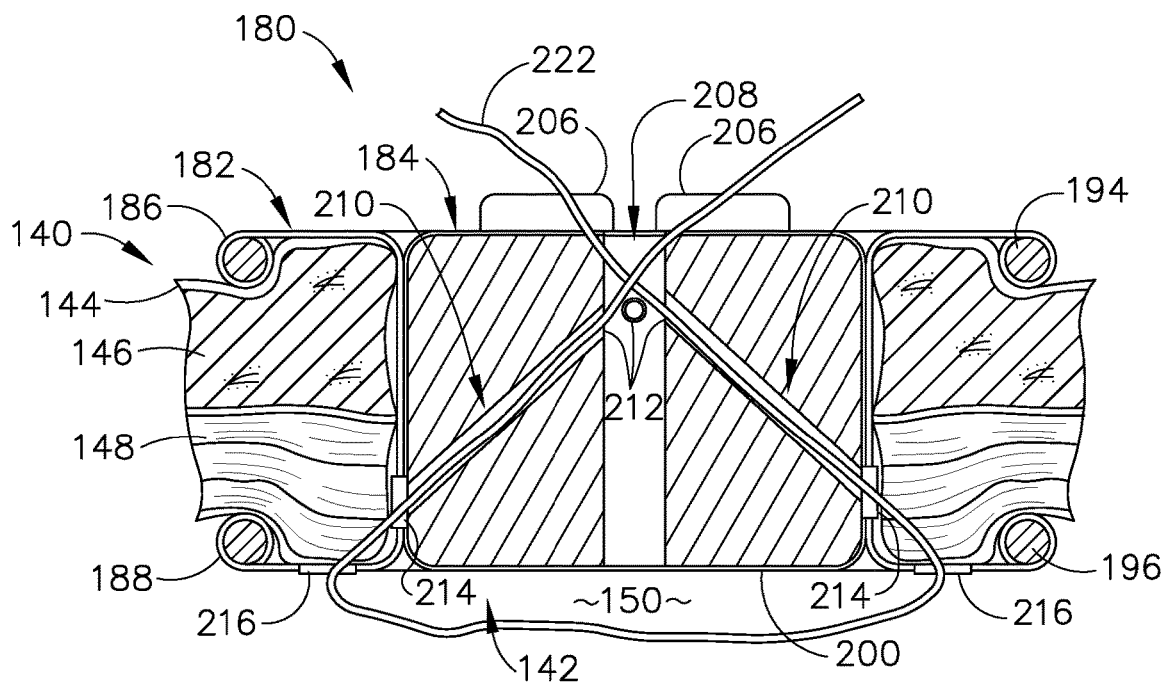
FIG. 13A depicts a schematic side sectional view of the surgical access device of FIG. 10, showing the device positioned within a tissue opening and a suture thread directed along first and second suture paths extending through first and second needle channels of the device and adjacent tissue.

Similar to surgical access device (100), surgical access device (180) includes a tissue retractor (182) and an insert (184) supported within a central region of tissue retractor (182). More specifically, tissue retractor (182) includes a flexible annular body having a proximal flange (186), a distal flange (188), a medial body portion (190) extending axially between proximal and distal flanges (186, 188), and a central passage (192) extending axially through the annular body. Insert (184) is supported within central passage (192). Additionally, as shown in FIG. 13A, an outer lip of proximal flange (186) houses a proximal resilient ring (194) and an outer lip of distal flange (188) houses a distal resilient ring (196). Similar to surgical access device (100), surgical access device (180) may further include an insufflation port (not shown) and one or more sealing elements (not shown) configured to maintain insufflation during a surgical procedure.

Similar to insert (104) of surgical access device (100), insert (184) of access device (180) may be configured as a rigid assembly defining a generally cylindrical body having a proximal face (198), a distal face (200) (see FIG. 13A), a sidewall (202), and a plurality of surgical instrument channels (204) extending axially through the cylindrical body and opening to proximal and distal faces (198, 200). In the present example, insert (184) includes four instrument channels (204) arranged circumferentially with uniform spacing. Each surgical instrument channel (204) is provided with an instrument entry guide member (206), shown in the form of a ring structure, arranged on proximal face (198) and configured to guide insertion of a surgical instrument into the entrance end of the instrument channel (204). Unlike insert (104), insert (184) includes a central channel (208) extending axially therethrough along the central axis of access device (180) and opening to proximal and distal faces (198, 200) of insert (184).

As best shown in FIG. 13A, surgical access device (180) further includes four circumferentially arranged needle channels (210) extending distally through access device (180) and obliquely relative to the central axis. A proximal end of each needle channel (210) opens to central channel (208) to thereby define a respective needle entrance port (212). Accordingly, needle entrance ports (212) are accessible via central channel (208). A distal end of each needle channel (210) exits through a needle exit port (214) arranged on a distal portion of medial body portion (190) of tissue retractor (182). Surgical access device (180) further includes a plurality of flange ports (216) arranged on a radially extending portion of distal flange (188) of tissue retractor (182). Each flange port (216) aligns with a respective needle exit port (214) and cooperates with the corresponding needle channel (210) to define an oblique suture path along which a suture passer needle and a suture thread may be directed, as described below.

Similar to surgical access device (100) described above, the suture guide features of surgical access device (180) are arranged uniformly in circumferential, axial, and radial directions such that each suture path defined by a needle channel (210) and its respective flange port (216) defines the same suture path angle relative to the central axis of access device (180). Unlike access device (100), needle entrance and exit ports (212, 214) and flange ports (216) of access device (180) are circumferentially offset from surgical instrument channels (204). Accordingly, needle channels (210) pass distally between instrument channels (204) rather than through instrument channels (204). Other versions of surgical access device (180) may include needle ports (212, 214) and flange ports (216) arranged in various other quantities and configurations, which may define a variety of suture path angles.

As shown in FIGS. 10 and 11, tissue retractor (182) of the present example further includes a plurality of perforation lines (218) configured to facilitate release of suture threads from surgical access device (180) during a wound closure procedure. Each perforation line (218) is positioned in alignment with a respective needle exit port (214) and a corresponding flange port (216). In particular, each perforation line (218) extends radially inwardly from a flange port (216), and proximally along medial body portion (190) to join with the respective needle exit port (214). As shown in the present example, each perforation line (218) may extend proximally beyond needle exit port (214) and/or radially outwardly beyond flange port (216).

As best shown in FIG. 12, perforation lines (218) divide a distal portion of tissue retractor (182) into a plurality of circumferential sections. In the present example, perforation lines (218) define four circumferential sections (or quadrants) of tissue retractor (182). In use, perforation lines (218) are configured to rupture to thereby separate adjacent circumferential sections from one another. Advantageously, this enables suture threads to be easily released from tissue retractor (182) during a wound closure procedure, for example as described below.

Figure 13B:
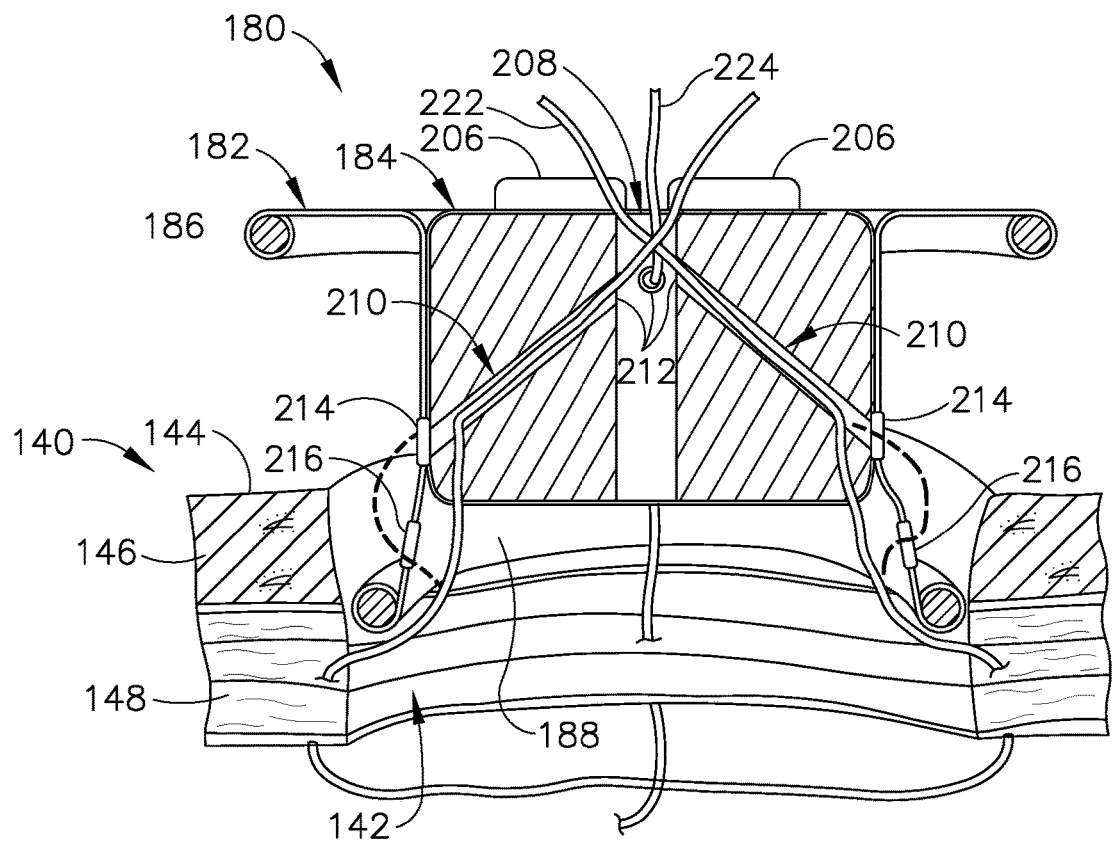
FIG. 13B depicts a schematic side sectional view of the surgical access device and tissue of FIG. 13A, showing proximal removal of the device from the tissue opening following application of a second suture thread along third and fourth suture paths extending through third and fourth needle channels of the device and adjacent tissue.

B. Exemplary Wound Closure Procedure Using Single-Incision Surgical Access Device Having Insert with Central Channel FIGS. 13A and 13B show steps of an exemplary procedure for suturing closed a tissue opening (142) formed in tissue (140) using single-incision surgical access device (180) as a wound closure device. The steps of the present wound closure procedure are similar to those described above in connection with the wound closure procedure shown in FIGS. 8A-8G, except as otherwise described in detail below.

FIG. 13A shows surgical access device (180) positioned within tissue opening (142), and a first suture thread (222) directed through access device (180) and adjacent portions of tissue fascia (148) along first and second suture paths. It will be understood that first suture thread (222) may be directed through access device (180) and fascia (148) using any suitable suture passer needle, such as suture passer needle (220). As described above, needle entrance ports (212) open to central channel (208) of insert (184), such that suture passer needle (220) accesses each needle entrance port (212) via a proximal opening of central channel (208). Suture passer needle (220) directs first suture thread (222) along a first suture path extending through a first needle channel (210), an adjacent first portion of tissue fascia (148), and a corresponding first flange port (216), into body cavity (150). Suture passer needle (220) further directs first suture thread (222) along a second suture path extending through an opposed second needle channel (210), an adjacent second portion of tissue fascia (148), and a corresponding second flange port (216), yielding the suture thread configuration shown in FIG. 13A. Similar steps are then repeated for a second suture thread (224) directed along third and fourth suture paths through third and fourth portions of tissue fascia (148).

Following application of first and second suture threads (222, 224) to tissue (140), surgical access device (180) is withdrawn proximally from tissue opening (142), as shown in FIG. 13B. Pulling access device (180) proximally from tissue opening (142) causes suture threads (222, 224) to tighten radially inwardly against tissue retractor (182) and thereby rupture retractor (182) along perforation lines (218). Alternatively, or in combination, a surgeon may manually tear tissue retractor (218) along one or more perforation lines (218) by reaching distally through tissue opening (142), for example with a surgical instrument. Rupturing and/or tearing of perforation lines (218) operates to release suture threads (222, 224) from distal flange (188), including flange ports (216), thereby permitting suture threads (222, 224) to pass beneath distal flange (188) as shown in FIG. 13B. Repositioning suture threads (222, 224) relative to tissue retractor (182) in this manner facilitates proximal withdrawal of access device (180) from tissue opening (142) while ensuring that suture threads (222, 224) remain securely positioned within captured portions of fascia (148). As surgical access device (180) is fully withdrawn from tissue opening (142), suture threads (222, 224) fully release from access device (180), thereby yielding a suture thread configuration similar to that shown in FIG. 8F, described above. One or more suture knots (not shown) may then be formed to fully close tissue opening (142), as described above in connection with FIG. 8G.

IV. EXEMPLARY SINGLE-INCISION SURGICAL ACCESS DEVICE HAVING INSERT WITH NEEDLE ENTRANCE PORTS IN PROXIMAL FACE

A. Exemplary Single-Incision Surgical Access Device

Figure 14:
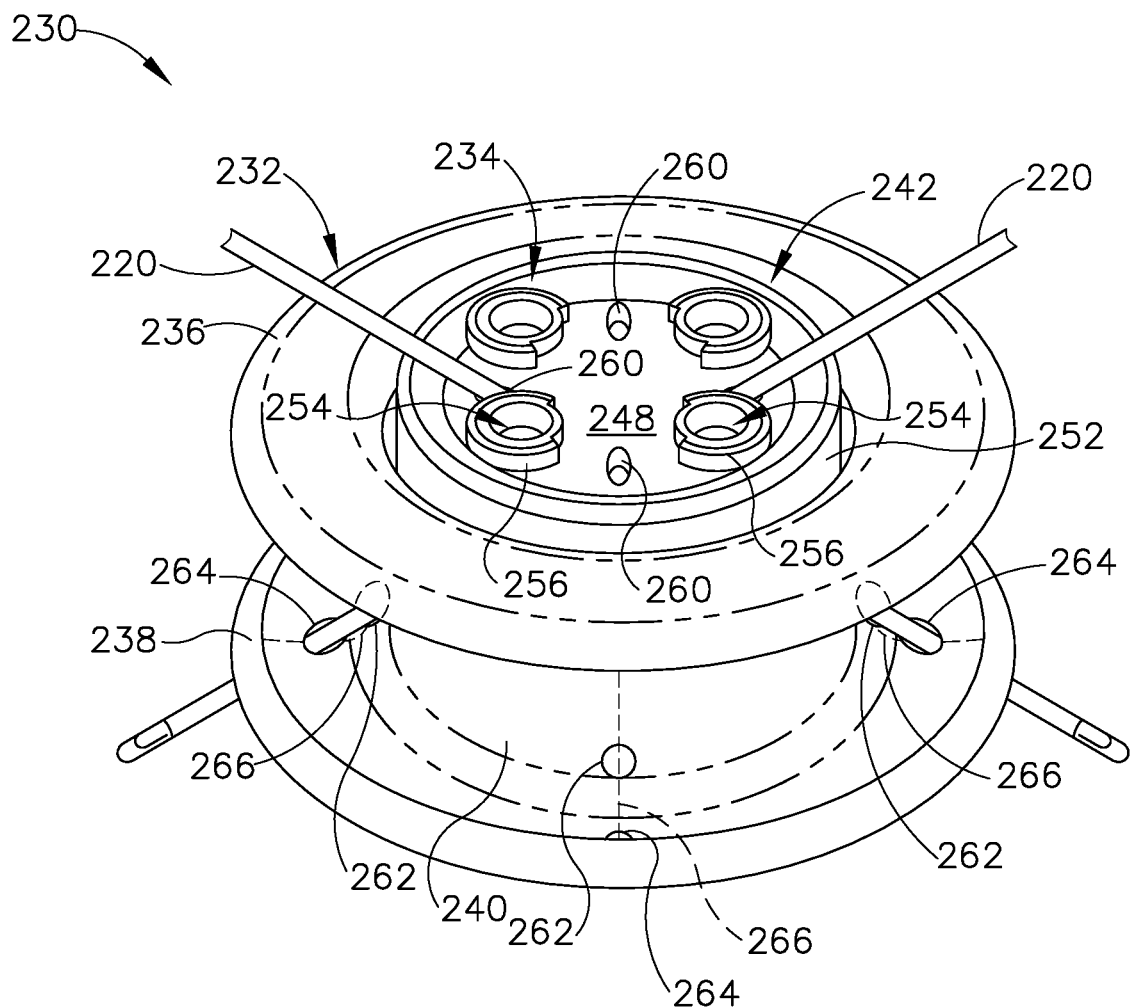
FIG. 14 depicts a perspective view of another exemplary single-incision surgical access device, showing a suture passer needle directed through first and second needle channels of the device.
Figure 15:
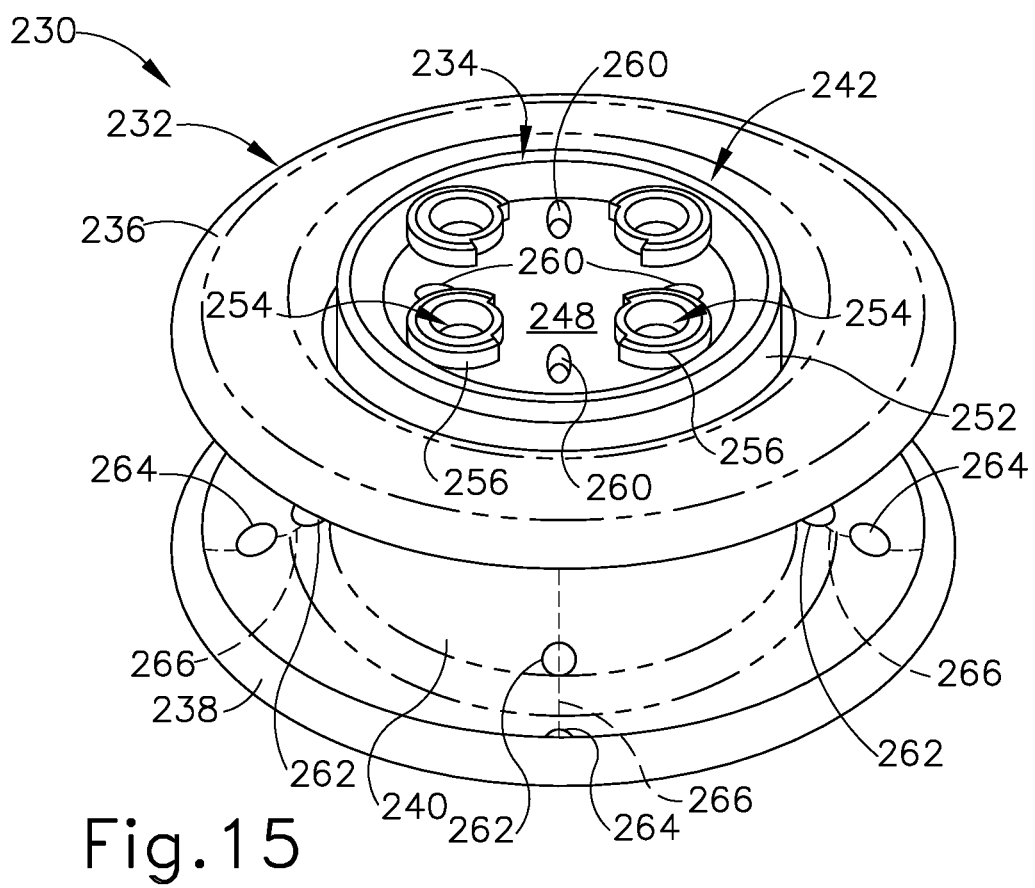
FIG. 15 depicts another perspective view of the surgical access device of FIG. 14.
Figure 16:
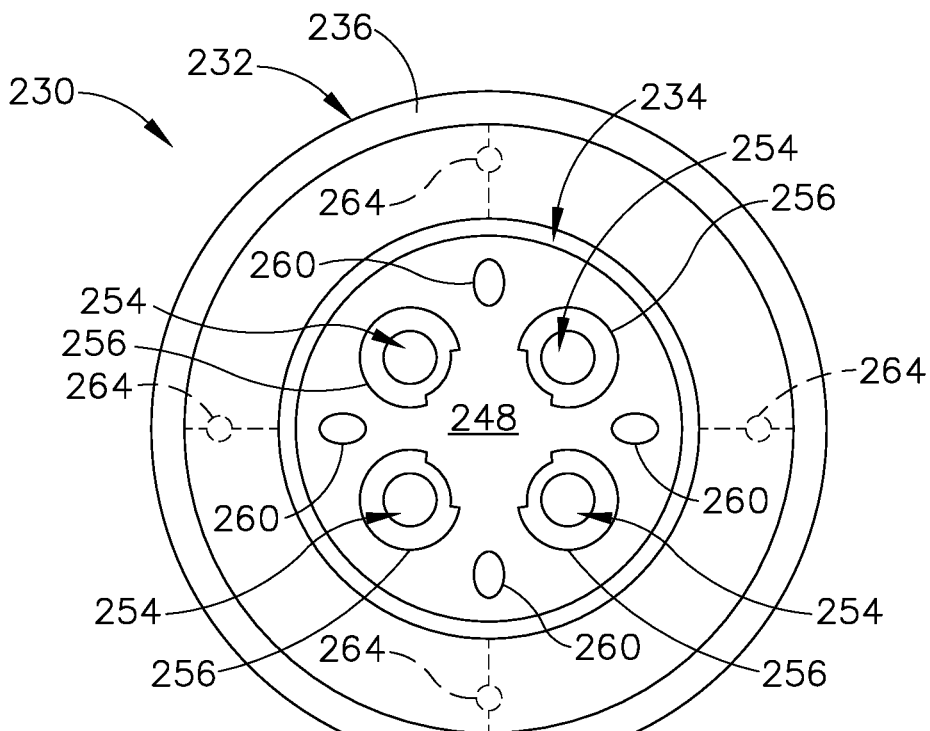
FIG. 16 depicts a top elevational view of the surgical access device of FIG. 14.

FIGS. 14-16 show another exemplary single-incision surgical access device (230) having integrated suture guide features configured to facilitate closure of a tissue opening in which access device (230) is positioned for a surgical procedure. Surgical access device (230) is similar to surgical access device (180) described above, except as otherwise described in detail below.

Figure 17A:
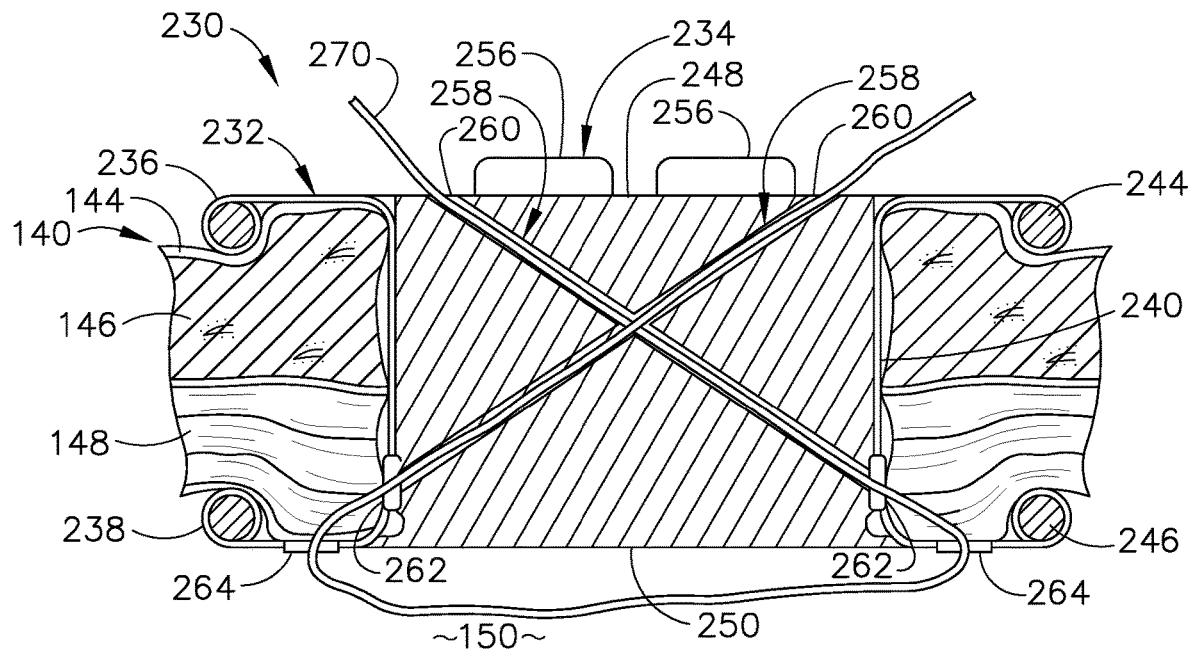
FIG. 17A depicts a schematic side sectional view of the surgical access device of FIG. 14, showing the device positioned within a tissue opening and a suture thread directed along first and second suture paths extending through first and second needle channels of the device and adjacent tissue.

Similar to surgical access device (180), surgical access device (230) includes a tissue retractor (232) and an insert (234) supported within a central region of tissue retractor (232). More specifically, tissue retractor (232) includes a flexible annular body having a proximal flange (236), a distal flange (238), a medial body portion (240) extending axially between proximal and distal flanges (236, 238), and a central passage (242) extending axially through the annular body. Insert (234) is supported within central passage (242). Additionally, as shown in FIG. 17A, an outer lip of proximal flange (236) houses a proximal resilient ring (244), and an outer lip of distal flange (238) houses a distal resilient ring (246). Surgical access device (180) may further include an insufflation port (not shown) and one or more sealing elements (not shown) configured to maintain insufflation during a surgical procedure.

Similar to insert (184) of surgical access device (180), insert (234) may be configured as a rigid assembly defining a generally cylindrical body having a proximal face (248), a distal face (250), a sidewall (252), and a plurality of surgical instrument channels (254) extending axially through the cylindrical body and opening to proximal and distal faces (248, 250). In the present example, insert (234) includes four instrument channels (254) arranged circumferentially with uniform spacing. Each surgical instrument channel (254) is provided with an instrument entry guide member (256), shown in the form of a ring structure, arranged on proximal face (248) and configured to guide insertion of a surgical instrument into the entrance end of the instrument channel (254). Unlike insert (184), insert (234) of the present example omits central channel (208), though in other versions a similar central channel may be provided.

As shown in FIG. 17A, surgical access device (230) further includes four circumferentially arranged needle channels (258) extending distally through access device (230) and obliquely relative to the central axis thereof. As shown in FIGS. 14-16, a proximal end of each needle channel (258) is defined by a needle entrance port (260) formed in proximal face (248) of insert (234), and a distal end of each needle channel (258) is defined by a needle exit port (262) arranged on a distal portion of medial body portion (240) of tissue retractor (232). Like surgical access device (180), access device (230) further includes a plurality of flange ports (264) arranged on a radially extending portion of distal flange (238) of tissue retractor (232). Access device (230) also includes a plurality of perforation lines (266) arranged circumferentially in a distal portion of tissue retractor (232), similar to perforation lines (218) described above.

Similar to surgical access device (180), the suture guide features of surgical access device (230) are arranged uniformly in circumferential, axial, and radial directions such that each suture path defined by a needle channel (258) and its respective flange port (264) defines the same suture path angle relative to the central axis of access device (180). Similar to access device (180), needle entrance and exit ports (260, 262) and flange ports (264) of access device (230) are circumferentially offset from surgical instrument channels (254). Accordingly, needle channels (258) pass distally between instrument channels (204) rather than through instrument channels (254). Other versions of surgical access device (230) may include needle ports (260, 262) and flange ports (264) arranged in various other quantities and configurations, which may define a variety of suture path angles.

Figure 17B:
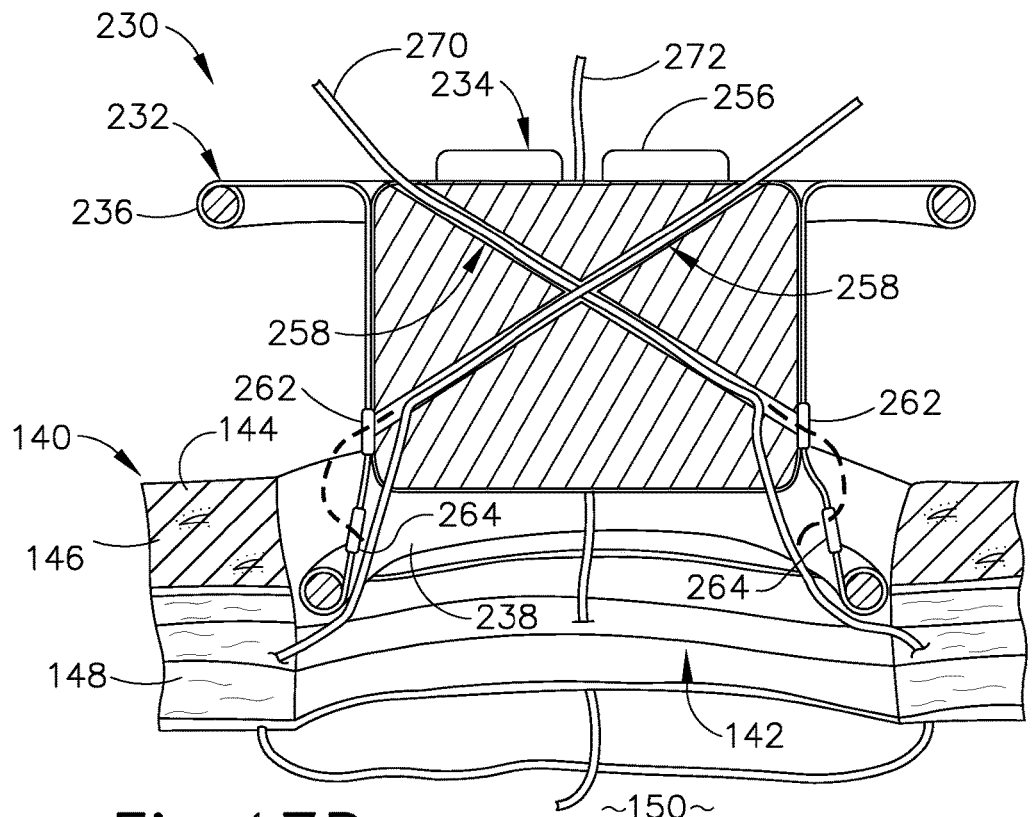
FIG. 17B depicts a schematic side sectional view of the surgical access device and tissue of FIG. 17A, showing proximal removal of the device from the tissue opening following application of a second suture thread along third and fourth suture paths extending through third and fourth needle channels of the device and adjacent tissue.

B. Exemplary Wound Closure Procedure Using Single-Incision Surgical Access Device Having Insert with Needle Entrance Ports in Proximal Face FIGS. 17A and 17B show steps of an exemplary procedure for suturing closed a tissue opening (142) formed in tissue (140) using single-incision surgical access device (230) as a wound closure device for applying first and second suture threads (270, 272). As will be readily apparent to one of ordinary skill in the art, the wound closure steps illustrated in FIGS. 17A and 17B in connection with surgical access device (230) are substantially similar to the wound closure steps described above in connection with FIGS. 13A and 13B and surgical access device (180).

Figure 21A:
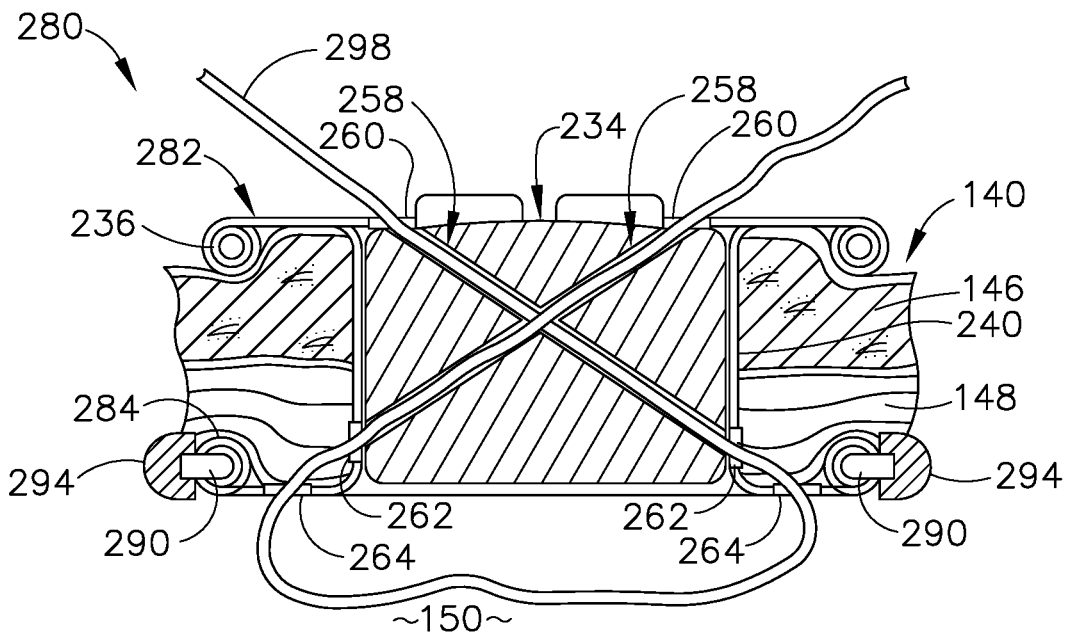
FIG. 21A depicts a schematic side sectional view of the surgical access device of FIG. 18, showing the device positioned within a tissue opening and a suture thread directed along first and second suture paths extending through first and second needle channels of the device and adjacent tissue.
Figure 21B:
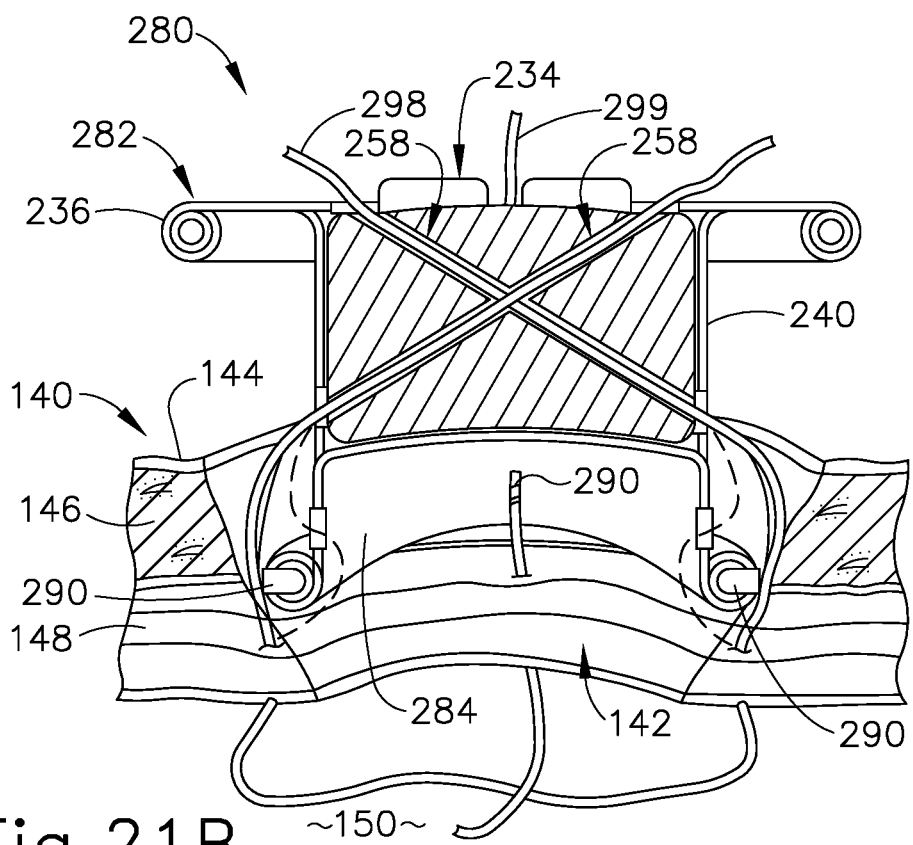
FIG. 21B depicts a schematic side sectional view of the surgical access device and tissue of FIG. 21A, showing proximal removal of the device from the tissue opening following application of a second suture thread along third and fourth suture paths extending through third and fourth needle channels of the device and adjacent tissue, and following decoupling of adjacent resilient ring segments and separation of adjacent distal flange portions as shown in FIG. 20B.

In particular, first suture thread (270) is directed along first and second suture paths extending through first and second needle channels (258) and corresponding flange ports (264) of surgical access device (230), and adjacent first and second portions of tissue fascia (148). Additionally, second suture thread (272), shown in FIG. 21B, is directed along third and fourth suture paths extending through first and second needle channels (258) and corresponding flange ports (264) of access device (230), and adjacent third and fourth portions of tissue fascia (148). These steps differ from those described in connection with surgical access device (180) shown in FIGS. 13A and 13B in that suture threads (270, 272) are directed into needle channels (258) of access device (230) via needle entrance ports (260) arranged in proximal face (248) of insert (234), rather than via a central channel of insert (234). Surgical access device (230) may then be withdrawn from tissue opening (142), and suture threads (270, 272) may be tied, in a manner similar to that described above in connection with surgical access device (180).

V. EXEMPLARY SINGLE-INCISION SURGICAL ACCESS DEVICE HAVING SEGMENTED DISTAL RING

A. Exemplary Single-Incision Surgical Access Device

FIGS. 18-20B show another exemplary single-incision surgical access device (280) having integrated suture guide features configured to facilitate closure of a tissue opening in which access device (280) is positioned for a surgical procedure. Surgical access device (280) is similar to surgical access device (230) described above, except as otherwise described in detail below. In that regard, like reference numerals in FIGS. 18-20B refer to like features described above in connection with FIGS. 14-16.

Figure 18:
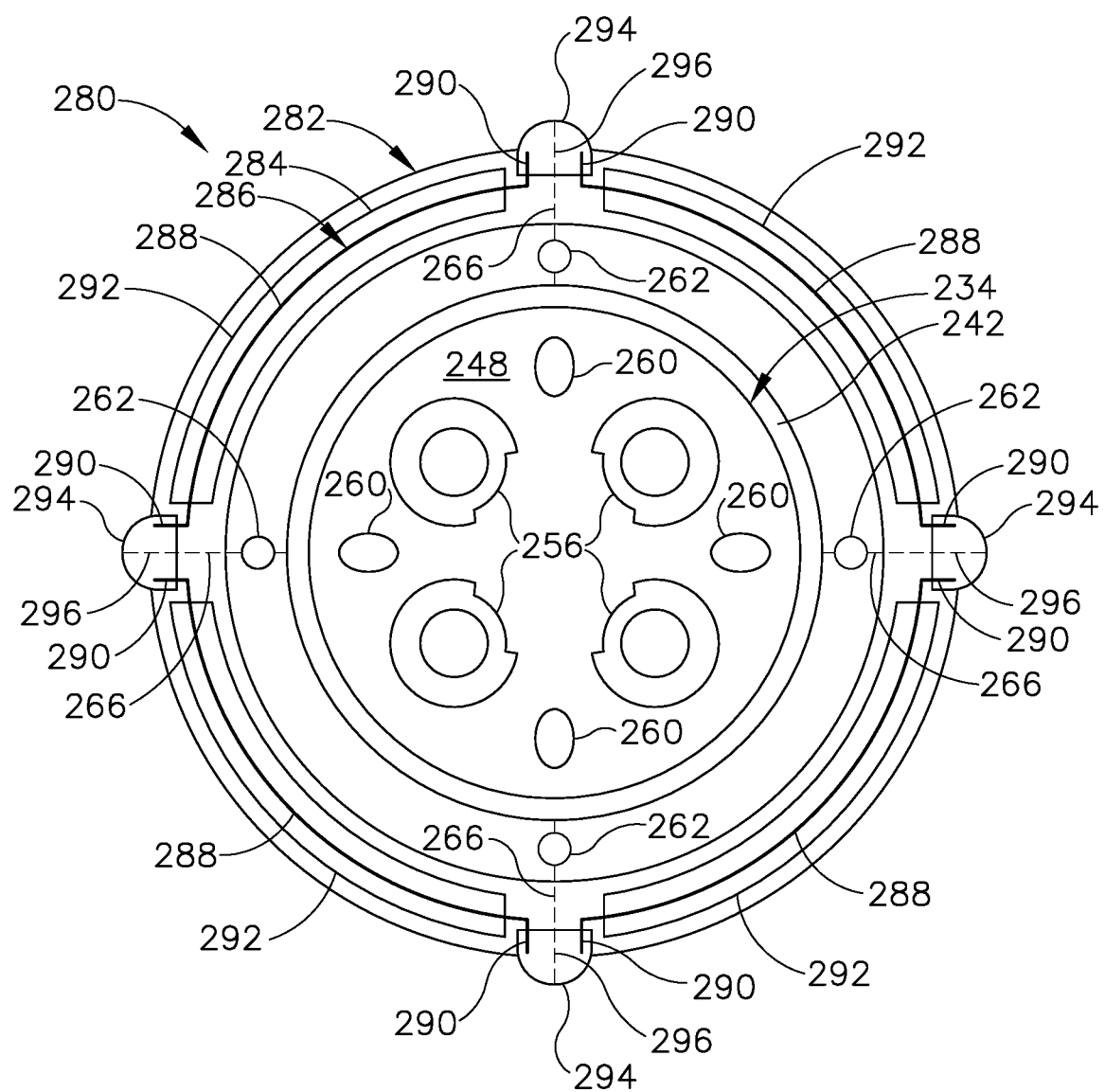
FIG. 18 depicts a schematic top elevational view of another exemplary single-incision surgical access device, wherein a proximal flange of a tissue retractor of the device is omitted to show details of a distal flange of the tissue retractor.

Surgical access device (280) differs from surgical access device (230) in that tissue retractor (282) of access device (280) includes a distal flange (284) housing a segmented distal resilient ring (286) that is divided into a plurality of independent circumferential ring segments (288). As shown in FIG. 18, each ring segment (288) includes a pair of end legs (290) projecting radially outwardly from the two ends of ring segment (288) and through an outer surface of distal flange (284). Ring segments are arranged circumferentially such that each confronting pair of end legs (290) of adjacent ring segments (288) is aligned with a perforation line (266) of tissue retractor (282). More specifically, each confronting pair of end legs (290) spans a respective perforation line (266) such that perforation line (266) extends radially between a circumferential gap formed between the confronting end legs (290). As shown in FIG. 19, an arcuate body portion of each ring segment (288) extending between its end legs (290) is housed within a tubular member (292), which in turn is housed within distal flange (284). Ring segments (288) may be formed of any suitable resilient material, such as nitinol, for example. Additionally, tubular members (292) may be formed of any suitable polymeric material, such as silicone, for example. In exemplary configurations, distal flange (284) may be formed as an overmold assembly.

Surgical access device (280) further includes a plurality of coupling members shown in the form of caps (294) configured to couple together each confronting pair of end legs (290) of adjacent ring segments (288). As shown in FIGS. 18 and 20A-20B, each confronting pair of end legs (290) is received within a respective cap (294). Each cap (294) includes a perforation line (296) extending radially therethrough and diving cap (294) into first and second side portions, each side portion receiving a respective ring segment end leg (290). As shown in FIGS. 20A and 20B, each cap (294) is configured to be torn along its perforation line (296) to thereby decouple adjacent ring segments (288) from one another. Accordingly, when tissue retractor (282) is also torn along its corresponding perforation line (266), a suture thread (298) extending through the corresponding flange port (264) may be freed from distal flange (284) and redirected over the top of distal flange (284). As described below in connection with FIG. 21B, this feature of surgical access device (280) provides advantages during a wound closure procedure. It will be appreciated that segmented distal ring (286) and caps (294) may be incorporated into the construction of any of the other exemplary single-incision surgical access devices described herein.

B. Exemplary Wound Closure Procedure Using Single-Incision Surgical Access Device Having Segmented Distal Ring FIGS. 21A and 21B show steps of an exemplary procedure for suturing closed a tissue opening (142) formed in tissue (140) using single-incision surgical access device (280) as a wound closure device for applying first and second suture threads (298, 299). Those of ordinary skill in the art will appreciate that the steps of the present wound closure method are similar to those described above in connection with surgical access devices (180, 230), except as otherwise described below.

FIG. 21A shows a first suture thread (298) after having been directed along first and second suture paths extending through first and second needle channels (258) and corresponding flange ports (264) of surgical access device (280), and adjacent first and second portions of tissue fascia (148). A second suture thread (299), shown in FIG. 21B, is then directed along third and fourth suture paths extending through first and second needle channels (258) and corresponding flange ports (264) of surgical access device (280), and adjacent third and fourth portions of tissue fascia (148). Similar to wound closure methods described above in connection with surgical access devices (180, 230), access device (280) is pulled proximally from tissue opening (142). This proximal movement causes suture threads (298, 299) to exert a radially outwardly directed force against distal flange (284) and thereby rupture retractor perforation lines (266) as well as cap perforation lines (296). A surgeon may assist this process by reaching distally through tissue opening (142), for example with a surgical instrument, and manually tearing one or more perforation lines (266, 296). Rupturing of perforation lines (266, 296) operates to separate ring segments (288) from one another and thereby free suture threads (298, 299) from flange ports (264) and enable suture threads (298, 299) to be repositioned over the top of distal flange (284), as shown in FIG. 21B.

Repositioning suture threads (298, 299) relative to tissue retractor (282) in the manner shown in FIG. 21B facilitates proximal withdrawal of surgical access device (280) from tissue opening (142) while ensuring that suture threads (298, 299) remain securely positioned within captured portions of fascia (148). As surgical access device (280) is fully withdrawn from tissue opening (142), suture threads (298, 299) fully release from access device (280), thereby yielding a suture thread configuration similar to that shown in FIG. 8F, described above. One or more suture knots (not shown) may then be formed to fully close tissue opening (142), as described above in connection with FIG. 8G.

VI. EXEMPLARY SINGLE-INCISION SURGICAL ACCESS DEVICES HAVING PROXIMAL HOUSING

Figure 22:
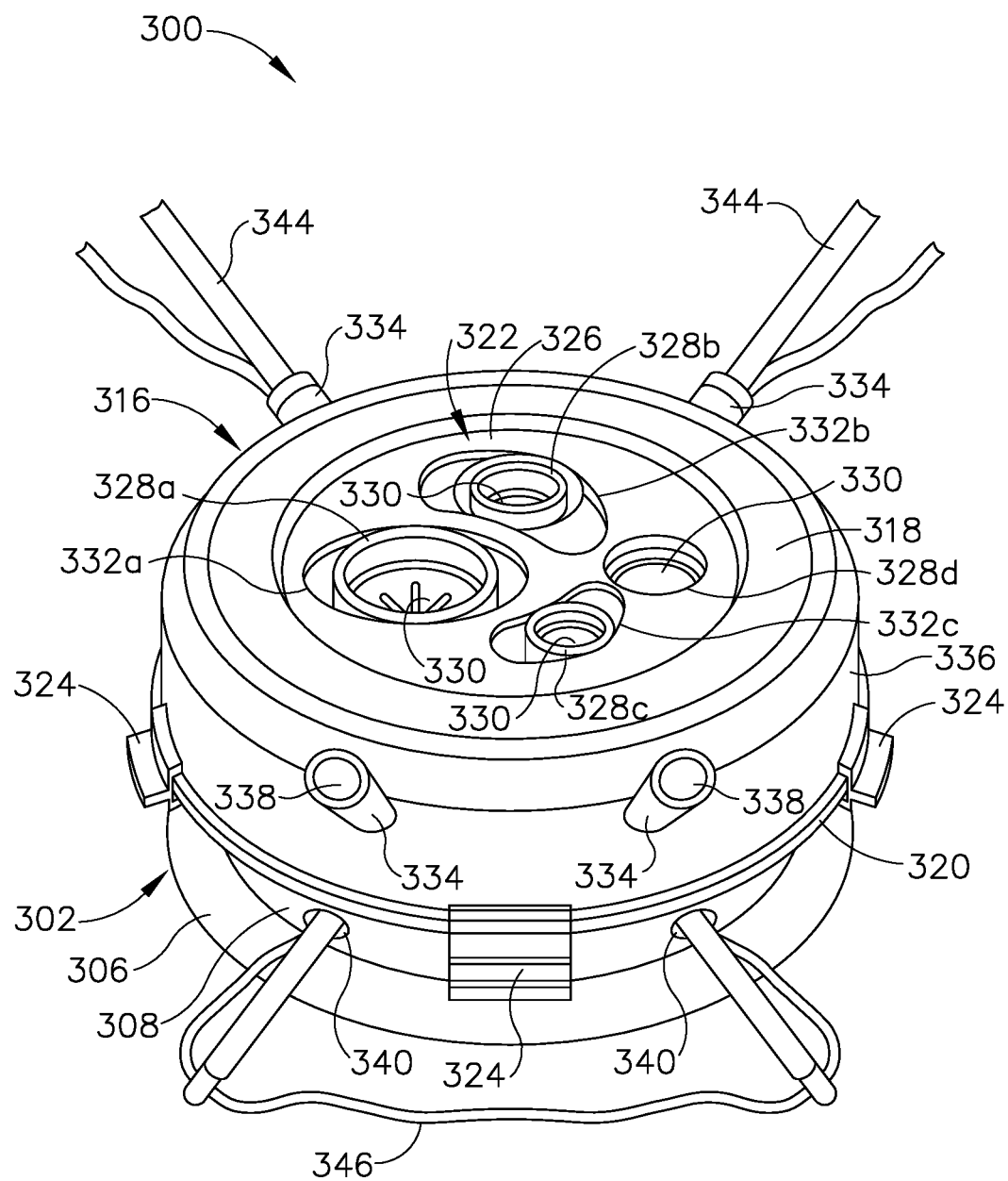
FIG. 22 depicts another exemplary single-incision surgical access device having a proximal housing, showing a suture passer needle and a suture thread directed through first and second needle channels of the device.
Figure 23:
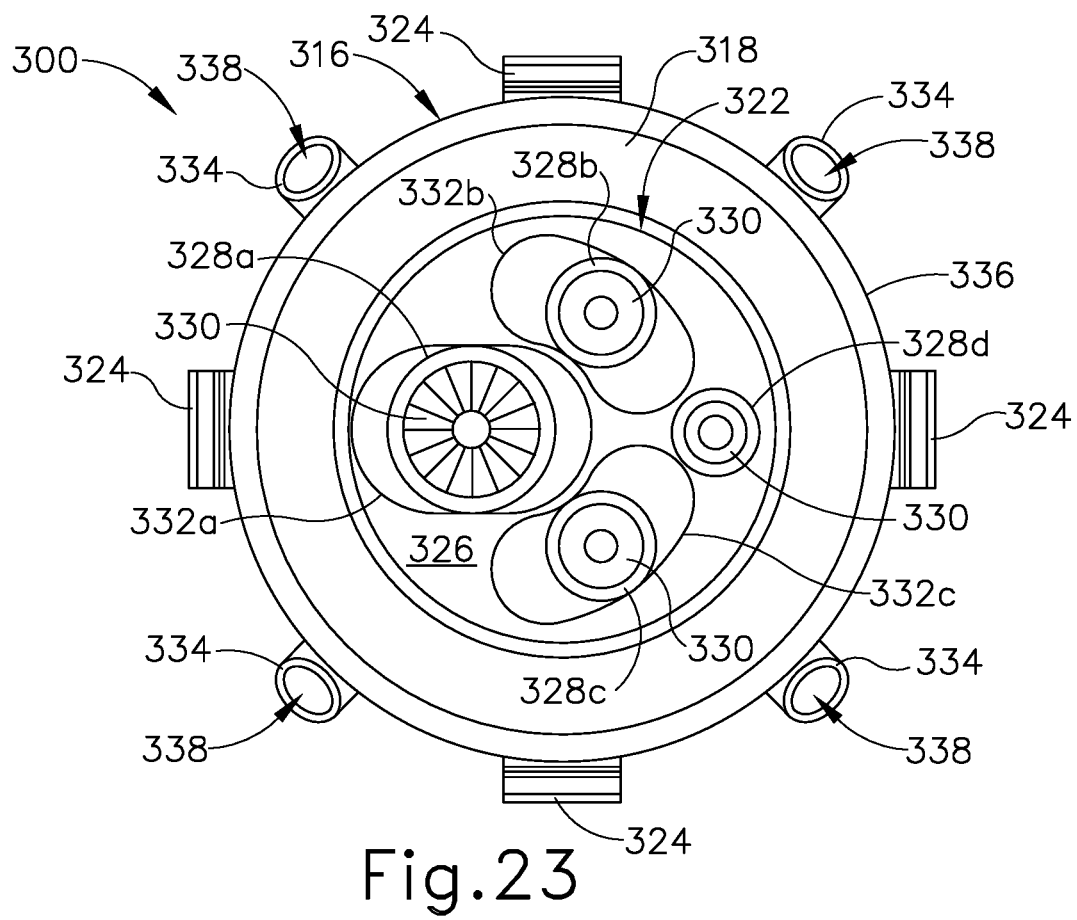
FIG. 23 depicts a top elevational view of the surgical access device of FIG. 22.
Figure 24:
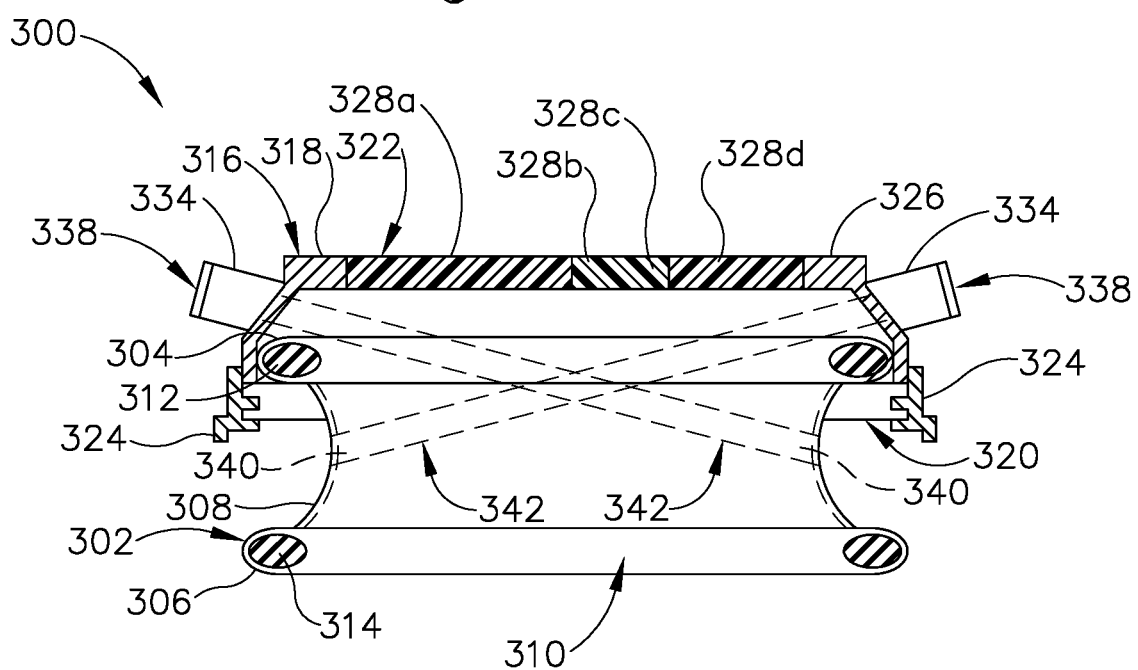
FIG. 24 depicts a schematic side sectional view of the surgical access device of FIG. 22.

A. Exemplary Single-Incision Surgical Access Device Having Proximal Housing with Needle Guide Members FIGS. 22-24 show another exemplary single-incision surgical access device (300) having integrated suture guide features configured to facilitate closure of a tissue opening in which access device (300) is positioned for a surgical procedure. Surgical access device (300) is similar to surgical access devices (100, 180, 230, 280) described above in that access device (300) includes a tissue retractor (302) having a flexible annular body with a proximal flange (304) (see FIG. 24), a distal flange (306), a medial body portion (308) extending axially between proximal and distal flanges (304, 306), and a central passage (310) extending axially through the annular body. Further, an outer lip of proximal flange (304) houses a proximal resilient ring (312), and an outer lip of distal flange (306) houses a distal resilient ring (314). Surgical access device (300) may further include an insufflation port (not shown).

Surgical access device (300) differs from the previously described surgical access devices (100, 180, 230, 280) in that access devices (300) includes a proximal housing (316) coupled to tissue retractor (302) and configured to enclose a proximal portion of tissue retractor (302), including proximal flange (304) and a proximal opening to central passage (310). Proximal housing (316) includes an annular housing cover (318) arranged proximally of proximal flange (304), an annular housing support (320) arranged distally of proximal flange (304), and a circular housing base member (322) accessible through a central opening of annular housing cover (318). Housing cover (318) is releasably coupled to housing support (320) by latches (324) arranged circumferentially about an outer perimeter of proximal housing (316). In various examples, proximal housing (316) may be configured as a rigid structure.

Housing base member (322) includes a base plate (326) and a plurality of instrument entry guide members (328a, 328b, 328c, 328d) supported by base plate (326). Each instrument entry guide member (328a, 328b, 328c, 328d) is configured to guide a surgical instrument (not shown) through a respective surgical instrument channel extending axially through proximal housing (316) and opening to central passage (310) of tissue retractor (302). In the present example, as shown best in FIGS. 22 and 23, proximal housing (316) includes a first instrument entry guide member (328a) providing access to an instrument channel of a large diameter, second and third instrument entry guide members (328b, 328c) each providing access to a respective instrument channel of a medium diameter, and a fourth instrument entry guide member (328d) providing access to an instrument channel of a small diameter. Each instrument entry guide member (328a, 328b, 328c, 328d) includes a sealing element (330) configured to sealingly engage a surgical instrument directed therethrough, and thereby maintain insufflation during a surgical procedure.

In the present example, first, second, and third instrument entry guide members (328a, 328b, 328c) are movable relative to base plate (326) of housing base member (322) along respective tracks (332a, 332b, 332c). Tracks (332a, 332b, 332c) enable instrument entry guide members (328a, 328b, 328c) to move relative to base plate (326) along respective predefined paths in axial, radial, and/or arcuate directions. Advantageously, this mobility of instrument entry guide members (328a, 328b, 328c), and their respective instrument channels, facilitates optimal positioning of surgical instruments directed distally therethrough during a surgical procedure. Proximal housing (316), including base plate (326), may include various additional or alternative features according to one or more teachings of U.S. Pat. No. 8,251,900, entitled "Surgical Access Device and Methods Providing Seal Movement in Predefined Paths," issued Aug. 28, 2012, the disclosure of which is incorporated by reference herein.

Similar to surgical access devices (100, 180, 230, 280) described above, surgical access device (300) further includes integrated suture guide features configured to guide application of suture threads to tissue for closure of a tissue opening. In particular, proximal housing (316) includes a plurality of circumferentially arranged needle entry guide members (334) projecting proximally, angularly outwardly from a sidewall (336). In the present example, each entry needle guide member (334) is shown in the form of a tubular structure. As shown best in FIG. 24, each needle entry guide member (334) defines a needle entrance port (338) that communicates with a corresponding needle exit port (340) formed on medial body portion (308) of tissue retractor (302) to define a corresponding needle channel (342) extending through surgical access device (300) and obliquely relative to a central axis thereof.

As shown in FIG. 22, and as further illustrated by cross-reference with FIGS. 28A-28F, described below, each needle channel (342) is configured to guide a suture passer needle (344) and a suture thread (346) therethrough along an oblique suture path extending through surgical access device (300) and adjacent tissue. Similar to surgical access devices (100, 180, 230, 280) described above, access device (300) of the present example includes four needle channels (342) arranged uniformly in a circumferential direction such that first and second needle channels (342) lie in a first axial plane extending through the central axis of access device (300), and second and third needle channels (342) lie in a second axial plane extending through the central axis, perpendicularly to the first axial plane. Additionally, as best shown in FIG. 23, needle entry guide members (334) and their respective needle channels (342) are circumferentially offset from the surgical instrument channels defined by instrument entry guide members (328a, 328b, 328c, 328d) of proximal housing (316). Accordingly, the resulting suture paths extend between, rather than through, the instrument channels. Further, needle entrance and exit ports (338, 340) are arranged uniformly in axial and radial directions such that each suture path defines the same suture path angle relative to the central axis. Those of ordinary skill in the art will appreciate that other versions of surgical access device (300) may include needle ports (338, 340) arranged in various other quantities and configurations, which may define a variety of suture path angles.

Figure 25:
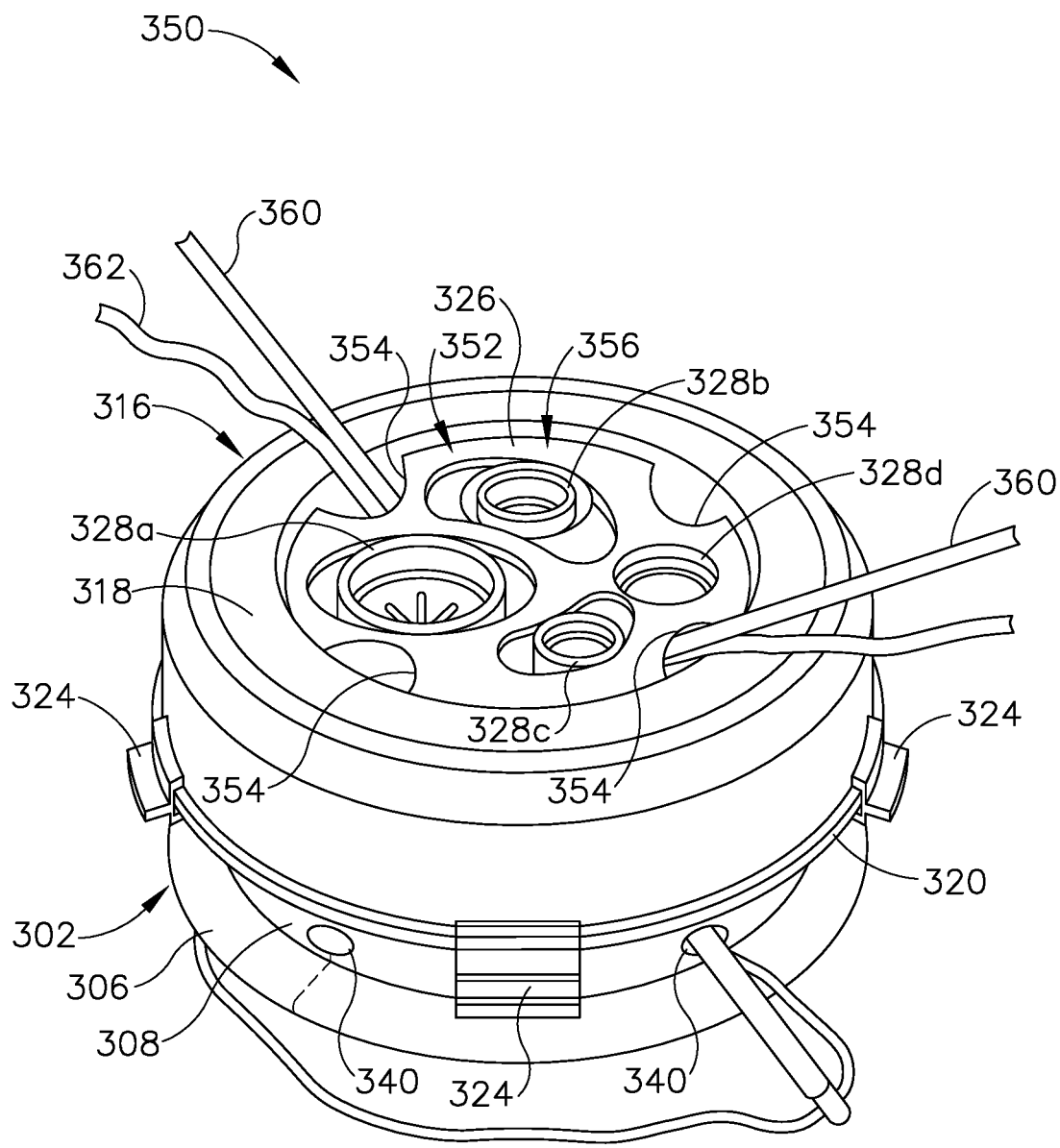
FIG. 25 depicts a perspective view of another exemplary single-incision surgical access device having a proximal housing, showing a suture passer needle and a suture thread directed through first and second needle channels of the device.
Figure 26:
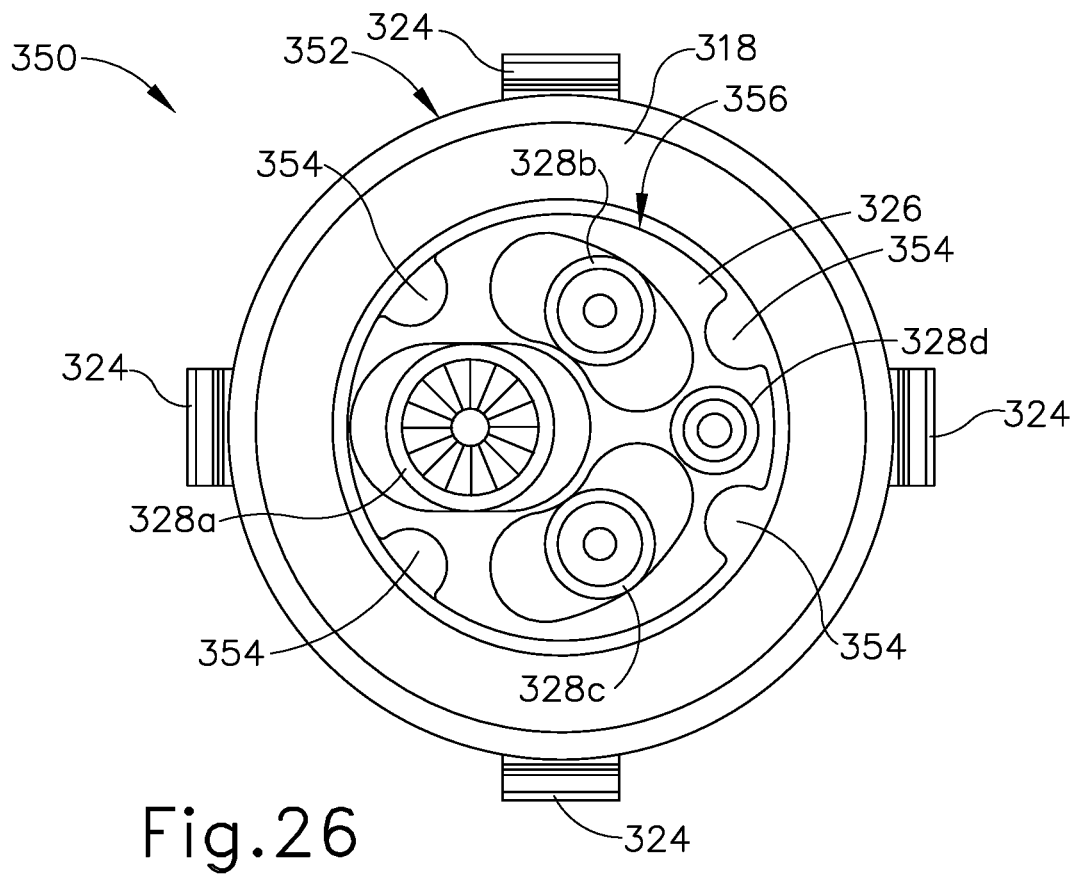
FIG. 26 depicts a top elevational view of the surgical access device of FIG. 25.
Figure 27:
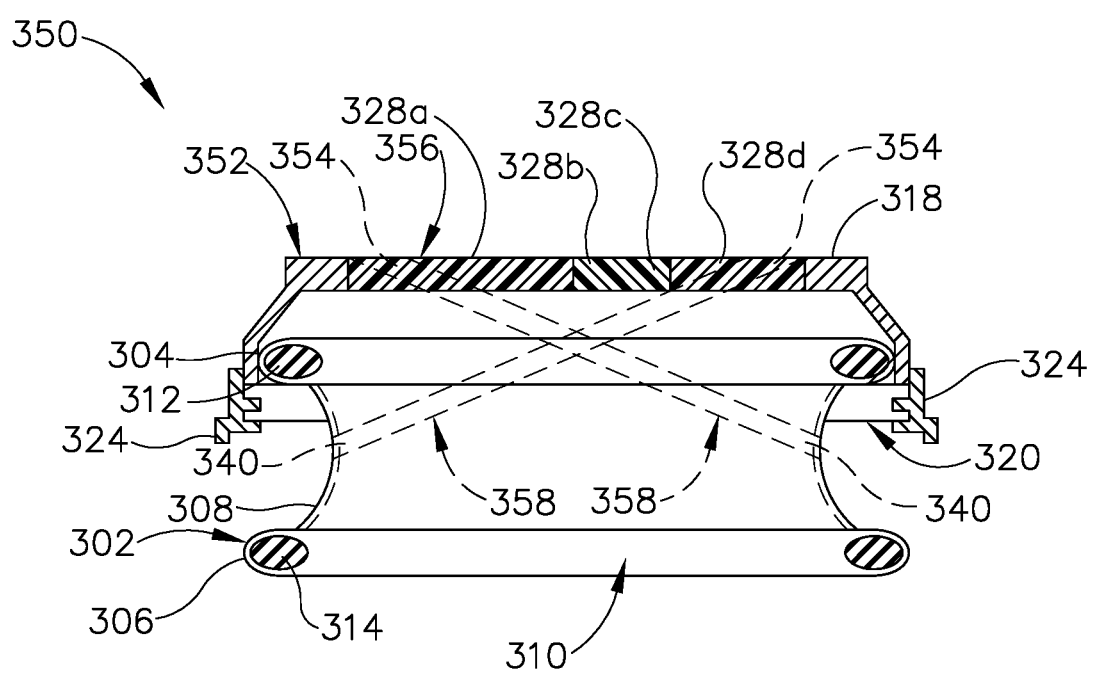
FIG. 27 depicts a schematic side sectional view of the surgical access device of FIG. 25.

B. Exemplary Single-Incision Surgical Access Device Having Proximal Housing with Needle Entrance Ports in Proximal Face FIGS. 25-27 show another exemplary single-incision surgical access device (350) having integrated suture guide features configured to facilitate closure of a tissue opening in which access device (350) is positioned for a surgical procedure. Surgical access device (350) is similar to surgical access device (300) described above, except as otherwise described in detail below. In that regard, like reference numerals in FIGS. 25-27 refer to like features described above in connection with FIGS. 22-24.

Surgical access device (350) differs from surgical access device (300) in that proximal housing (352) of access device (350) includes needle entrance ports (354) arranged in housing base member (356). Proximal housing (350), including housing base member (356), is otherwise similar to proximal housing (316) described above, with needle entry guide members (334) being omitted. In the present example, each needle entrance port (354) is shown in the form of a generally semi-circular opening formed at an outer circumference of housing base member (356), adjacent to an inner circumference of housing cover (318). Like needle entrance ports (338), needle entrance ports (354) are arranged with uniform circumferential spacing therebetween, and are circumferentially offset from instrument entry guide members (328a, 328b, 328c, 328d). Additionally, each needle entrance port (354) communicates with a corresponding needle exit port (340) arranged on an opposed side of tissue retractor (302) to define a respective needle channel (358). Because needle entrance ports (354) of surgical access device (350) are arranged radially inwardly relative to needle entrance ports (338) of access device (300), needle channels (358) may define slightly steeper suture path angles than needle channels (342) of access device (300).

C. Exemplary Wound Closure Procedure Using Single-Incision Surgical Access Device Having Proximal Housing FIGS. 28A-28F show steps of an exemplary procedure for suturing closed a tissue opening (142) formed in tissue (140) using single-incision surgical access device (350) as a wound closure device. While these steps are shown and described in connection with surgical access device (350), it will be understood that these steps may be similarly implemented in connection with surgical access device (300) of FIGS. 22-24.

Figure 28A:
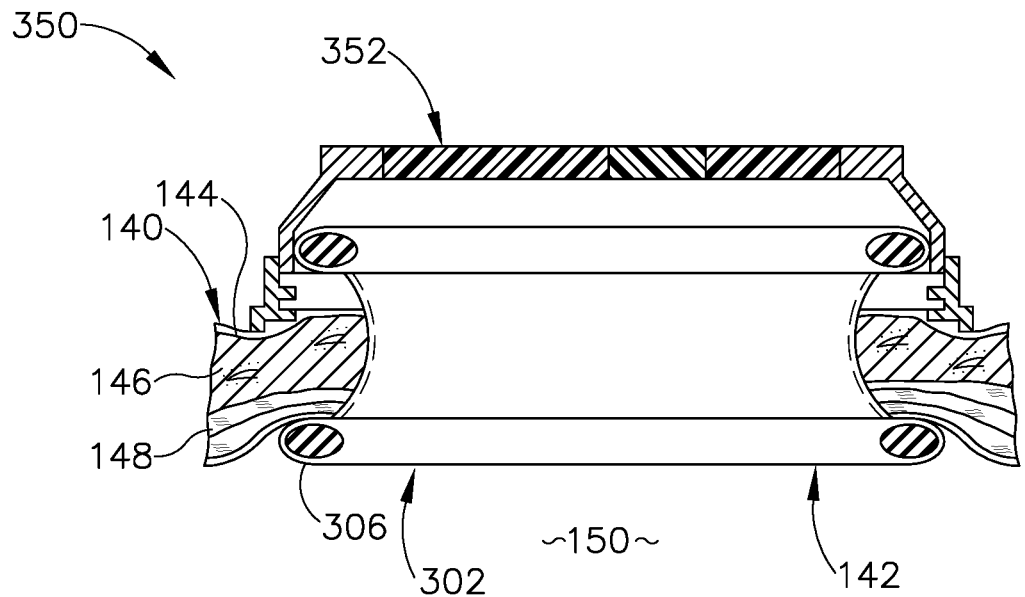
FIG. 28A depicts a schematic side sectional view of the surgical access device of FIG. 25, showing the device positioned within a tissue opening.
Figure 28B:
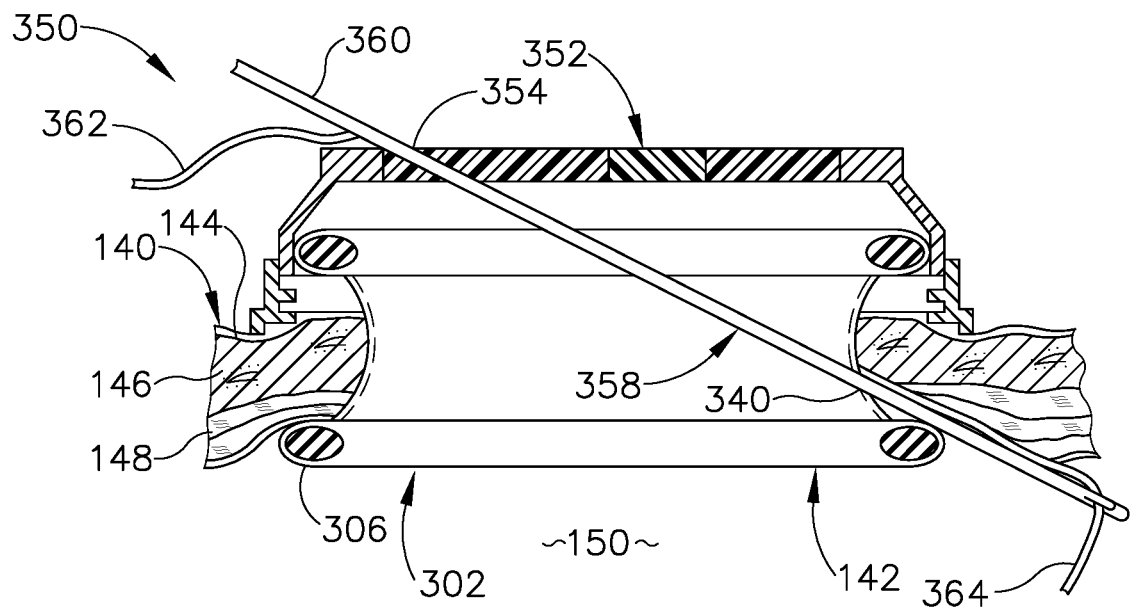
FIG. 28B depicts a schematic side sectional view of the surgical access device and tissue of FIG. 28A, showing a suture passer needle and a suture thread being directed along a first suture path extending through a first needle channel of the device and adjacent tissue.

FIG. 28A shows surgical access device (350) positioned within a tissue opening (142). Following completion of one or more surgical procedures, a suture passer needle (360) carrying a thread end (364) of a first suture thread (362) is directed distally through surgical access device (350) and a first portion of tissue fascia (148) along a first suture path. In particular, suture passer needle (360) and thread end (364) are directed through a first needle entrance port (354) in proximal housing (352), along a respective first needle channel (358), through a corresponding first needle exit port (340), and through an adjacent first portion of tissue fascia (148) located proximally of (i.e., above) distal flange (306), into body cavity (150). Suture passer needle (360) is then manipulated to deposit thread end (364) within body cavity (150), and is then withdrawn proximally from surgical access device (350) along the first suture path.

Figure 28C:
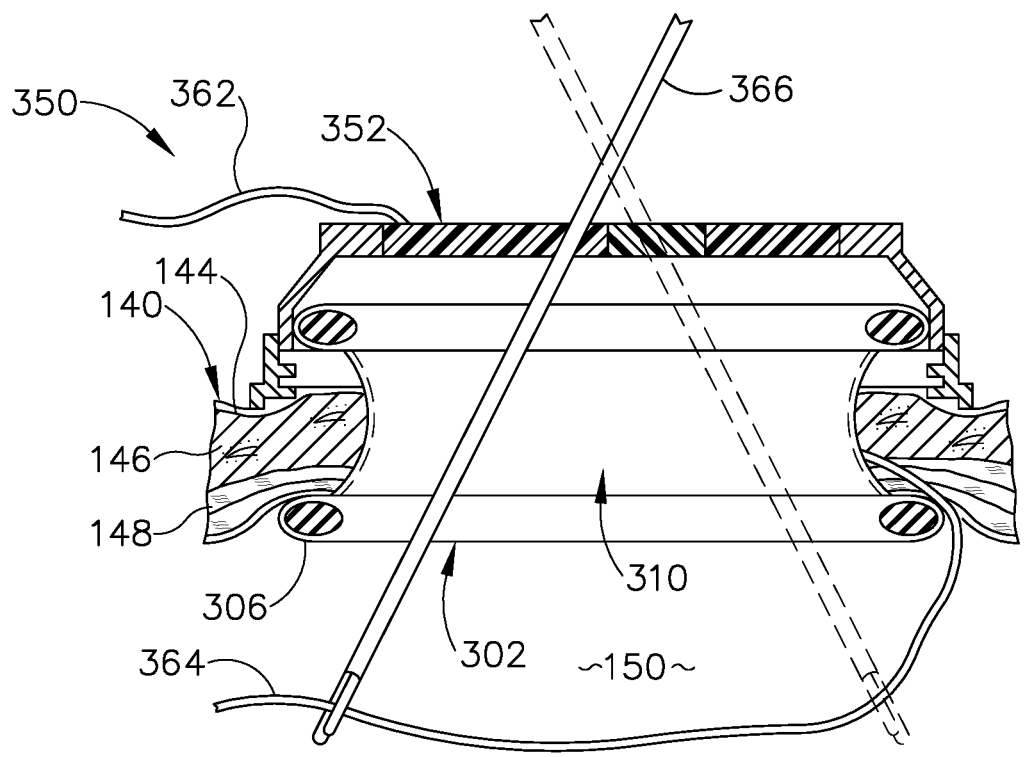
FIG. 28C depicts a schematic side sectional view of the surgical access device and tissue of FIG. 28B, showing a surgical instrument directed distally through an instrument channel of the device to move a deposited end of the suture thread within a body cavity from a first side of the device toward a second side of the device.
Figure 28D:
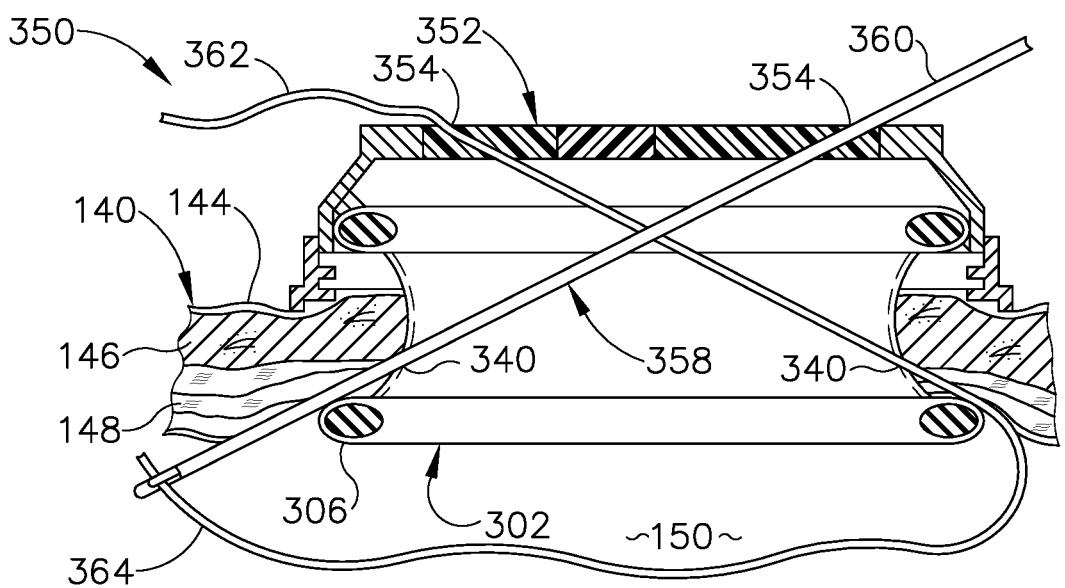
FIG. 28D depicts a schematic side sectional view of the surgical access device and tissue of FIG. 28C, showing the suture passer needle being directed along a second suture path extending through a second needle channel of the device and adjacent tissue to recapture the deposited end of the suture thread.
Figure 28E:
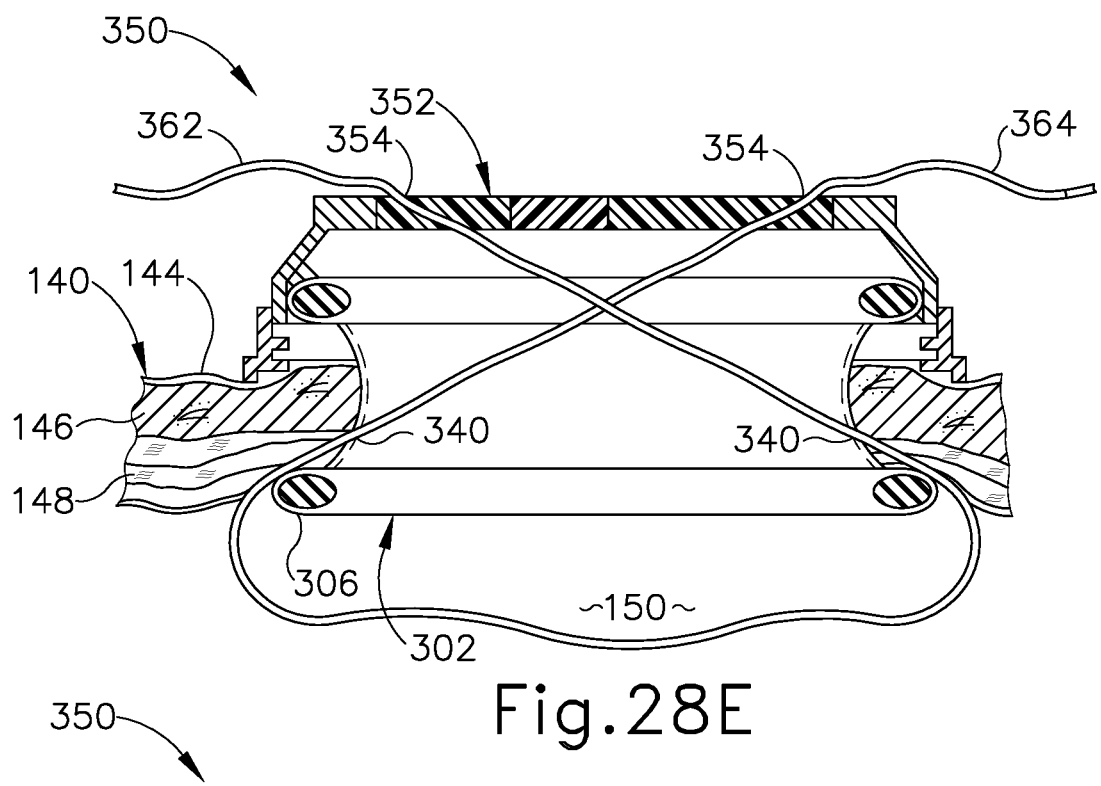
FIG. 28E depicts a schematic side sectional view of the surgical access device and tissue of FIG. 28D, showing the suture thread extending through the device and tissue along the first and second suture paths.

As shown in FIG. 28C, a grasping instrument (366) may be inserted distally through one of the instrument entry guide members (328a, 328b, 328c, 328d) of proximal housing (352), and manipulated to grasp and move thread end (364) toward an opposing side of surgical access device (350) so thread end (364) may be withdrawn proximally along a second suture path, shown FIG. 28D. Alternatively, or in addition, suture passer needle (360) may be provided with one or more steerable sections, such as a steerable tip, configured to facilitate transfer of thread end (364) between opposing sides of access device (350) within body cavity (150).

As shown in FIG. 28D, suture passer needle (360) is directed distally through surgical access device (280) along a second suture path extending through an opposing second needle entrance port (354), a corresponding second needle channel (358) and second needle exit port (340), and an adjacent second portion of tissue fascia (148), into body cavity (150). Suture passer needle (360) is then manipulated to recapture thread end (364) of first suture thread (362), and suture passer needle (360) and thread end (364) are withdrawn proximally along the second suture path, yielding the suture thread configuration shown in FIG. 28E. Similar steps are then repeated to apply a second suture thread (368), shown in FIG. 28F, to tissue (140) via third and fourth suture paths extending through surgical access device (350) and corresponding third and fourth portions of fascia (148).

Figure 28F:
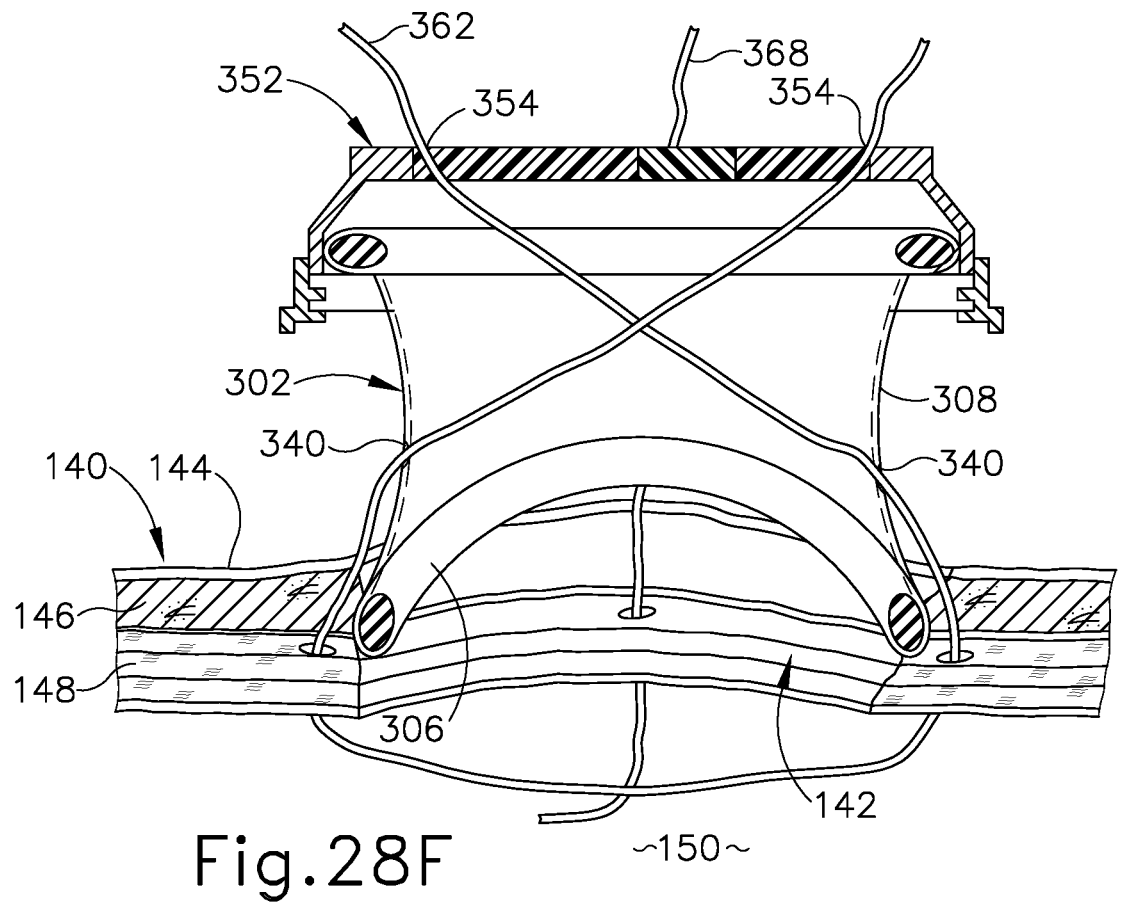
FIG. 28F depicts a schematic side sectional view of the surgical access device and tissue of FIG. 28E, showing proximal removal of the device from the tissue opening following application of a second suture thread along third and fourth suture paths extending through third and fourth needle channels of the device and adjacent tissue.

As shown in FIG. 28F, following application of first and second suture threads (362, 368) to tissue (140), surgical access device (350) is withdrawn proximally from tissue opening (142). As access device (350) is fully withdrawn from tissue opening (142), suture threads (362, 368) fully release from access device (350), thereby yielding a suture thread configuration similar to that shown in FIG. 8F, described above. One or more suture knots (not shown) may then be formed to fully close tissue opening (142), as described above in connection with FIG. 8G.

VII. EXEMPLARY SINGLE-INCISION SURGICAL ACCESS DEVICE HAVING TISSUE RETRACTOR WITH SURGICAL INSTRUMENT CHANNELS AND NEEDLE ENTRANCE PORTS

Figure 29:
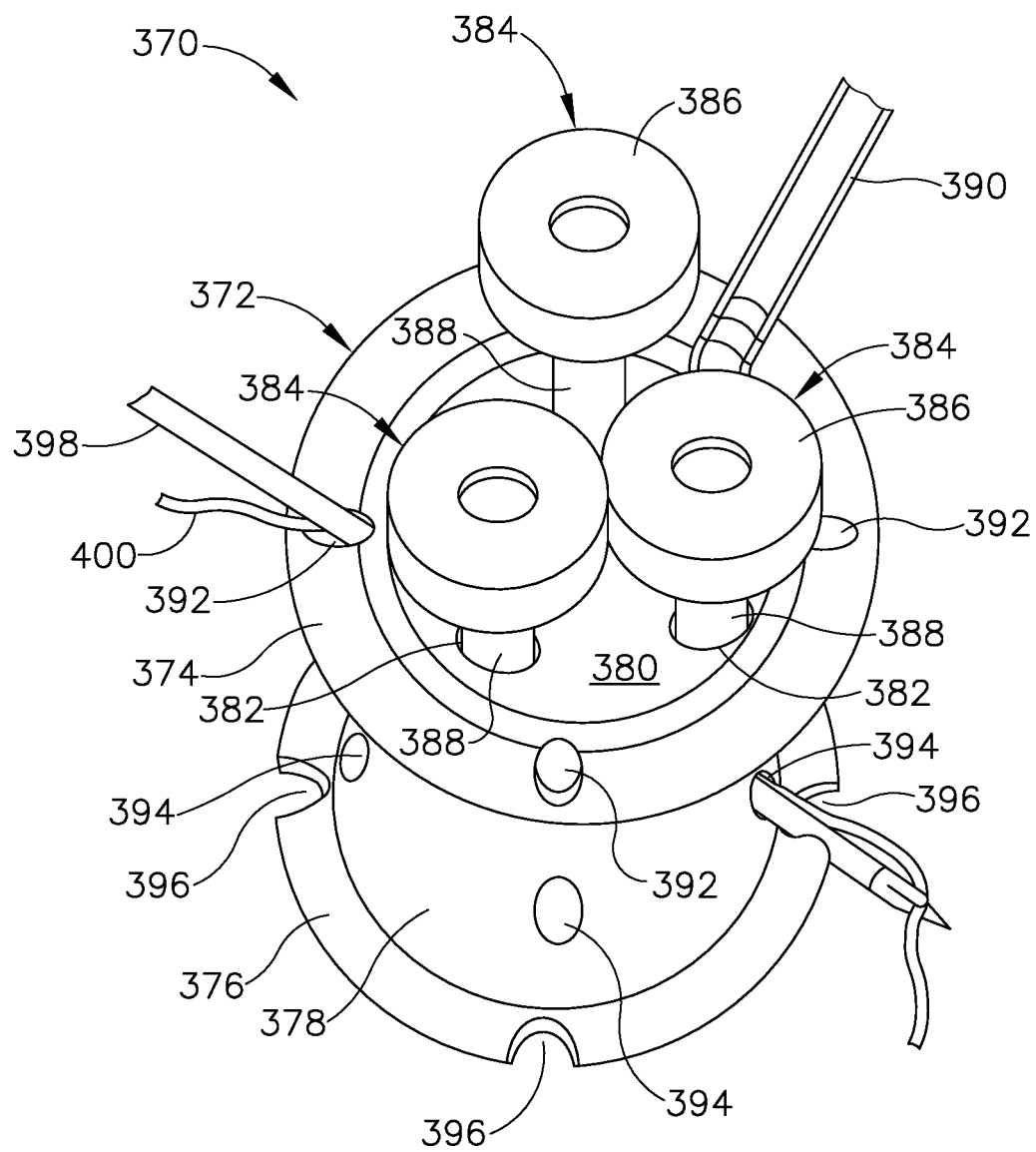
FIG. 29 depicts a perspective view of another exemplary single-incision surgical access device, showing a suture passer needle and a suture thread directed through a first needle channel of the device.
Figure 30:
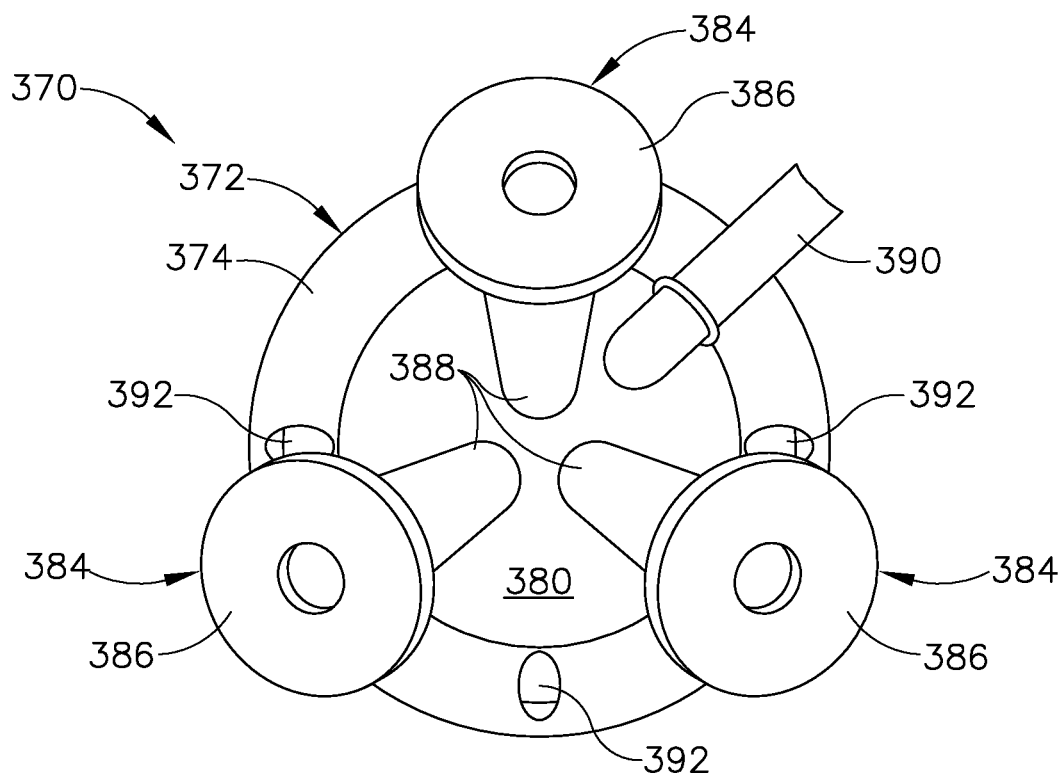
FIG. 30 depicts a top perspective view of the surgical access device of FIG. 29, showing cannula devices positioned within instrument channels of the surgical access device.
Figure 31:
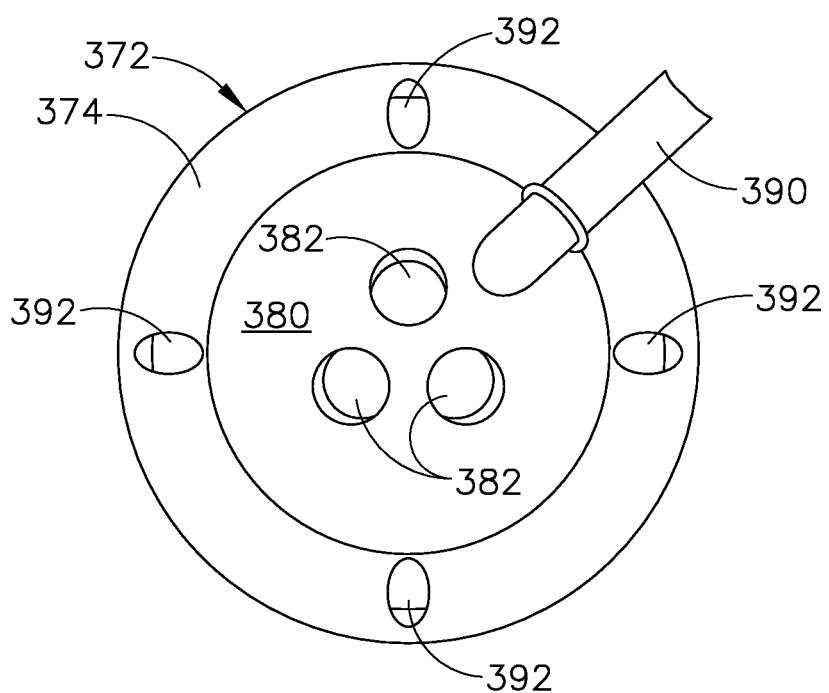
FIG. 31 depicts a top perspective view of the surgical access device of FIG. 30, showing the surgical access device without the cannula devices of FIG. 30.

FIGS. 29-31 show another exemplary single-incision surgical access device (370) having integrated suture guide features configured to facilitate closure of a tissue opening in which access device (370) is positioned for a surgical procedure. Surgical access device (370) includes a tissue retractor (372) having a flexible body defining a proximal flange (374), a distal flange (376), and a medial body portion (378) extending therebetween. Unlike annular tissue retractors (102, 182, 232, 282, 302) described above, tissue retractor (372) omits a central passage extending fully through retractor (372) along a central axis thereof. Instead, tissue retractor (372) includes a central wall (380) arranged radially inward of proximal flange (374) and recessed distally from proximal flange (374). Central wall (380) may be arranged closer to proximal flange (374) than distal flange (376) so as to define a distal cavity (not shown) that opens distally to distal flange (376).

Tissue retractor (372) further includes a plurality of surgical instrument channels (382) extending axially through central wall (380). In the present example, tissue retractor (372) includes three surgical instrument channels (382) arranged circumferentially uniformly about the central axis of retractor (372). In alternative examples, various other quantities and arrangements of instrument channels (382) may be provided. Each instrument channel (382) is configured to guide a surgical instrument distally through tissue retractor (372) and into a body cavity. In the present example, surgical access device (370) includes a plurality of cannula devices (384) arranged within instrument channels (382). Each cannula device (384) includes a head (386) and a shaft (388) defining a lumen, and is configured to guide a surgical instrument distally through tissue retractor (372) and into a body cavity (150). Each cannula device (384) may include an internal sealing element (not shown) configured to sealingly engaging the outer surface of a surgical instrument inserted therethrough to thereby maintain insufflation during a surgical procedure. In that regard, surgical access device (370) further includes an insufflation port (390) extending distally through central wall (380) and configured to direct insufflation fluid distally through retractor (372) and into a body cavity (150).

Surgical access device (370) further includes integrated suture guide features shown in the form of a plurality of needle entrances ports (392) arranged circumferentially on proximal flange (374); a corresponding plurality of needle exit ports (394) arranged circumferentially on a distal portion of medial body portion (378); and a corresponding plurality of needle guide notches (396) arranged circumferentially on distal flange (376). Each needle entrance port (392) cooperates with a respective needle exit port (394) to define a corresponding needle channel (not shown) extending through surgical access device (370) and obliquely relative to its central axis. Each needle channel and its respective needle guide notch (396) is configured to guide a suture passer needle (398) and a suture thread (400) along a suture path extending obliquely through access device (370) and an adjacent portion of tissue fascia (148).

Similar to surgical access devices (100, 180, 230, 280, 300, 350) described above, access device (370) of the present example includes four sets of needle entrance ports (392) and corresponding needle exit ports (394) and needle guide notches (396), the sets being arranged uniformly in a circumferential direction. Consequently, first and second suture paths defined by needle ports (392, 394) and guide notches (396) lie in a first axial plane extending through the central axis of device (370). Third and fourth suture paths defined by needle ports (392, 394) and guide notches (396) lie in a second axial plane extending through the central axis, perpendicularly to the first axial plane. Additionally, needle ports (392, 394) are arranged uniformly in axial and radial directions such that each suture path defines the same suture path angle relative to the central axis. Those of ordinary skill in the art will appreciate that other versions of surgical access device (370) may include needle ports (392, 394) and needle guide notches (396) arranged in various other quantities and configurations, which may define a variety of suture path angles.

Any one or more of the exemplary single-incision surgical access devices and related methods described above, and variations thereof, may be implemented in conventional surgical procedures conducted by a medical professional as well as in robotic-assisted surgical procedures. For example, various teachings herein may be readily incorporated into a robotic surgical system such as one or more of the DAVINCI™ systems by Intuitive Surgical, Inc., of Sunnyvale, Calif., including their SP™ surgical system. Exemplary robotic surgical systems and related features, which may be combined with any one or more of the exemplary surgical access devices and methods disclosed herein, are disclosed in the following: U.S. Pat. No. 8,068,649, entitled "Method and Apparatus for Transforming Coordinate Systems in a Telemanipulation System," issued Nov. 29, 2011; U.S. Pat. No. 8,517,933, entitled "Retraction of Tissue for Single Port Entry, Robotically Assisted Medical Procedures," issued Aug. 27, 2013; U.S. Pat. No. 8,545,515, entitled "Curved Cannula Surgical System," issued Oct. 1, 2013; U.S. Pat. No. 8,551,115, entitled "Curved Cannula Instrument," issued Oct. 8, 2013; U.S. Pat. No. 8,623,028, entitled "Surgical Port Feature," issued Jan. 7, 2014, the disclosure of which is incorporated by reference herein; U.S. Pat. No. 8,771,180, entitled "Retraction of Tissue for Single Port Entry, Robotically Assisted Medical Procedures," issued Jul. 8, 2014, the disclosure of which is incorporated by reference herein; U.S. Pat. No. 8,888,789, entitled "Curved Cannula Surgical System Control," issued Nov. 18, 2014; U.S. Pat. No. 9,254,178, entitled "Curved Cannula Surgical System," issued Feb. 9, 2016; U.S. Pat. No. 9,283,050, entitled "Curved Cannula Surgical System," issued Mar. 15, 2016; U.S. Pat. No. 9,320,416, entitled "Surgical Instrument Control and Actuation," issued Apr. 26, 2016, the disclosure of which is incorporated by reference herein; U.S. Pat. No. 9,339,341, entitled "Direct Pull Surgical Gripper," issued May 17, 2016; U.S. Pat. No. 9,358,074, entitled "Multi-Port Surgical Robotic System Architecture," issued Jun. 7, 2016; U.S. Pat. No. 9,572,481, entitled "Medical System with Multiple Operating Modes for Steering a Medical Instrument Through Linked Body Passages," issued Feb. 21, 2017; U.S. Pat. No. 9,636,186, entitled "Multi-User Medical Robotic System for Collaboration or Training in Minimally Invasive Surgical Procedures," issued May 2, 2017; U.S. Pat. Pub. No. 2014/0066717, entitled "Surgical Port Feature," published Mar. 6, 2014, issued as U.S. Pat. No. 10,245,069 on Apr. 2, 2019, the disclosure of which is incorporated by reference herein; U.S. Pat. Pub. No. 2017/0128041, entitled "Laparoscopic Ultrasound Robotic Surgical System," published May 11, 2017; and U.S. Pat. Pub. No. 2017/0128144, entitled "Laparoscopic Ultrasound Robotic Surgical System," published May 11, 2017, the disclosure of which is incorporated by reference herein; and U.S. Pat. Pub. No. 2017/0128145, entitled "Laparoscopic Ultrasound Robotic Surgical System," published May 11, 2017. The disclosure of each of these references is incorporated by reference herein.

The teachings presented herein may be further combined with various teachings of any one or more of the following: U.S. application Ser. No. 15/637,690, entitled "Needle Guide Instrument with Transverse Suture Capture Feature," filed on Jun. 29, 2017, published as U.S. Pub. No. 2019/0000443 on Jan. 3, 2019, the disclosure of which is incorporated by reference herein; U.S. application Ser. No. 15/637,702, entitled "Suture Grasping Instrument," filed on Jun. 29, 2017, published as U.S. Pub. No. 2019/0000440 on Jan. 3, 2019, the disclosure of which is incorporated by reference herein; U.S. application Ser. No. 15/637,683, published as U.S. Pub. No. 2019/0000505 on Jan. 3, 2019, incorporated by reference above; U.S. application Ser. No. 15/637,688, issued as U.S. Pat. No. 10,485,580 on Nov. 26, 2019, incorporated by reference above; U.S. application Ser. No. 15/637,712, entitled "Suture Passing Instrument with Puncture Site Identification Feature," filed on Jun. 29, 2017, published as U.S. Pub. No. 2019/0000444 on Jan. 3, 2019, the disclosure of which is incorporated by reference herein; U.S. application Ser. No. 15/637,696, entitled "Trocar Obturator with Transverse Needle Ports," filed on Jun. 29, 2017, published as U.S. Pub. No. 2019/0000506 on Jan. 3, 2019, the disclosure of which is incorporated by reference herein; U.S. application Ser. No. 15/637,735, entitled "Trocar Obturator with Detachable Rotary Tissue Fastener," filed on Jun. 29, 2017, published as U.S. Pub. No. 2019/0000502 on Jan. 3, 2019, the disclosure of which is incorporated by reference herein; U.S. application Ser. No. 15/637,778, entitled "Method of Suturing a Trocar Patch Incision," filed on Jun. 29, 2017, published as U.S. Pub. No. 2019/0000496 on Jan. 3, 2019, the disclosure of which is incorporated by reference herein; and/or other patents and patent application publications incorporated by reference above.

VIII. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical access device positionable within a tissue opening, comprising: (a) a tissue retractor including a flexible body configured to engage tissue surrounding the tissue opening; (b) a plurality of surgical instrument channels arranged in a central portion of the tissue retractor, wherein each surgical instrument channel is configured to guide a surgical instrument distally through the surgical access device; (c) at least one needle entrance port arranged on a proximal portion of the surgical access device; and (d) at least one needle exit port arranged distally of the needle entrance port, wherein the at least one needle entrance port and the at least one needle exit port are configured to cooperate to define a needle channel extending distally through the surgical access device and obliquely relative to a central axis thereof, wherein the needle channel is configured to guide a suture passer needle through the surgical access device and adjacent tissue to facilitate closure of the tissue opening.

Example 2

The surgical access device of Example 1, wherein the flexible body of the tissue retractor includes a proximal flange, a distal flange, and a medial body portion extending between the proximal and distal flanges.

Example 3

The surgical access device of Example 2, wherein the at least one needle exit port is arranged at least partially on the medial body portion.

Example 4

The surgical access device of any one or more of Examples 2 through 3, wherein the distal flange includes a plurality of perforated regions arranged circumferentially about the central axis, wherein each perforated region extends radially inwardly from an outer edge of the distal flange.

Example 5

The surgical access device of Example 4, wherein the distal flange houses a resilient ring divided into a plurality of ring segments, wherein the perforated regions of the distal flange are arranged circumferentially at locations between adjacent ends of the ring segments.

Example 6

The surgical access device of Example 5, wherein the ring segments are releasably coupled together by a plurality of coupling members arranged at the adjacent ends of the ring segments.

Example 7

The surgical access device of any one or more of the preceding Examples, wherein the at least one needle entrance port is arranged on the tissue retractor.

Example 8

The surgical access device of any one or more of the preceding Examples, wherein the tissue retractor includes a central passage extending axially through the flexible body, wherein the surgical access device further includes an insert arranged within the central passage, wherein the plurality of surgical instrument channels extend through the insert.

Example 9

The surgical access device of Example 8, wherein the at least one needle entrance port is provided by the insert, wherein the at least one needle channel extends through the insert.

Example 10

The surgical access device of Example 9, wherein the insert includes at least one needle entry guide member protruding from a proximal end portion of the insert, wherein the at least one needle entry guide member defines the at least one needle entrance port.

Example 11

The surgical access device of any one or more of Examples 8 through 9, wherein the insert includes a central channel extending axially therethrough, wherein the at least one needle channel opens to the central channel to define the at least one needle entrance port

Example 12

The surgical access device of any one or more of Examples 8 through 11, wherein the insert comprises a rigid structure.

Example 13

The surgical access device of any one or more of the previous Examples, further comprising a proximal housing coupled to a proximal end of the tissue retractor, wherein the surgical instrument channels extend through the proximal housing, wherein the proximal housing is configured to provide the at least one needle entrance port.

Example 14

The surgical access device of Example 13, wherein the proximal housing includes at least one needle entry guide member protruding from an outer surface of the proximal housing, wherein the at least one needle entry guide member defines the at least one needle entrance port.

Example 15

The surgical access device of Example 13, wherein the at least one needle entrance port extends through a proximal face of the proximal housing.

Example 16

The surgical access device of any one or more of the previous examples, wherein the at least one needle entrance port comprises a plurality of circumferentially spaced needle entrance ports and the at least one needle exit port comprises a plurality of circumferentially spaced needle exit ports, wherein each needle entrance port is configured to cooperate with a corresponding needle exit port to define a respective needle channel extending distally through the surgical access device and obliquely relative to the central axis thereof, wherein each needle channel is configured to guide a suture passer needle through the surgical access device and adjacent tissue.

Example 17

The surgical access device of Example 16, wherein the plurality of needle entrance ports comprises first and second needle entrance ports arranged in a first axial plane, and third and fourth needle entrance ports arranged in a second axial plane angularly offset from the first axial plane, wherein the plurality of needle exit ports comprises first and second needle exit ports arranged in the first axial plane, and third and fourth needle exit ports arranged in the second axial plane, wherein the first, second, third, and fourth needle entrance ports are configured to cooperate with the first, second, third, and fourth needle exit ports, respectively, to define first, second, third, and fourth needle channels, respectively, extending through the surgical access device and obliquely relative to the central axis thereof.

Example 18

A surgical access device positionable within a tissue opening, comprising: (a) a tissue retractor including a flexible body configured to engage tissue surrounding the tissue opening, wherein the tissue retractor defines a central axis; (b) at least one surgical instrument channel configured to guide a surgical instrument distally through the surgical access device; (c) a plurality of needle entrance ports arranged circumferentially about the central axis on a proximal portion of the surgical access device; and (d) a plurality of needle exit ports arranged circumferentially about the central axis distally of the needle entrance ports, wherein each needle entrance port is configured to cooperate with a respective needle exit port to define a needle channel extending distally through the surgical access device and obliquely relative to the central axis, wherein each needle channel is configured to guide a suture passer needle through the surgical access device and adjacent tissue to facilitate closure of the tissue opening.

Example 19

The surgical access device of Example 18, wherein the needle exit ports are arranged on the flexible body of the tissue retractor, wherein the plurality of needle entrance ports includes at least four needle entrance ports and the plurality of needle exit ports includes at least four needle exit ports.

Example 20

A surgical access positionable within a tissue opening, comprising (a) a tissue retractor including a flexible body having a proximal flange, a distal flange, and a medial body portion extending between the proximal and distal flanges, wherein the proximal and distal flanges are configured to engage respective proximal and distal surfaces of the tissue, wherein the medial body portion is configured to engage an axial tissue wall defining the tissue opening; (b) at least one surgical instrument channel configured to guide a surgical instrument distally through the surgical access device; (c) a needle entrance port arranged on a proximal portion of the surgical access device; and (d) a needle exit port arranged distally of the needle entrance port on the medial body portion, wherein the needle entrance port is configured to cooperate with the needle exit port to define a needle channel extending distally through the surgical access device and obliquely relative to a central axis thereof, wherein each needle channel is configured to guide a suture passer needle through the surgical access device and adjacent tissue to facilitate closure of the tissue opening.

IX. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Those of ordinary skill in the art will recognize that various teachings herein may be readily combined with various teachings of: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical access device positionable within a tissue opening, comprising:
    (a) a tissue retractor including a flexible body configured to engage tissue surrounding the tissue opening, wherein the tissue retractor defines a central axis of the surgical access device;
    (b) a plurality of surgical instrument channels arranged in a central portion of the tissue retractor, wherein each surgical instrument channel is configured to guide a surgical instrument distally through the surgical access device;
    (c) a plurality of needle entrance ports spaced circumferentially about the central axis on a proximal portion of the surgical access device;
    (d) a plurality of needle exit ports spaced circumferentially about the central axis distally of the needle entrance ports; and
    (e) a plurality of needle channels, wherein each needle channel is defined by a respective one of the needle entrance ports in cooperation with a respective one of the needle exit ports, wherein each needle channel extends distally through the surgical access device and obliquely relative to the central axis thereof, wherein each needle channel is configured to guide a suture passer needle through the surgical access device and adjacent tissue to facilitate closure of the tissue opening,
    wherein first and second needle channels of the plurality of needle channels are arranged in a first axial plane of the surgical access device,
    wherein third and fourth needle channels of the plurality of needle channels are arranged in a second axial plane of the surgical access device,
    wherein the second axial plane is angularly offset from the first axial plane.

2. The surgical access device of claim 1, wherein the flexible body of the tissue retractor includes a proximal flange, a distal flange, and a medial body portion extending between the proximal and distal flanges.

3. The surgical access device of claim 2, wherein the needle exit ports are arranged at least partially on the medial body portion.

4. The surgical access device of claim 2, wherein the distal flange includes a plurality of perforated regions arranged circumferentially about the central axis, wherein each perforated region extends radially inwardly from an outer edge of the distal flange, wherein the distal flange is configured to rupture at each perforated region to facilitate release of a respective suture from the distal flange.

5. The surgical access device of claim 4, wherein the distal flange houses a resilient ring divided into a plurality of ring segments, wherein the perforated regions of the distal flange are arranged circumferentially at locations between adjacent ends of the ring segments.

6. The surgical access device of claim 5, wherein the ring segments are releasably coupled together by a plurality of coupling members arranged at the adjacent ends of the ring segments.

7. The surgical access device of claim 1, wherein the needle entrance ports are arranged on the tissue retractor.

8. The surgical access device of claim 1, wherein the tissue retractor includes a central passage extending axially through the flexible body, wherein the surgical access device further includes an insert arranged within the central passage, wherein the plurality of surgical instrument channels extend through the insert.

9. The surgical access device of claim 8, wherein the needle entrance ports are provided by the insert, wherein the needle channels extend through the insert.

10. The surgical access device of claim 9, wherein the insert includes a plurality of needle entry guide members protruding from a proximal end portion of the insert, wherein the needle entry guide members define the needle entrance ports.

11. The surgical access device of claim 9, wherein the insert includes a central channel extending axially therethrough, wherein the needle channels open to the central channel to define the needle entrance ports.

12. The surgical access device of claim 8, wherein the insert comprises a rigid structure.

13. The surgical access device of claim 1, further comprising a proximal housing coupled to a proximal end of the tissue retractor, wherein the surgical instrument channels extend through the proximal housing, wherein the proximal housing is configured to provide the needle entrance ports.

14. The surgical access device of claim 13, wherein the proximal housing includes a plurality of needle entry guide members protruding from an outer surface of the proximal housing, wherein the needle entry guide members define the needle entrance ports.

15. The surgical access device of claim 13, wherein the needle entrance ports extend through a proximal face of the proximal housing.

16. A surgical access device positionable within a tissue opening, comprising:
   (a) a tissue retractor including:
      (i) a flexible body configured to engage tissue surrounding the tissue opening, and
      (ii) an insert arranged centrally within the flexible body, wherein the insert includes a central channel that extends axially along a central axis of the tissue retractor;
   (b) at least one surgical instrument channel configured to guide a surgical instrument distally through the surgical access device;
   (c) a plurality of needle entrance ports arranged circumferentially about the central axis on a proximal portion of the surgical access device; and
   (d) a plurality of needle exit ports arranged circumferentially about the central axis distally of the needle entrance ports,
   wherein each needle entrance port opens to the central channel of the insert of the tissue retractor,
   wherein each needle entrance port is configured to cooperate with a respective needle exit port to define a needle channel extending distally through the surgical access device and obliquely relative to the central axis, wherein each needle channel is configured to guide a suture passer needle through the surgical access device and adjacent tissue to facilitate closure of the tissue opening.

17. The surgical access device of claim 16, wherein the needle exit ports are arranged on the flexible body of the tissue retractor, wherein the plurality of needle entrance ports includes at least four needle entrance ports and the plurality of needle exit ports includes at least four needle exit ports.

18. The surgical access device of claim 16, wherein the needle channel comprises a first needle channel that extends in a first axial plane of the surgical access device, wherein the surgical access device further comprises a second needle channel that extends distally and obliquely through the surgical access device along a second axial plane of the surgical access device, wherein the second axial plane is angularly offset from the first axial plane.

19. A surgical access device positionable within a tissue opening, comprising:
   (a) a tissue retractor including a flexible body having a proximal flange, a distal flange, and a medial body portion extending between the proximal and distal flanges, wherein the proximal and distal flanges are configured to engage respective proximal and distal surfaces of the tissue, wherein the medial body portion is configured to engage an axial tissue wall defining the tissue opening, wherein the flexible body includes a perforation line;
   (b) at least one surgical instrument channel configured to guide a surgical instrument distally through the surgical access device;
   (c) a needle entrance port arranged on a proximal portion of the surgical access device; and
   (d) a needle exit port arranged distally of the needle entrance port on the medial body portion,
   wherein the needle entrance port is configured to cooperate with the needle exit port to define a needle channel extending distally through the surgical access device and obliquely relative to a central axis thereof, wherein the needle channel is configured to guide a suture passer needle and a suture through the surgical access device and adjacent tissue to facilitate closure of the tissue opening,
   wherein the flexible body of the tissue retractor is configured to rupture along the perforation line in response to tension applied to the suture to thereby facilitate release of the suture from the flexible body.

20. The surgical access device of claim 19, wherein the perforation line extends radially through at least a portion of the distal flange of the flexible body of the tissue retractor.

* * * * *